US007659289B2

(12) United States Patent
Ghosh et al.

(10) Patent No.: US 7,659,289 B2
(45) Date of Patent: Feb. 9, 2010

(54) HYDROXYETHYLENE-BASED β-SECRETASE INHIBITORS AND USE THEREOF

(75) Inventors: Arun K. Ghosh, West Lafayette, IN (US); Hui Lei, Edmond, OK (US); Thippeswamy Devasamudram, Edmond, OK (US); Jordan J. N. Tang, Edmond, OK (US); Geoffrey M. Bilcer, Edmond, OK (US); Chunfeng Liu, Norman, OK (US)

(73) Assignees: CoMentis, Inc., South San Francisco, CA (US); Oklahoma Medical Research Foundation, Oklahoma City, OK (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/662,915

(22) PCT Filed: Sep. 19, 2005

(86) PCT No.: PCT/US2005/033709

§ 371 (c)(1),
(2), (4) Date: Aug. 2, 2007

(87) PCT Pub. No.: WO2006/034296

PCT Pub. Date: Mar. 30, 2006

(65) Prior Publication Data

US 2008/0125467 A1 May 29, 2008

Related U.S. Application Data

(60) Provisional application No. 60/611,029, filed on Sep. 17, 2004.

(51) Int. Cl.
*A61K 31/426* (2006.01)
(52) U.S. Cl. .................. 514/342; 514/365; 548/204; 546/269.7
(58) Field of Classification Search ................. 514/342, 514/365; 548/204; 546/269.7
See application file for complete search history.

(56) References Cited

U.S. PATENT DOCUMENTS

| 4,801,575 | A | 1/1989 | Pardridge |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 6,180,603 | B1 | 1/2001 | Frey, II |
| 6,287,792 | B1 | 9/2001 | Pardridge et al. |
| 6,313,093 | B1 | 11/2001 | Frey, II |
| 6,372,250 | B1 | 4/2002 | Pardridge |
| 7,335,632 | B2 * | 2/2008 | Ghosh et al. ............ 514/2 |
| 2003/0215398 | A1 | 11/2003 | Frey, II |
| 2003/0215432 | A1 | 11/2003 | Matalon |
| 2003/0216589 | A1 | 11/2003 | Gschneidner et al. |
| 2004/0101904 | A1 | 5/2004 | Pardridge et al. |
| 2004/0102369 | A1 | 5/2004 | Wu et al. |
| 2004/0110928 | A1 | 6/2004 | Crisanti et al. |
| 2004/0121947 | A1 * | 6/2004 | Ghosh et al. ............ 514/12 |

FOREIGN PATENT DOCUMENTS

| WO | WO-89/10134 A1 | 11/1989 |
| WO | WO-96/05309 A2 | 2/1996 |
| WO | WO-96/05309 A3 | 2/1996 |
| WO | WO-03/039454 A2 | 5/2003 |
| WO | WO-03/039454 A3 | 5/2003 |
| WO | WO-2006/034296 A2 | 3/2006 |
| WO | WO-2006/034296 A3 | 3/2006 |

OTHER PUBLICATIONS

Jordan, V. C. Nature Reviews: Drug Discovery, 2, 2003, p. 205-213.*
Ghosh et al. (J Med Chem. Aug. 30, 2001;44(18):2865-8).*
Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Banker et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Banner, D. et al. (1993). "Serine Proteases: 3D Structures, Mechanisms of Action and Inhibitors," Chapter 3 in *Perspectives in Medicinal Chemistry*, Testa, B. et al. eds., Verlag Helvetica Chimica Acta: Basel, Switzerland, pp. 27-43.
Abbott, N.J. et al. (Mar. 1996). "Transporting Therapeutics Across the Blood-Brain Barrier," *Mol. Med. Today* 2(3):106-113.
Banks, W.A. et al. (Nov./Dec. 1992). "Permeability of the Blood-Brain Barrier to Peptides: An Approach to the Development of Therapeutically Useful Analogs," *Peptides* 13(6):1289-1294.
Begley, D.J. (Feb. 1996). "The Blood-Brain Barrier: Principles for Targeting Peptides and Drugs to the Central Nervous System," *J. Pharm. Pharmacol.* 48(2):136-146.
Bertling, W.M. et al. (Jun. 1991). "Use of Liposomes, Viral Capsids, and Nanoparticles as DNA Carriers," *Biotechnol. Appl. Biochem.* 13(3):390-405.
Bickel, U. et al. (Mar. 1, 2001). "Delivery of Peptides and Proteins Through the Blood-Brain Barrier," *Adv. Drug Deliv. Rev.* 46(1-3):247-279.
Bieth, J. (1974). "Some Kinetic Consequences of the Tight Binding of Protein-Proteinase-Inhibitors to Proteolytic Enzymes and Their Application to the Determination of Dissociation Constants," Bayer-Symposium V "Proteinase Inhibitors", *Proceedings of the 2nd International Research Conference on Proteinase Inhibitors*, Grosse Ledder, Fed. Rep. Germany, Oct. 16-20, 1973, pp. 463-469.
Black, K.L. et al. (Nov. 1994). "Enzymatic Barrier Protects Brain Capillaries From Leukotriene C$_4$," *J. Neurosurg.* 81(5):745-751.

(Continued)

*Primary Examiner*—Kamal A Saeed
*Assistant Examiner*—Valerie Rodriguez-Garcia
(74) *Attorney, Agent, or Firm*—Morrison & Foerster LLP

(57) ABSTRACT

The present invention provides novel beta-secretase inhibitors and methods for their use, including methods of treating of Alzheimer's disease.

56 Claims, No Drawings

OTHER PUBLICATIONS

Bobo, R.H. et al. (Mar. 15, 1994). "Convection-Enhanced Delivery of Macromolecules in the Brain," *Proc. Natl. Acad. Sci. USA* 91(6):2076-2080.

Bodor, N. et al. (Dec. 18, 1981). "Site-Specific, Sustained Release of Drugs to the Brain," *Science* 214(4527):1370-1372.

Bodor, N. et al. (1995). "Molecular Packaging," Chapter 14 in *Peptide-Based Drug Design: Controlling Transport and Metabolism*, Taylor, M.D. et al. eds., American Chemical Society: Washington, DC, pp. 317-337.

Bodor, N. et al. (Oct.-Dec. 1997). "Drug Targeting via Retrometabolic Approaches," *Pharmacol. Ther.* 76(1-3):1-27.

Brem, H. et al. (Jul./Aug. 1996). "Polymer-Based Drug Delivery to the Brain," *Sci. Med.* 3(4):52-61.

Calvo, P. et al. (Aug. 2001). "Long-Circulating PEGylated Polycyanoacrylate Nanoparticles as New Drug Carrier for Brain Delivery," *Pharm. Res.* 18(8):1157-1166.

Chavany, C. et al. (Apr. 1992). "Polyalkylcyanoacrylate Nanoparticles as Polymeric Carriers for Antisense Oligonucleotides," *Pharm. Res.* 9(4):441-449.

Chavany, C. et al. (Sep. 1994). "Adsorption of Oligonucleotides Onto Polyisohexylcyanoacrylate Nanoparticles Protects Them Against Nucleases and Increases Their Cellular Uptake," *Pharm. Res.* 11(9):1370-1378.

Chen, P. et al. (Sep. 24, 1998). "Strategies to Target Kyotorphin Analogues to the Brain," *J. Med. Chem.* 41 (20):3773-3781.

Coloma, M.J. et al. (Mar. 2000). "Transport Across the Primate Blood-Brain Barrier of a Genetically Engineered Chimeric Monoclonal Antibody to the Human Insulin Receptor," *Pharm. Res.* 17(3):266-274.

De Strooper, B. et al. (Jan. 22, 1998). "Deficiency of Presenilin-1 Inhibits the Normal Cleavage of Amyloid Precursor Protein," *Nature* 391:387-390.

Doran, S.E. et al. (May 1995). "Gene Expression From Recombinant Viral Vectors in the Central Nervous System After Blood-Brain Barrier Disruption," *Neurosurg.* 36(5):965-970.

Emerich, D.F. et al. (2001). "The Development of the Bradykinin Agonist Labradimil as a Means to Increase the Permeability of the Blood-Brain Barrier: From Concept to Clinical Evaluation," *Clin. Pharmacokinet.* 40(2):105-123.

Ermolieff, J. et al. (Oct. 10, 2000). "Proteolytic Activation of Recombinant Pro-memapsin 2 (Pro-β-secretase) Studied With New Fluorogenic Substrates," *Biochemistry* 39(40):12450-12456.

Fray, A.H. et al. (1986). "A Short, Stereoselective Synthesis of the Lactone Precursor to 2R, 4S, 5S Hydroxyethylene Dipeptide Isosteres," *J. Org. Chem.* 51(25):4828-4833.

Golden, P.L. et al. (Jan. 1997). "Human Blood-Brain Barrier Leptin Receptor. Binding and Endocytosis in Isolated Human Brain Microvessels," *J. Clin. Invest.* 99(1):14-18.

Han, H.-K. et al. (2000). "Targeted Prodrug Design to Optimize Drug Delivery," *AAPS PharmSci* 2(1):1-11.

Harbaugh, R.E. et al. (Dec. 1988). "Use of Implantable Pumps for Central Nervous System Drug Infusions to Treat Neurological Disease," *Neurosurg.* 23(6):693-698.

Hom, R.K. et al. (2004). "Design and Synthesis of Hyrdoxyethylene-Based Peptidomimetic Inhibitors of Human β-Secretase," *J. Med. Chem.* 47(1):158-164.

Hsiao, K. et al. (Oct. 4, 1996). "Correlative Memory Deficits, Aβ Elevation, and Amyloid Plaques in Transgenic Mice," *Science* 274:99-102.

Huang, T.-Y. et al. (1999). "ACNU, MTX and 5-FU Penetration of Rat Brain Tissue and Tumors," *J. Neurooncol.* 45(1):9-17.

Hussain, I. et al. (Jun. 29, 2001). "Prodomain Processing of Asp1 (BACE2) Is Autocatalytic," *J. Biol. Chem.* 276(26):23322-23328.

Huwyler, J. et al. (Nov. 26, 1996). "Brain Drug Delivery of Small Molecules Using Immunoliposomes," *Proc. Natl. Acad. Sci. USA* 93(24):14164-14169.

Huwyler, J. et al. (Sep. 1997). "Receptor Mediated Delivery of Daunomycin Using Immunoliposomes: Pharmacokinetics and Tissue Distribution in the Rat," *J. Pharmcol. Exp. Ther.* 282(3):1541-1546.

Illum, L. (Dec. 2002). "Nasal Drug Delivery: New Developments and Strategies," *Drug Discov. Today* 7(23):1184-1189.

International Search Report mailed Jul. 19, 2006 for PCT Application No. PCT/US2005/033709 filed Sep. 19, 2005, 5 pages.

Kreil, G. et al. (Sep. 1995). "Hyaluronidases—a Group of Neglected Enzymes," *Protein Sci.* 4(9):1666-1669.

Kreuter, J. (Mar. 23, 2001). "Nanoparticulate Systems for Brain Delivery of Drugs," *Adv. Drug Deliv. Rev.* 47(1):65-81.

Kreuter, J. (2002). "Transport of Drugs Across the Blood-Brain Barrier by Nanoparticles," *Curr. Med. Chem.* 2(3):241-249.

Kreuter, J. et al. (Mar. 13, 1995). "Passage of Peptides Through the Blood-Brain Barrier With Colloidal Polymer Particles (Nanoparticles)," *Brain Res.* 674(1):171-174.

Krewson, C.E. et al. (May 22, 1995). "Distribution of Nerve Growth Factor Following Direct Delivery to Brain Interstitium," *Brain Res.* 680(1-2):196-206.

Kroll, R.A. et al. (Apr. 1996). "Increasing Volume of Distribution to the Brain With Interstitial Infusion: Dose, Rather Than Convection, Might be the Most Important Factor," *Neurosurg.* 38(4):746-754.

Kroll, R.A. et al. (May 1998). "Outwitting the Blood-Brain Barrier for Therapeutic Purposes: Osmotic Opening and Other Means," *Neurosurg.* 42(5):1083-1099.

Kumagai, A.K. et al. (Nov. 5, 1987). "Absorptive-Mediated Endocytosis of Cationized Albumin and a β-Endorphin-Cationized Albumin Chimeric Peptide by Isolated Brain Capillaries. Model System of Blood-Brain Barrier Transport," *J. Biol Chem.* 262(31):15214-15219.

Lambert, D.M. (Oct. 2000). "Rationale and Applications of Lipids as Prodrug Carriers," *Eur. J. Pharm. Sci.* 11(Suppl. 2):S15-S27.

Li, J.Y. et al. (Sep. 1999). "Genetically Engineered Brain Drug Delivery Vectors: Cloning, Expression and in Vivo Application of an Anti-Transferrin Receptor Single Chain Antibody-Streptavidin Fusion Gene and Protein," *Protein Engineering* 12(9):787-796.

Lin, X. et al. (Feb. 15, 2000). "Human Aspartic Protease Memapsin 2 Cleaves the β-Secretase Site of β-Amyloid Precursor Protein," *Proc. Natl. Acad. Sci. USA* 97(4):1456-1460.

Matsukado, K. et al. (Jul. 1996). "Enhanced Tumor Uptake of Carboplatin and Survival in Glioma-Bearing Rats by Intracarotid Infusion of Bradykinin Analog, RMP-7," *Neurosurgery* 39(1):125-134.

Miller, G. (Aug. 16, 2002). "Drug Targeting. Breaking Down Barriers," *Science* 297(5584):1116-1118.

Misra, A. et al. (May-Aug. 2003). "Drug Delivery to the Central Nervous System: A Review," *J. Pharm. Pharmaceut. Sci.* 6(2):252-273.

NCBI Accession No. NP_036236, created Jun. 26, 2007, located at <http://www.ncbi.nlm.nih.gov/entrez/viewer.fcgi?db=Protein& id=6912266>, last visited Jul. 17, 2007, four pages.

NCBI Accession No. NP_036237, created Jun. 3, 2007, located at <http://www.ncbi.nlm.nih.gov/entrez/viewer.fcgi?db=Protein &id=19923395>, last visited Jul. 17, 2007, four pages.

Neuwelt, E.A. et al. (1994). "Therapeutic Dilemma of Disseminated CNS Germinoma and the Potential of Increased Platinum-Based Chemotherapy Delivery With Osmotic Blood-Brain Barrier Disruption," *Pediatr. Neurosurg.* 21(1):16-22.

Neuwelt, E.A. ed. (1989). *Implications of the Blood-Brain Barrier and Its Manipulation: vol. 2 Clinical Aspects*, Plenum Press: New York, NY, pp. xvii-xxvi. (Table of Contents Only).

Neuwelt, E.A. et al. (Nov. 1994). "Effect of Blood-Brain Barrier Disruption on Intact and Fragmented Monoclonal Antibody Localization in Intracerebral Lung Carcinoma Xenografts," *J. Nucl. Med.* 35(11):1831-1841.

Palomino, E. et al. (Mar. 1989). "A Dihydropyridine Carrier System for Sustained Delivery of 2',3'-dideoxynucleosides to the Brain," *J. Med. Chem.* 32(3):622-625.

Pardridge, W.M. (Aug. 1986). "Receptor-Mediated Peptide Transport Through the Blood-Brain Barrier," *Endocrine Rev.* 7(3):314-330.

Pardridge, W.M. (1999). "Vector-Mediated Drug Delivery to the Brain," *Adv. Drug Deliv. Rev.* 36(2,3):299-321.

Pardridge, W.M. (Feb. 2002). "Drug and Gene Targeting to the Brain With Molecular Trojan Horses," *Nat. Rev. Drug Discov.* 1(2):131-139.

Pardridge, W.M. et al. (Jun. 1995). "Human Insulin Receptor Monoclonal Antibody Undergoes High Affinity Binding to Human Brain Capillaries in Vitro and Rapid Transcytosis Through the Blood-Brain Barrier in Vivo in the Primate," *Pharm. Res.* 12(6):807-816.

Gennaro, A.R. ed. (1985). *Remington's Pharmaceutical Sciences*, 17th Edition, Mack Publishing Company: Easton, PA, five pages. (Table of Contents Only.).

Rapoport, S.I. (Apr. 2000). "Osmotic Opening of the Blood-Brain Barrier: Principles, Mechanism, and Therapeutic Applications," *Cell Mol. Neurobiol.* 20(2):217-230.

Schwarze, S.R. et al. (Sep. 3, 1999). "In Vivo Protein Transduction: Delivery of a Biologically Active Protein Into the Mouse," *Science* 285(5433):1569-1572.

Somogyi, G. et al. (May 11, 1998). "Targeted Drug Delivery to the Brain via Phosphonate Derivatives I. Design, Synthesis and Evaluation of an Anionic Chemical Delivery System for Testosterone," *Int. J. Pharm.* 166(1):15-26.

Tamai, I. et al. (Jan. 1997). "Structure-Internalization Relationship for Absorptive-Mediated Endocytosis of Basic Peptides at the Blood-Brain Barrier," *J. Pharmacol. Exp. Ther.* 280(1):410-415.

Thorne, R.G. et al. (Sep. 18, 1995). "Quantitative Analysis of the Olfactory Pathway for Drug Delivery to the Brain," *Brain Res.* 692(1-2):278-282.

Thorne, R.G. et al. (2001). "Delivery of Neurotrophic Factors to the Central Nervous System: Pharmacokinetic Considerations," *Clin. Pharmacokinet.* 40(12):907-946.

Wender, P.A. et al. (Nov. 21, 2000). "The Design, Synthesis, and Evaluation of Molecules That Enable or Enhance Cellular Uptake: Peptoid Molecular Transporters," *Proc. Natl. Acad. Sci USA* 97(24):13003-13008.

Wermuth et al. (1996). "Molecular Variations Based on Isoteric Replacements," *Practice of Medicinal Chemistry*, pp. 203-237.

Wu, D. et al. (Oct. 1, 1997). "Drug Targeting of a Peptide Radiopharmaceutical Through the Primate Blood-Brain Barrier in Vivo With a Monoclonal Antibody to the Human Insulin Receptor," *J. Clin. Invest.* 100(7):1804-1812.

Wu, J. et al. (Jul. 2002). "Synthesis and Biological Evaluations of Brain-Targeted Chemical Delivery Systems of [$Nva_2$]-TRH," *J. Pharm. Pharmacol.* 54(7):945-950.

Yoshikawa, T. et al. (Nov. 1992). "Biotin Delivery to Brain With a Covalent Conjugate of Avidin and a Monoclonal Antibody to the Transferrin Receptor," *J. Pharmacol. Exp. Ther.* 263(2):897-903.

Zobel, H.P. et al. (Oct. 1997). "Cationic Polyhexylcyanoacrylate Nanoparticles as Carriers for Antisense Oligonucleotides," *Antisense Nucleic Acid Drug Dev.* 7(5):483-493.

Zordan-Nudo, T. et al. (Dec. 15, 1993). "Effects of Nonionic Detergents on P-Glycoprotein Drug Binding and Reversal of Multidrug Resistance," *Cancer Res.* 53(24):5994-6000.

\* cited by examiner

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Glu Leu Asp Leu Ala Val Glu Phe Trp His Asp Arg
1               5                   10

HYDROXYETHYLENE-BASED β-SECRETASE INHIBITORS AND USE THEREOF

The present application is a National Phase filing under 35 U.S.C. §371 of International Application No. PCT/US2005/033709 filed on 19 Sep. 2005, which claims the benefit of U.S. Provisional Application No. 60/611,029, filed Sep. 17, 2004, which are incorporated herein by reference in their entirety for all purposes.

STATEMENT AS TO RIGHTS TO INVENTIONS MADE UNDER FEDERALLY SPONSORED RESEARCH OR DEVELOPMENT

The invention was supported, in whole or in part, by a National Institutes of Health grants AG-18933 AI-38189 and also GM053386. The Government has certain rights in the invention.

BACKGROUND OF THE INVENTION

Alzheimer's disease is a progressive mental deterioration in a human resulting, inter alia, in loss of memory, confusion and disorientation. Alzheimer's disease accounts for the majority of senile dementias and is a leading cause of death in adults (Anderson, R. N., *Natl. Vital Stat. Rep.* 49:1-87 (2001), the teachings of which are incorporated herein in their entirety). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease (Selkoe, D. J., *Nature* 399: 23-31 (1999)) and is a proteolytic fragment of amyloid precursor protein (APP). APP is cleaved initially by β-secretase followed by γ-secretase to generate Aβ (Lin, X., et al., *Proc. Natl. Acad. Sci. USA* 97:1456-1460 (2000); De Stropper, B., et al., *Nature* 391:387-390 (1998)).

There is a need to develop effective compounds and methods for the treatment of Alzheimer's disease. The present invention fulfills these and other needs.

BRIEF SUMMARY OF THE INVENTION

The present invention provides novel beta-secretase inhibitors and methods for their use, including methods of treating of Alzheimer's disease.

In one aspect, the present invention provides a compound having the formula:

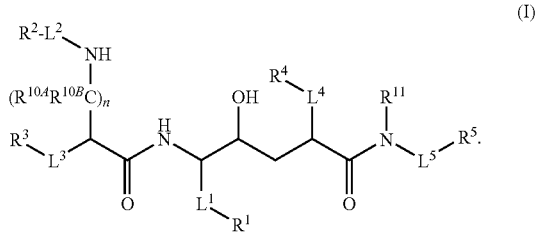

(I)

In Formula (I), n is an integer from 0 to 5.

$R^1$, $R^3$, $R^4$, $R^5$ are independently —$NR^{29}R^{30}$, —$OR^{31}$, —$C(O)R^{32}$, —$S(O)_tR^{32}$, —$N_3$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, amino acid side chain, or -$L^6$-Y. The symbol t represents an integer from 0 to 2.

$R^{29}$ is —$C(O)R^{33}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{32}$ is —$NR^{34}R^{35}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{34}$ is independently —$NR^{36}R^{37}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Where $R^1$, $R^3$, $R^4$, or $R^5$ is —$S(O)_tR^{32}$, then $R^{34}$ is not —$NR^{36}R^{37}$.

$R^{30}$, $R^{31}$, $R^{33}$, $R^{35}$, $R^{36}$, and $R^{37}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^{11}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^6$-Y.

$R^{10A}$ and $R^{10B}$ are independently selected from a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^6$Y. $R^{10A}$ is optionally joined with $R^2$ to form a substituted or unsubstituted cycloalkyl, substituted or unsubstituted heterocycloalkyl, substituted or unsubstituted aryl, or substituted or unsubstituted heteroaryl.

$L^2$ is a bond, —C(O)—, —O(CH$_2$)$_k$—, —C(O)NR$^6$—, —NH—, —C(O)O—, —S—, —S(O)—, —S(O)$_2$—, substituted or unsubstituted alkylene, or substituted or unsubstituted heteroalkylene. $R^6$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol "k" represents an integer from) to 5.

$L^3$ is a bond, —C(O)—, —O—, —C(O)NR$^7$—, —N(R$^7$)—, —C(O)O—, —S—, —S(O)—, —S(O)$_2$—, —NR$^7$—C(O)—NR$^8$—, —NR$^7$—C(O)—O—, substituted or unsubstituted alkylene, or substituted or unsubstituted heteroalkylene. $R^7$ and $R^8$ are, independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^5$ is a bond, —C(O)—, —C(O)NH—, substituted or unsubstituted alkylene, or substituted or unsubstituted heteroalkylene. Y is a carrier moiety.

$L^6$ is selected from a bond, —OP(OH)$_2$O—, —C(O)OR$^{26}$—, —C(O)NHR$^{27}$—, —S(O)$_2$NHR$^{28}$—, substituted or unsubstituted alkylene, substituted or unsubstituted heteroalkylene, or a peptidyl linker. $R^{26}$, $R^{27}$, and $R^{28}$ are each independently selected from the following: substituted or unsubstituted alkyl, substituted or unsubstituted heteroalkyl, cycloalkyl, substituted or unsubstituted heterocycloalkyl, substituted or unsubstituted aryl, or substituted or unsubstituted heteroaryl.

In another aspect of the present invention, the β-secretase inhibitor compounds of the invention can be employed in methods to decrease memapsin 2 β-secretase activity, decrease hydrolysis of a β-secretase site of a memapsin 2 β-secretase substrate, and/or decrease the accumulation of β-amyloid protein relative to the amount of memapsin 2 β-secretase activity, hydrolysis of a β-secretase site, and accumulation of β-amyloid protein, respectively, in the absence of the β-secretase inhibitor.

In another aspect, the present invention provides pharmaceutical compositions comprising a memapsin 2 β-secretase inhibitor compound of the invention or a memapsin 2 β-secretase inhibitor compound in combination with a pharmaceutically acceptable carrier.

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

DETAILED DESCRIPTION OF THE INVENTION

Abbreviations and Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S(O$_2$)—R', where R' is an alkyl group as defined above. R' may have a specified number of carbons (e.g. "C$_1$-C$_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O) NR"R''', —NR"C(O)$_2$R', —NR—C(NR'R"R''')=NR'''', —NR—C(NR'R")=NR''', —S(O)R', —S(O)$_2$R', —S(O)$_2$ NR'R", —NRSO$_2$R', —CN and NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R''', —OC(O)', —C(O)', —CO$_2$', —CONR'R", —OC(O)NR'R", —NR"C(O)', —NR'—C(O) NR"R''', —NR"C(O)$_2$R', —NR—C(NR'R"R''')=NR'''', —NR—C(NR'R")=NR''', —S(O)R', —S(O)$_2$R', —S(O)$_2$ NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (-)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A "hydrophobic" group is a group that does not reduce the solubility of a compound in octane or increases the solubility of a compound in octane. Examples of hydrophobic groups include aliphatic groups, aryl groups, and aralkyl groups.

As used herein, the term "natural amino acid" refers to the twenty-three natural amino acids known in the art, which are as follows (denoted by their three letter acronym): Ala, Arg, Asn, Asp, Cys, Cys-Cys, Glu, Gln, Gly, His, Hyl, Hyp, Ile, Leu, Lys, Met, Phe, Pro, Ser, Thr, Trp, Tyr, and Val. The term "side-chain of an amino acid", as used herein, is the substituent on the alpha-carbon of a natural amino acid.

The term "non-natural amino acid" refers to compounds of the formula NH$_2$—C(R$_{32}$)$_2$—COOH, where R$_{32}$ for each occurrence is, independently, any side chain moiety recognized by those skilled in the art; examples of non-natural amino acids include, but are not limited to: hydroxyproline, homoproline, 4-amino-phenylalanine, norleucine, cyclohexylalanine, α-aminoisobutyric acid, N-methyl-alanine, N-methyl-glycine, N-methyl-glutamic acid, tert-butylglycine, α-aminobutyric acid, tert-butylalanine, ornithine, α-aminoisobutyric acid, 2-aminoindane-2-carboxylic acid, etc. and the derivatives thereof, especially where the amine nitrogen has been mono- or di-alkylated.

A peptide substituent is a sequence of natural or non-natural amino acids that are linked together via an amide bond which is formed by reaction of the α-amine of one amino acid with the α-carboxylic acid of an adjacent amino acid. Preferably, a peptide sequence includes only natural amino acids. In one embodiment, a peptide substituent is a sequence of about 6 natural amino acids. In another embodiment, a peptide substituent is a sequence of 2 natural amino acids. In yet another embodiment, a peptide substituent is 1 natural amino acid.

A "transition state isostere," or "isostere," as used herein, is a compound having peptidyl component where at least one amide linkage between two consecutive natural or non-natural amino acids has been modified such that the —NH— group of the amide has been replaced with a —CH$_2$— and the carbonyl of the amide group has been replaced with a —CH(OH)—. This isostere is also referred to herein as a "hydroxyethylene isostere" because the amide linkage between a pair of amino acids of a peptide is modified to form a hydroxyethylene linkage between the amino acids. A hydroxyethylene group is an isostere of the transition state of hydrolysis of an amide bond. Preferably, an isostere has only one modified amide linkage.

"Memapsin-2," as used herein, refers to proteins identified by National Center for Biotechnology Information ("NCBI") accession number NP_036236 (sometimes referred to as "β-site APP-cleaving enzyme 1" or "BACE-1"), including homologs, isoforms and subdomains thereof that retain proteolytic activity. Sequence identities of active memapsin 2 proteins and protein fragments (and nucleic acid coding sequences thereof) have been previously disclosed and discussed in detail in copending U.S. Application No. 20040121947, and International Application No. PCT/US02/34324 (Publication No. WO 03/039454), which are herein incorporated by reference for all purposes in their entirety.

"Memapsin-1," as used herein, refers to proteins identified by National Center for Biotechnology Information ("NCBI") accession number NP_036237 (sometimes referred to as "β-site APP-cleaving enzyme 2" or "BACE-2") and/or those previously disclosed and discussed in detail in copending U.S. Application No. 20040121947, and International Application No. PCT/US02/34324 (Publication No. WO 03/039454), incorporated by reference herein in their entirety for all purposes, including homologs, isoforms and subdomains thereof that retain proteolytic activity.

"Cathepsin D," as used herein, refers to proteins identified by National Center for Biotechnology Information ("NCBI") accession number NP_036236 (sometimes referred to as "β-site APP-cleaving enzyme 1" or "BACE-1") and or proteins identified by Enzyme Structure Database subclass EC 3.4.23.5., including homologs, isoforms and subdomains thereof that retain proteolytic activity.

A "β-secretase site" is an amino acid sequence that is cleaved by an active memapsin 2 or active fragment thereof. Specific β-secretase sites have also been previously set forth and discussed in detail in copending U.S. Application No. 20040121947, and International Application No. PCT/US02/34324 (Publication No. WO 03/039454), which are herein incorporated by reference for all purposes in their entirety, and include the Swedish mutation sequence, and the native β-amyloid precursor protein cleavage sequence. Thus, β-secretase inhibitors may be tested for their ability to decrease the hydrolysis of the β-secretase site of a substrate, such as the β-amyloid precursor protein, analogs of β-amyloid precursor protein, or fragments of β-amyloid precursor protein.

A "beta-secretase inhibitor" (i.e. β-secretase inhibitor) refers to a compound capable of reducing the proteolytic activity of memapsin-2 relative to the activity in the absence of inhibitor.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

β-Secretase Inhibitors

In one aspect, the present invention provides a β-secretase inhibitor compound having the formula:

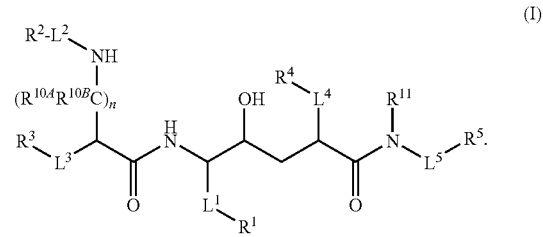

(I)

In Formula (I), n is an integer from 0 to 5 (e.g. 1 to 5).

$R^1$, $R^3$, $R^4$, $R^5$ are independently —$NR^{29}R^{30}$, —$OR^{31}$, —$C(O)R^{32}$, —$S(O)_tR^{32}$, —$N_3$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, amino acid side chain, or -$L^6$-Y. The symbol t represents an integer from 0 to 2.

$R^{29}$ is —$C(O)R^{33}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{32}$ is —$NR^{34}R^{35}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{34}$ is independently —$NR^{36}R^{37}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Where $R^1$, $R^3$, $R^4$, or $R^5$ is —$S(O)_tR^{32}$, then $R^{34}$ is not —$NR^{36}R^{37}$.

$R^{30}$, $R^{31}$, $R^{33}$, $R^{35}$, $R^{36}$, and $R^{37}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^{11}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^6$-Y.

$R^{10A}$ and $R^{10B}$ are independently selected from a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^6$Y. $R^{10A}$ is optionally joined with $R^2$ to form a substituted or unsubstituted cycloalkyl, substituted or unsubstituted heterocycloalkyl, substituted or unsubstituted aryl, or substituted or unsubstituted heteroaryl.

$L^2$ is a bond, —C(O)—, —O(CH$_2$)$_k$—, —C(O)NR$^6$—, —NH—, —C(O)O—, —S—, —S(O)—, —S(O)$_2$—, substituted or unsubstituted alkylene, or substituted or unsubstituted heteroalkylene. $R^6$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol "k" represents an integer from) to 5. In some embodiments, k is 0.

$L^3$ is a bond, —C(O)—, —O—, —C(O)NR$^7$—, —N(R$^7$)—, —C(O)O—, —S—, —S(O)—, —S(O)$_2$—, —NR$^7$—C(O)—NR$^8$—, —NR$^7$—C(O)—O—, substituted or unsubstituted alkylene, or substituted or unsubstituted heteroalkylene. In some embodiments, if $R^3$ is —NR$^{29}$R$^{30}$, the $L^3$ is not —S—, —S(O)—, —S(O)$_2$—, —NR$^7$—C(O)—NR$^8$—, or —NR$^7$—C(O)—O—. In some embodiments, if $R^3$ is OR$^{31}$, then $L^3$ is not —O—, —C(O)O—, —S—, —S(O)—, —S(O)$_2$—, —NR$^7$—C(O)—NR$^8$—, or —NR$^7$—C(O)—O—. In some embodiments, if $R^3$ is —C(O)R$^{32}$, —S(O)$_r$R$^{32}$, or —N$_3$, then $L_3$ is a bond substituted or unsubstituted alkylene, or substituted or unsubstituted heteroalkylene. $R^7$ and $R^8$ are, independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^5$ is a bond, —C(O)—, —C(O)NH—, substituted or unsubstituted alkylene, or substituted or unsubstituted heteroalkylene. In some embodiments, if $R^5$ is —C(O)R$^{32}$, —S(O)$_r$R$^{32}$, or —N$_3$, then $L^5$ is a bond or substituted or unsubstituted alkylene, or substituted or unsubstituted heteroalkylene. Y is a carrier moiety.

$L^6$ is selected from a bond, —OP(OH)$_2$O—, —C(O)OR$^{26}$—, —C(O)NHR$^{27}$—, —S(O)$_2$NHR$^{28}$—, substituted or unsubstituted alkylene, substituted or unsubstituted heteroalkylene, or a peptidyl linker. $R^{26}$, $R^{27}$, and $R^{28}$ are each independently selected from the following: substituted or unsubstituted alkyl, substituted or unsubstituted heteroalkyl, cycloalkyl, substituted or unsubstituted heterocycloalkyl, substituted or unsubstituted aryl, or substituted or unsubstituted heteroaryl.

In an exemplary embodiment, n is an integer from 0 to 2.

$R^1$ may be hydrogen, substituted or unsubstituted $C_1$-$C_{20}$ alkyl, substituted or unsubstituted 2 to 20 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted aryl, substituted or unsubstituted heteroaryl, or -$L^6$-Y. $R^1$ may also be substituted or unsubstituted $C_1$-$C_{20}$ alkyl, substituted or unsubstituted 2 to 20 membered heterocycloalkyl, substituted or unsubstituted aryl, or substituted or unsubstituted heteroaryl. Alternatively, $R^1$ is substituted or unsubstituted $C_1$-$C_{20}$ alkyl, substituted or unsubstituted aryl, or substituted or unsubstituted heteroaryl. In some embodiments, $R^1$ is substituted or unsubstituted aryl, substituted or unsubstituted heteroaryl, or substituted or unsubstituted $C_1$-$C_8$ alkyl. In other embodiments, $R^1$ is selected from unsubstituted aryl; unsubstituted heteroaryl; aryl substituted with a halogen; heteroaryl substituted with a halogen; or $C_1$-$C_{20}$ alkyl substituted with a halogen, unsubstituted aryl, aryl substituted with a halogen, unsubstituted heteroaryl, or heteroaryl substituted with a halogen. $R^1$ may be selected from $C_1$-$C_5$ alkyl substituted with a substituted or unsubstituted phenyl, or substituted or unsubstituted pyridinyl. $R^1$ may also be selected from $C_1$-$C_5$ alkyl substituted with unsubstituted phenyl; unsubstituted pyridinyl or phenyl substituted with a halogen, OR$^{1A}$, or unsubstituted ($C_1$-$C_5$) alkyl $R^{1A}$ may be hydrogen or unsubstituted ($C_1$-$C_5$) alkyl.

In another exemplary embodiment, $R^1$ is methyl substituted with an unsubstituted phenyl, unsubstituted pyridinyl, 3,5-difluorophenyl, 4-hydroxyphenyl, 3-chloro-4-hydroxyphenyl, or 3-chloro-4-methoxyphenyl. $R^1$ may also be —CH$_2$—CH(CH$_3$)—CH$_3$. In some embodiments, $R^1$ is an amino acid side chain.

$R^4$ may be hydrogen, substituted or unsubstituted $C_1$-$C_{20}$ (e.g. $C_1$-$C_{10}$) alkyl, substituted or unsubstituted 2 to 20 (e.g. 2 to 10) membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted aryl, substituted or unsubstituted heteroaryl, or -$L^6$-Y. $R^1$ may also be selected from substituted or unsubstituted $C_1$-$C_{20}$ alkyl, substituted or unsubstituted 2 to 20 membered heterocycloalkyl, substituted or unsubstituted aryl, or substituted or unsubstituted heteroaryl. In some embodiments, $R^4$ is substituted or unsubstituted $C_1$-$C_{20}$ alkyl, substituted or unsubstituted aryl, or substituted or unsubstituted heteroaryl. In other embodiments, $R^4$ is selected from substituted or unsubstituted aryl, substituted or unsubstituted heteroaryl, or substituted or unsubstituted $C_1$-$C_8$ alkyl.

Alternatively, $R^4$ is selected from unsubstituted aryl; unsubstituted heteroaryl; aryl substituted with a halogen; heteroaryl substituted with a halogen; or $C_1$-$C_{20}$ alkyl substituted with a halogen, unsubstituted aryl, aryl substituted with a halogen, unsubstituted heteroaryl, or heteroaryl substituted with a halogen. $R^4$ may also be methyl or ethyl. In some embodiments, $R^4$ is an amino acid side chain.

$L^2$ maybe a bond, —C(O)—, —O(CH$_2$)$_k$—, —C(O)NR$^6$—, —NH—, —C(O)O—, —S—, —S(O)—, —S(O)$_2$—, substituted or unsubstituted $C_1$-$C_{20}$ alkylene, or substituted or unsubstituted 2 to 20 membered heteroalkylene. $R^6$ may be a hydrogen, substituted or unsubstituted $C_1$-$C_{20}$ alkyl, substituted or unsubstituted 2 to 20 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted aryl, or substituted or unsubstituted heteroaryl. In some embodiments, $L^2$ is selected from a bond, —C(O)—, —C(O)NR$^6$—, —C(O)O—, —S(O)$_2$—, substituted or unsubstituted $C_1$-$C_{20}$ alkylene, or substituted or unsubstituted 2 to 20 membered heteroalkylene. In other embodiments, $L^2$ is —C(O)—, —C(O)NR$^6$—, —C(O)O—, or —S(O)$_2$—.

$R^6$ may be a hydrogen or substituted or unsubstituted $C_1$-$C_{20}$ alkyl. $R^6$ may also be hydrogen or unsubstituted $C_1$-$C_{20}$ alkyl. Alternatively, $R^6$ is selected from hydrogen or unsubstituted $C_1$-$C_4$ alkyl.

$R^2$ may be selected from substituted or unsubstituted $C_1$-$C_{20}$ alkyl, substituted or unsubstituted 2 to 20 membered heteroalkyl, substituted or unsubstituted $C_3$-$C_7$ cycloalkyl, substituted or unsubstituted 5 to 7 membered heterocycloalkyl, substituted or unsubstituted aryl, substituted or unsubstituted heteroaryl, or -$L^6$-Y. $R^2$ may also be substituted or unsubstituted $C_1$-$C_{20}$ alkyl, substituted or unsubstituted 2 to 20 membered heteroalkyl, substituted or unsubstituted aryl, or substituted or unsubstituted heteroaryl. Alternatively, $R^2$ is a unsubstituted aryl; aryl substituted with a halogen or unsubstituted $C_1$-$C_{10}$ alkyl; unsubstituted heteroaryl; heteroaryl substituted with a halogen or unsubstituted $C_1$-$C_{10}$ alkyl; or $C_1$-$C_{20}$ alkyl substituted with a halogen, unsubstituted aryl, aryl substituted with a halogen, unsubstituted heteroaryl, or heteroaryl substituted with a halogen. In some embodiments, $R^2$ is an unsubstituted $C_1$-$C_{20}$ alkyl, unsubstituted 2 to 20 membered heteroalkyl, substituted or unsubstituted aryl, or unsubstituted heteroaryl. In other embodiments, $R^1$ is an unsubstituted $C_1$-$C_4$ alkyl, unsubstituted furanyl, unsubstituted phenyl, unsubstituted pyridinyl, unsubstituted thiazolyl, furanyl substituted with a substituted or unsubstituted $C_1$-$C_{20}$ alkyl, phenyl substituted with a substituted or unsubstituted $C_1$-$C_{20}$ alkyl, pyridinyl substituted with substituted or unsubstituted $C_1$-$C_{20}$ alkyl, or thioazolyl substituted with substituted or unsubstituted $C_1$-$C_{20}$ alkyl.

Alternatively, $R^2$ is an unsubstituted $C_1$-$C_4$ alkyl, unsubstituted furanyl, unsubstituted phenyl, unsubstituted pyridinyl, furanyl substituted with an unsubstituted $C_1$-$C_{10}$ alkyl, phenyl substituted with an unsubstituted $C_1$-$C_{10}$ alkyl, pyridinyl substituted with an unsubstituted $C_1$-$C_{10}$ alkyl, or thiazolyl substituted with an unsubstituted $C_1$-$C_{10}$ alkyl. $R^2$ may also be selected from unsubstituted $C_1$-$C_4$ alkyl, unsubstituted furanyl, unsubstituted phenyl, unsubstituted pyridinyl, furanyl substituted with an unsubstituted $C_1$-$C_4$ alkyl, phenyl substituted with an unsubstituted $C_1$-$C_4$ alkyl, pyridinyl substituted with an unsubstituted $C_1$-$C_4$ alkyl, or thiazolyl substituted with an unsubstituted $C_1$-$C_4$ alkyl.

$L^3$ may be a bond, —C(O)—, —O—, —C(O)NR$^7$—, —N(R$^7$)—, —C(O)O—, —S—, —S(O)—, —S(O)$_2$—, —NR$^7$—C(O)—NR$^8$—, —NR$^7$—C(O)—O—, substituted or unsubstituted $C_1$-$C_{20}$ alkylene, or substituted or unsubstituted 2 to 20 membered heteroalkylene. $R^7$ and $R^8$ may be independently selected from hydrogen, substituted or unsubstituted $C_1$-$C_{20}$ alkyl, substituted or unsubstituted 2 to 20 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted aryl, or substituted or unsubstituted heteroaryl.

$L^3$ may also be selected from substituted or unsubstituted alkylene, or substituted or unsubstituted heteroalkylene. Alternatively, $L^3$ may be selected from substituted or unsubstituted $C_1$-$C_{20}$ alkylene, or substituted or unsubstituted 2 to 20 membered heteroalkylene. In some embodiments, $L^3$ is a $C_1$-$C_{20}$ alkylene substituted with an oxo, or unsubstituted $C_1$-$C_{20}$ alkyl; or 2 to 20 membered heteroalkylene substituted with an oxo, or unsubstituted $C_1$-$C_{20}$ alkyl.

In an exemplary embodiment, -$L^3$-$R^3$ of Formula (I) has the formula:

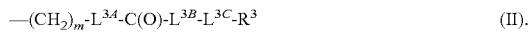

—(CH$_2$)$_m$-L$^{3A}$-C(O)-L$^{3B}$-L$^{3C}$-R$^3$ (II).

In Formula (II), the symbol "m" is an integer from 0 to 10. $L^{3A}$ is selected from a bond, —N(R$^{12}$)—, —O—, or —C(R$^{13}$)(R$^{14}$)—. $R^{12}$ is a hydrogen, or unsubstituted $C_1$-$C_{20}$ alkyl. $R^{13}$ and $R^{14}$ may independently be selected from hydrogen, unsubstituted $C_1$-$C_{20}$ alkyl, —OR$^{15}$, or —N$^6$R$^{17}$. $R^{15}$, $R^{16}$ and $R^{17}$ are, independently, hydrogen or unsubstituted $C_1$-$C_{20}$ alkyl.

$L^{3B}$ is a bond, —N(R$^{18}$)—, —C(R$^{19}$)(R$^{20}$)—, or —O—. $R^{18}$ may be selected from hydrogen, or unsubstituted $C_1$-$C_{20}$ alkyl. $R^{19}$ and $R^{20}$ are independently hydrogen, unsubstituted $C_1$-$C_{20}$ alkyl, —OR$^{21}$, or —NR$^2$R$^3$, $C_1$-$C_{20}$ alkyl substituted with —OR$^{21}$, or N$_3$. $R^{21}$, $R^{22}$ and $R^{23}$ are independently hydrogen, or unsubstituted $C_1$-$C_{20}$ alkyl. $L^{3C}$ is a bond, unsubstituted $C_1$-$C_{20}$ alkylene, or unsubstituted 2 to 20 membered heteroalkylene.

In some embodiments, m is an integer from 1 to 10, one of $R^{13}$ or $R^{14}$ is hydrogen, one of $R^{19}$ or $R^{20}$ is hydrogen, or $L^{3C}$ is $C_1$-$C_{20}$ alkylene.

In some embodiments, $R^3$ is a substituted or unsubstituted cycloalkyl, substituted or unsubstituted heterocycloalkyl, substituted or unsubstituted aryl, or substituted or unsubstituted heteroaryl. The symbol m may be 0. $L^{3A}$ may be —N(R$^{12}$)—. $L^{3B}$ may be —C(R$^{19}$)(R$^{20}$)—. $L^{3C}$ may be unsubstituted $C_1$-$C_5$ alkylene. $R^{12}$ may be hydrogen. $R^{19}$ may be hydrogen. $L^{3C}$ may be methylene.

In other embodiments, $R^3$ is a substituted or unsubstituted cycloalkyl, substituted or unsubstituted heterocycloalkyl, substituted or unsubstituted aryl, or substituted or unsubstituted heteroaryl. The symbol m may be 1. $L^{3B}$ may be —N(R$^{18}$)—. $L^{3C}$ may be unsubstituted $C_1$-$C_5$ alkylene. $R^{18}$ may be hydrogen. $L^{3C}$ may be methylene.

In an exemplary embodiment, the symbol "m" is 0. $R^{12}$, $R^{13}$, $R^{14}$, and $R^{19}$ may be hydrogen. $R^{18}$ may hydrogen or unsubstituted $C_1$-$C_{20}$ alkyl. $R^{20}$ may be hydrogen, unsubstituted $C_1$-$C_8$ alkyl, —OR$^{21}$, or —N$^{22}$R$^{23}$. $R^{21}$, $R^{22}$, and $R^{23}$, independently, may be hydrogen, or unsubstituted $C_1$-$C_8$ alkyl. $L^{3C}$ may be an unsubstituted $C_1$-$C_8$ alkylene.

In some embodiments, -$L^3$-$R^3$ may also be selected from: —NH—C(O)—CHR$^{19}$—CH$_2$—R$^3$; —NH—C(O)—O—CH$_2$—R$^3$; —NH—C(O)—NH—CH$_2$—R$^3$; —CH$_2$—C(O)—NH—CH$_2$—R$^3$; —CH$_2$—C(O)—CHR$^{19}$—CH$_2$—R$^3$; —CH$_2$—C(O)—O—CH$_2$—R$^3$; or —O—C(O)—NH—CH$_2$—R$^3$. $R^{15}$ is hydrogen or unsubstituted $C_1$-$C_{20}$ alkyl.

In an exemplary embodiment, $R^3$ is selected from substituted or unsubstituted $C_1$-$C_{20}$ alkyl, substituted or unsubstituted 2 to 20 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted aryl, substituted or unsubstituted heteroaryl, or -L$^6$-Y. $R^3$ may also be selected from substituted or unsubstituted aryl, substituted or unsubstituted heteroaryl, or substituted or unsubstituted heterocycloalkyl. Alternatively, $R^3$ is a substituted or unsubstituted 5 membered heteroaryl, or substituted or unsubstituted 5 membered heterocycloalkyl.

In some embodiments, $R^3$ is selected from an unsubstituted heteroaryl; an unsubstituted heterocycloalkyl; a heteroaryl substituted with halogen, —CF$_3$, —OH, —NH$_2$, —CN, unsubstituted $C_1$-$C_{20}$ alkyl, or unsubstituted 2 to 20 membered heteroalkyl; or heterocycloalkyl substituted with oxo, or unsubstituted $C_1$-$C_{20}$ alkyl. In other embodiments, $R^3$ is an unsubstituted aryl; unsubstituted heteroaryl; aryl substituted with a halogen; heteroaryl substituted with a halogen; or $C_1$-$C_{20}$ alkyl substituted with a halogen, unsubstituted aryl, aryl substituted with a halogen, unsubstituted heteroaryl, or heteroaryl substituted with a halogen.

In another exemplary embodiment, $R^3$ is selected from a substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisoxazolyl, or substituted or unsubstituted dimethylhydantoin.

In some exemplary embodiments, $R^3$ is substituted or unsubstituted pyrazolyl, substituted or unsubstituted oxazolyl, substituted or unsubstituted thiazolyl, or substituted or unsubstituted furanyl. In other exemplary embodiments, $R^3$ is selected from a substituted or unsubstituted 1-pyrazolyl, substituted or unsubstituted 4-oxazolyl, substituted or unsubstituted 2-oxazolyl, substituted or unsubstituted 2-thiazolyl, or substituted or unsubstituted 2-furanyl.

$R^3$ may also be selected from a 1-pyrazolyl substituted with an unsubstituted $C_1$-$C_{20}$ alkyl, or unsubstituted 2 to 20 membered heteroalkyl; 4-oxazolyl substituted with an unsubstituted $C_1$-$C_{20}$ alkyl, or unsubstituted 2 to 20 membered heteroalkyl; 2-oxazolyl substituted with an unsubstituted $C_1$-$C_{20}$ alkyl, or unsubstituted 2 to 20 membered heteroalkyl; 2-thiazolyl substituted with an unsubstituted $C_1$-$C_{20}$ alkyl, or unsubstituted 2 to 20 membered heteroalkyl; or 2-furanyl substituted with an unsubstituted $C_1$-$C_{20}$ alkyl, or unsubstituted 2 to 20 membered heteroalkyl.

Alternatively, $R^3$ may be one of the following: 1-pyrazolyl substituted with an unsubstituted $C_1$-$C_5$ alkyl, or unsubstituted 2 to 6 membered heteroalkyl; 4-oxazolyl substituted with an unsubstituted $C_1$-$C_5$ alkyl, or unsubstituted 2 to 6 membered heteroalkyl; 2-oxazolyl substituted with an unsubstituted $C_1$-$C_5$ alkyl, or unsubstituted 2 to 6 membered heteroalkyl; 2-thiazolyl substituted with an unsubstituted $C_1$-$C_5$ alkyl, or unsubstituted 2 to 6 membered heteroalkyl; or 2-furanyl substituted with an unsubstituted $C_1$-$C_5$ alkyl, or unsubstituted 2 to 6 membered heteroalkyl.

$R^3$ may also be one of: 1-pyrazolyl substituted with an unsubstituted $C_1$-$C_5$ alkyl (e.g. at the 3 position, the 5 position, or the 3 and 5 position); 4-oxazolyl substituted with an unsubstituted $C_1$-$C_5$ alkyl (e.g. at the 2 position, the 5-position, or the 2 and 5 position); 2-oxazolyl substituted with an unsubstituted $C_1$-$C_5$ alkyl (e.g. at the 4 position); 2-thiazolyl substituted with an unsubstituted $C_1$-$C_5$ alkyl (e.g. at the 4 position); or 2-furanyl substituted with an unsubstituted $C_1$-$C_5$ alkyl (e.g. at the 5 position).

In an exemplary embodiment, $L^5$ is a bond, —C(O)—, substituted or unsubstituted $C_1$-$C_{20}$ alkylene, or substituted or unsubstituted 2 to 20 membered heteroalkylene. $L^5$ may be selected from a bond, —C(O)—, substituted or unsubstituted $C_1$-$C_{20}$ alkylene, or substituted or unsubstituted 2 to 10 membered heteroalkylene. $L^5$ may also be selected from a bond; unsubstituted $C_1$-$C_{10}$ alkylene; unsubstituted 2 to 10 membered heteroalkylene; $C_1$-$C_{10}$ alkylene substituted with an oxo, unsubstituted $C_1$-$C_{10}$ alkyl, or unsubstituted 2 to 10 membered heteroalkyl; or 2 to 10 membered heteroalkylene substituted with an oxo, unsubstituted $C_1$-$C_{10}$ alkyl, or unsubstituted 2 to 10 membered heteroalkyl.

In another exemplary embodiment, -$L^5$-$R^5$ has the formula

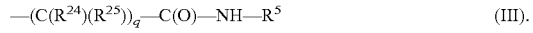

$$—(C(R^{24})(R^{25}))_q—C(O)—NH—R^5 \qquad (III).$$

The symbol "q" is an integer from 0 to 5. $R^{24}$ and $R^{25}$ are independently selected from a hydrogen, substituted or unsubstituted $C_1$-$C_{10}$ alkyl, substituted or unsubstituted 2 to 10 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, or substituted or unsubstituted aryl, or substituted or unsubstituted heteroaryl. $R^5$ may be selected from substituted or unsubstituted $C_1$-$C_{20}$ alkyl, substituted or unsubstituted 2 to 20 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted 2 to 20 membered heterocycloalkyl, substituted or unsubstituted aryl, substituted or unsubstituted heteroaryl, or -$L^6$-Y. In some embodiments, one of $R^{24}$ or $R^{25}$ is hydrogen.

In some embodiments, $R^5$ is —$N^{29}R^{30}$. $R^{24}$, $R^{25}$, $R^{29}$, and $R^{30}$ may independently be selected from hydrogen and substituted or unsubstituted $C_1$-$C_{10}$ alkyl. The symbol q may be 1 or 2. $R^{25}$, $R^{29}$, and $R^{30}$ may also independently be unsubstituted $C_1$-$C_5$ alkyl. $R^{24}$ may also be hydrogen.

In some embodiments, $R^5$ is —$S(O)_tR^{32}$. The symbol t may represent 2. $R^{32}$ may be substituted or unsubstituted $C_1$-$C_{10}$ alkyl. $L^5$ may be substituted or unsubstituted $C_1$-$C_{10}$ alkylene. $R^{32}$ may also be unsubstituted $C_1$-$C_5$ alkyl. $L^5$ may also be unsubstituted $C_1$-$C_5$ alkylene.

In an exemplary embodiment, $R^{24}$ is hydrogen. $R^{25}$ may be selected from an unsubstituted $C_1$-$C_{10}$ alkyl, unsubstituted $C_3$ to $C_7$ (e.g. $C_5$ to $C_7$) cycloalkyl, unsubstituted aryl, $C_5$ to $C_7$ cycloalkyl substituted with a $C_1$-$C_5$ unsubstituted alkyl, or aryl substituted with a $C_1$-$C_5$ unsubstituted alkyl.

$R^5$ may be selected from a substituted or unsubstituted $C_1$-$C_{10}$ alkyl, substituted or unsubstituted 2 to 10 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heteroalkyl, substituted or unsubstituted 2 to 10 membered heterocycloalkyl, substituted or unsubstituted aryl, substituted or unsubstituted heteroaryl, or -$L^6$-Y. Alternatively, $R^5$ is selected from unsubstituted aryl; unsubstituted heteroaryl; aryl substituted with a halogen; heteroaryl substituted with a halogen; or $C_1$-$C_{20}$ alkyl substituted with a halogen.

In some exemplary embodiments, $R^5$ is an unsubstituted $C_1$-$C_{10}$ alkyl; unsubstituted 2 to 10 membered heteroalkyl; unsubstituted $C_3$-$C_7$ (e.g. $C_5$-$C_7$) cycloalkyl, substituted or unsubstituted 3 to 7 (e.g. 5 to 7) membered heteroalkyl; unsubstituted 2 to 10 membered heterocycloalkyl; unsubstituted aryl; unsubstituted heteroaryl; $C_1$-$C_{10}$ alkyl substituted with an —OH, —COOH, halogen, unsubstituted $C_1$-$C_8$ alkyl, or unsubstituted 2 to 5 membered heteroalkyl; 2 to 10 membered heteroalkyl substituted with an —OH, —COOH, halogen, unsubstituted $C_1$-$C_5$ alkyl, or unsubstituted 2 to 5 membered heteroalkyl; $C_5$-$C_7$ cycloalkyl substituted with an —OH, —COOH, halogen, unsubstituted $C_1$-$C_5$ alkyl, or unsubstituted 2 to 5 membered heteroalkyl; 5 to 7 membered heterocycloalkyl substituted with an —OH, —COOH, halogen, unsubstituted $C_1$-$C_5$ alkyl, or unsubstituted 2 to 5 membered heteroalkyl; aryl substituted with an —OH, —COOH, halogen, unsubstituted $C_1$-$C_5$ alkyl, or unsubstituted 2 to 5 membered heteroalkyl; or heteroaryl substituted with an —OH, —COOH, halogen, unsubstituted $C_1$-$C_5$ alkyl, or unsubstituted 2 to 5 membered heteroalkyl.

In other exemplary embodiments, $R^5$ is an unsubstituted $C_1$-$C_{10}$ alkyl; or heteroaryl substituted with an —OH, —COOH, halogen, unsubstituted $C_1$-$C_5$ alkyl, or unsubstituted 2 to 5 membered heteroalkyl. $R^5$ may also be selected from unsubstituted $C_1$-$C_5$ alkyl; unsubstituted pyridinyl; or pyridinyl substituted with an unsubstituted $C_1$-$C_5$ alkyl.

$R^{11}$ may be a hydrogen, substituted or unsubstituted alkyl, or substituted or unsubstituted heteroalkyl. $R^{11}$ may also be a hydrogen, unsubstituted $C_1$-$C_{20}$ alkyl, unsubstituted 2 to 20 membered heteroalkyl, $C_1$-$C_{20}$ alkyl substituted with a halogen, or 2 to 20 membered heteroalkyl substituted with a halogen. In another exemplary embodiment, $R^{11}$ is a hydrogen, unsubstituted $C_1$-$C_{20}$ alkyl, unsubstituted 2 to 20 membered heteroalkyl, $C_1$-$C_{20}$ alkyl substituted with a fluorine or chlorine, or 2 to 20 membered heteroalkyl substituted with a fluorine or chlorine.

$R^{10A}$ and $R^{10B}$ may be independently selected from a hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 5 to 7 membered heterocycloalkyl, substituted or unsubstituted aryl, substituted or unsubstituted heteroaryl, or -$L^6$Y. $R^{10A}$ and $R^{10B}$ may also be independently selected from a hydrogen, substituted or unsubstituted $C_1$-$C_8$ alkyl, substituted or unsubstituted 2 to 8 membered heteroalkyl, substituted or unsubstituted $C_3$-$C_7$ (e.g. $C_5$-$C_7$) cycloalkyl, substituted or unsubstituted 3 to 7 (e.g. 5 to 7) membered heterocycloalkyl, substituted or unsubstituted aryl, substituted or unsubstituted heteroaryl, or -$L^6$Y.

In another exemplary embodiment, $R^{10A}$ and $R^{10B}$ are independently selected from a hydrogen, unsubstituted $C_1$-$C_8$ alkyl, unsubstituted 2 to 8 membered heteroalkyl, unsubstituted $C_5$-$C_7$ cycloalkyl, unsubstituted 5 to 7 membered heterocycloalkyl, unsubstituted aryl, or unsubstituted heteroaryl.

$R^{10A}$ is optionally joined with $R^2$ to form a substituted or unsubstituted cycloalkyl, substituted or unsubstituted heterocycloalkyl, substituted or unsubstituted aryl, or substituted or unsubstituted heteroaryl. In an exemplary embodiment, $R^{10A}$ is optionally joined with $R^2$ to form a substituted or unsubstituted $C_3$-$C_8$ cycloalkyl, substituted or unsubstituted 5 to 6 membered heterocycloalkyl, substituted or unsubstituted aryl, or substituted or unsubstituted heteroaryl. In another exemplary embodiment, $R^{10A}$ is optionally joined with $R^2$ to form an unsubstituted $C_3$-$C_8$ cycloalkyl, unsubstituted 5 to 6 membered heterocycloalkyl, unsubstituted aryl, or unsubstituted heteroaryl.

In some embodiments, $R^{36}$ and $R^{37}$ are hydrogen or substituted or unsubstituted $C_1$-$C_{10}$ alkyl. $R^{36}$ and $R^{37}$ may also be hydrogen or unsubstituted $C_1$-$C_5$ alkyl.

$L^6$ may be selected from a bond, —OP(OH)$_2$O—, —C(O) OR$^{26}$—, —C(O)NHR$^{27}$—, —S(O)$_2$NHR$^{28}$—, substituted or unsubstituted $C_1$-$C_{20}$ alkylene, substituted or unsubstituted 2 to 20 membered heteroalkylene, substituted or unsubstituted 3-8 membered cycloalkylene, substituted or unsubstituted 3 to 8 membered heterocycloalkylene, substituted or unsubstituted arylene, substituted or unsubstituted heteroarylene, or peptidyl linker. $R^{26}$, $R^{27}$, and $R^{28}$ may independently be selected from substituted or unsubstituted $C_1$-$C_{20}$ alkyl, substituted or unsubstituted 2 to 20 membered heteroalkyl, substituted or unsubstituted 3-8 membered cycloalkyl, substituted or unsubstituted 3 to 8 membered heterocycloalkyl, substituted or unsubstituted aryl, or substituted or unsubstituted heteroaryl.

In an exemplary embodiment, 0, 1, 2 or 3 of $R^1$, $R^2$, $R^3$, $R^4$, $R^5$, $R^{10A}$, $R^{10B}$, and $R^{11}$ may be -$L^6$-Y. In some exemplary embodiments, 0 or 1 of $R^1$, $R^2$, $R^3$, $R^4$, $R^5$, $R^{10A}$, $R^{10B}$, and $R^{11}$ may be -$L^6$-Y. In other exemplary embodiments, $R^1$, $R^2$, $R^3$, $R^4$, $R^5$, $R^{10A}$, $R^{10B}$, and $R^{11}$ may not be -$L^6$-Y.

Y may be a peptidyl carrier moiety. The peptidyl carrier moiety may be capable of transporting the compound of Formula (I) across the blood brain barrier of a mammal. Alternatively, the peptidyl carrier moiety may be capable of binding to a blood brain barrier receptor. The peptidyl carrier moiety may also be derived from an HIV tat protein, a peptide comprising an oligo-D-arginine residue, an antibody, or an antibody fragment. Carrier moieties are described in detail below.

In some embodiments, the inhibitors of the present invention have a stereochemical configuration as shown below in Formula (IV).

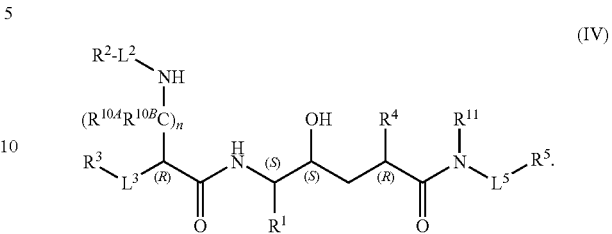

(IV)

In Formula (IV), $L^2$, $L^3$, $L^5$, $R^1$, $R^2$, $R^3$, $R^4$, $R^5$, $R^{11}$, $R^{10A}$, $R^{10B}$, and n are as defined above in the discussion of the compounds of Formula (I).

As described above, -$L^3$-$R^3$ is —CH$_2$—C(O)—CHR$^{19}$—CH$_2$—$R^3$. In some embodiments, the stereochemical configuration is as shown below in Formula V:

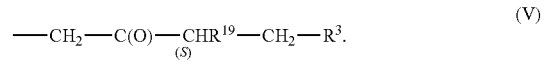

(V)

In Formula (V), $R^3$ and $R^{19}$ are as defined above in the discussion of -$L^3$-$R^3$ and the compounds of Formula (I).

In some embodiments, each substituted group described above in the compounds of Formulae (I)-(V) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted, substituted heteroalkylene, substituted arylene, and/or substituted heteroarylene described above in the compounds of Formulae (I)-(VIII) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I)-(V), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ (e.g. $C_5$-$C_7$) cycloalkyl, each substituted or unsubstituted heterocycloalkyl is a substituted or unsubstituted 3 to 7

(e.g. 5 to 7) membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

In another embodiment, the compounds of the present invention include any of the compounds Table 1.

Carrier Moieties

In copending U.S. Application No. 20040121947, and International Application No. PCT/US02/34324 (Publication No. WO 03/039454), which are herein incorporated by reference for all purposes, isostere β-secretase inhibitors with and without a carrier moiety were shown to effectively reduce Aβ production in tg2576 mice expressing the Swedish mutation of the human amyloid precursor protein (Hsiao, K., et al., Science 274, 99-102 (1996)). Thus, one of skill in the art will recognize that the compounds of the invention may be administered with or without a carrier moiety.

A "carrier moiety," as used herein, refers to a chemical moiety covalently or non-covalently attached to a β-secretase inhibitor compound of the invention that enhances the ability of the compound to traverse the blood-brain barrier (BBB). The β-secretase inhibitors of the invention may be attached or conjugated to the carrier moiety by covalent interactions (e.g., peptide bonds) or by non-covalent interactions (e.g., ionic bonds, hydrogen bonds, van der Waals attractions).

The blood-brain barrier is a permeability barrier that exists between the extracellular fluid in the brain and the blood in the capillary lumen. The barrier stems from structural differences between the capillaries in the brain and capillaries found in other tissues. Most significant among the structural differences of brain capillaries are the tight junctions between endothelial cells. These specialized tight junctions create a very high trans-endothelial electrical resistance of 1500-2000 ohms/cm$^2$ compared to 3-33 ohms/cm$^2$ in capillary endothelial cells lying outside the brain, reducing the aqueous based para-cellular diffusion observed in other organs (Brightman, M. in Bradbury M W B (ed) *Physiology and Pharmacology of the blood-brain barrier. Handbook of experimental pharmacology* 103, Springer-Verlag, Berlin, (1992); Lo, E. H., et al., *Brain Res. Rev.*, 38:140-148, (2001)). Thus, in some embodiments, the compounds of the present invention are covalently attached to a carrier moiety (represented by the symbol Y in the formulae above).

Any appropriate carrier moiety may be used in the present invention. Useful carrier moieties include, for example, lipophilic carrier moieties, enzymatic substrate carrier moieties, peptidyl carrier moieties, and nanoparticle carrier moieties. Carrier moieties may also include an oligosaccharide unit or other molecule linked to the compound by phosphoester or lipid-ester or other hydrolyzable bonds which are cleaved by glycosidases, phosphatases, esterases, lipases, or other hydrolases in the lysosomes and endosomes. The carrier moieties may contain guanidine, amino, or imidizole functional groups.

Lipophilic Carrier Moieties

Lipophilic carrier moieties increase the overall lipophilicity of a compound, thereby aiding in passage through the BBB. Lipophilicity can be quantified using any suitable approach known in the art. For example, the partition coefficient between octanol and water (log $P_{o/w}$) may be measured thereby indicating the degree of lipophilicity. In some embodiments, the lipophilic carrier moiety has a log $P_{o/w}$ of 1.5-2.5. Lipophilic carrier moieties are widely known in the art and are discussed in detail, for example, in Lambert, D. M., *Eur J Pharm Sci.*, 11:S15-27 (2000). Exemplary lipophilic carrier moieties used to increase the lipophilicity of a compound include modified and unmodified diglycerides, fatty acids, and phospholipids.

Some lipophilic carrier moieties undergo enzyme mediated oxidation after traversing the BBB, resulting in a hydrophilic membrane impermeable form of the carrier moiety that remains trapped behind the BBB (Bodor et al., *Pharmacol Ther* 76:1-27 (1997); Bodor et al., *American Chemical Society*, Washington, D.C. pp 317-337 (1995); Chen et al., *J Med Chem* 41:3773-3781 (1998); Wu et al., *J Pharm Pharmacol* 54:945-950 (2002)). Exemplary lipophilic carrier moieties that undergo enzyme mediated oxidation include 1,4-dihydrotrigonelline (Palomino et al., *J Med Chem*, 32:622-625 (1989)); alkyl phosphonate carrier moieties that have been successfully used to transport testosterone and zidovudine across the blood-brain barrier (Somogyi, G., et al., *Int J Pharm*, 166:15-26 (1998)); and the lipophilic dihydropyridine carrier moieties that are enzymatically oxidized to the ionic pyridinium salt (Bodor et al., *Science*, 214(18):1370-1372 (1981)).

Peptidyl Carrier Moieties

Peptidyl carrier moieties are moieties partially or wholly composed of a peptide (including polypeptides, proteins, antibodies, and antibody fragments) used to aid in the transport of compounds across the BBB (Wu et al., *J Clin Invest* 100:1804-1812 (1997); U.S. Pat. No. 4,801,575; Pardridge et al., *Adv Drug Deliv Rev*, 36:299-321 (1999)).

Peptidyl carrier moieties may interact with specific peptide transport systems, receptors, or ligands, that target the corresponding ligand or receptor on an endothelial cell of the BBB. Specific transport systems may include either carrier-mediated or receptor-mediated transport across the BBB (U.S. Pat. App. No. 20040110928). Exemplary peptidyl carrier moieties include insulin (Pardridge et al., *Nat Rev Drug Discov*, 1:131-139 (2002)); small peptides such as enkephalin, thyrotropin-releasing hormone, arginine-vassopressin (Bergley, *J Pharm Pharmacol*, 48:136-146 (1996)), Banks et al., *Peptides*, 13:1289-1294 (1992)), Han et al., *AAPS Pharm. Si.*, 2:E6 (2000)); chimeric peptides such as those described in WO-A-89/10134; amino acid derivatives such as those disclosed in U.S. Pat. App. No. 20030216589; tat peptide (Schwarze, S. R., et al., *Science* 285:1569-1572 (1999); polyarginine peptide (Wender, P. A., et al., *Proc. Natl. Acad. Sci. USA* 97:13003-13008 (2000)); insulin-like-growth factor-1; insulin-like-growth factor-2; transferrin; leptin; low-density lipoprotein (Pardridge, *Nat. Rev. Drug Discov.* 1:131-139 (2002); Colma et al., *Pharm. Res.* 17:266-274 (2000); Pardridge, *Endocrine Rev*, 7:314-330 (1986); Golden, et al., *J Clin Invest*, 99:14-18 (1997); Bickel et al., *Adv. Drug Deliv. Rev.* 46(1-3):247-79 (2001)); and basic fibroblast growth factor (bFGF) (U.S. Pat. App. No. 20040102369).

Copending U.S. Application No. 20040121947, and International Application No. PCT/US02/34324 (Publication No. WO 03/039454), disclose that confocal microscopic images of cells incubated with a fluorescent tat-conjugated isosteric β-secretase inhibitor showed uneven distribution inside cells. Some high fluorescence intensity was associated with the endosome and lysosome intracellular vesicular structures. This indicated that the tat carrier moiety may have been modified by proteases within the lysosome or endosome resulting in an inhibitor that was unable to exit the lysosomal or endosomal compartment. Lysosomes and endosomes contain many proteases, including hydrolase such as cathepsins A, B, C, D, H and L. Some of these are endopeptidase, such as cathepsins D and H. Others are exopeptidases, such as cathepsins A and C, with cathepsin B capable of both endo- and exopeptidase activity. The specificities of these proteases are sufficiently broad to hydrolyze a tat peptide away from the inhibitor compound, thus, hydrolyzing the carrier peptide away from the isosteric inhibitor. Thus, it has been shown that tat and other carrier peptides may be particularly useful for specific delivery of isosteric inhibitors to lysosomes and endosomes. When administered to a mammal by a mechanism such as injections, the conjugated compound will penetrate cells and permeate to the interior of lysosomes and endosomes. The proteases in lysosomes and endosomes will then hydrolyze tat, thereby preventing to escape from lysosomes and endosomes.

The carrier peptide may be tat or other basic peptides, such as oligo-L-arginine, that are hydrolyzable by lysosomal and endosomal proteases. Specific peptide bonds susceptible for the cleavage of lysosomal or endosomal proteases may be installed, thereby facilitating the removal of the carrier compound from the inhibitor. For example, dipeptides Phe-Phe, Phe-Leu, Phe-Tyr and others are cleaved by cathepsin D.

In one embodiment, the peptidyl carrier molecule includes cationic functional groups, such as the tat-peptide (Schwarze, S. R., et al., *Science* 285: 1569-1572 (1999)), or nine arginine residues (Wender, P. A., et al., *Proc. Natl. Acad. Sci. USA* 97:13003-13008 (2000)). Useful cationic functional groups include, for example, guanidine, amino, and imidazole functional groups. Thus, cationic functional groups also include amino acid side chains such as side chains of lysine, arginine, and histidine residues. In some embodiments, the peptidyl carrier molecule may includes from 1-10 cationic functional groups. When a compound of the invention is conjugated or attached to a carrier moiety, the resulting conjugate may be referred to herein as a "Carrier Peptide-Inhibitor" conjugate or "CPI." The CPI conjugate can be administered to an in vitro sample or to a mammal thereby serving as a transport vehicle for a compound or compounds of the invention into a cell in an in vitro sample or in a mammal. The carrier moieties and CPI conjugates result in an increase in the ability of the compounds of the invention to effectively penetrate cells and the blood brain barrier to inhibit memapsin 2 from cleaving APP to subsequently generate Aβ.

Adsorptive-meditated transcytosis (AME) provides an alternative mechanism whereby peptidyl carrier moieties may cross the BBB. AME differs from other forms of transcytosis in that the initial binding of the carrier moiety to the luminal plasma membrane is mediated through either electrostatic interactions with anionic sites, or specific interactions with sugar residues. Uptake through AME is determined by the C-terminal structure and basicity of the carrier moiety. Exemplary adsorptive peptidyl carrier moieties include peptides and proteins with basic isoeletric points (cationic proteins), and some lectins (glycoprotein binding proteins). See Tamai, I., et al., J. Pharmacol. Exp. Ther. 280:410-415 (1997); Kumagai, A. K., et al., *J. Biol. Chem.* 262: 15214-15219 (1987).

Peptidyl carrier moieties also include antibody carrier moieties. Antibody carrier moieties are carrier moieties that include an antibody or fragment thereof. Typically, the antibody or antibody fragment is, or is derived from, a monoclonal antibody. Antibody carrier moieties bind to cellular receptors, or transporters expressed on the luminal surface of brain capillary endothelial cells (U.S. Patent App No. 20040101904). Exemplary antibodies, or fragments thereof, include MAb 83-14 that binds to the human insulin receptor (Pardridge et al., *Pharm Res.* 12:807-816 (1995)); anti-transferrin antibody (Li, J. Y., et al., *Protein Engineering* 12:787-796 (1999)); and monoclonal antibodies that mimic an endogenous protein or peptide which is known to cross the BBB as discussed above.

Nanoparticle Carrier Moieties

Nanoparticle carrier moieties are solid colloidal carriers generally less than a micron in diameter or length. The compound may be encapsulated in, adsorbed onto, or covalently linked to the surface of the nanoparticle carrier moiety. Nanoparticle carrier moieties have been used to successfully deliver a variety of compounds to the brain, including hexapeptide dalagrin, an enkephalin analog; loperamide; tubocerarine; and doxorubicin (Ambikanandan, et al., *J. Pharm Pharmaceut Sci* 6(2):252-273 (2003)). In addition to aiding transport into the brain, nonionic detergents such as polysorbate-80, which can be used to coat the nanoparticle, may be used to inhibit the efflux pump. Zordan-Nudo, T., et al., *Cancer Res,* 53:5994-6000 (1993). Exemplary materials for the manufacture of nanoparticle carrier moieties include polyalkylcyanoacrylate (PACA) (Bertling et al., *Biotechnol. Appl. Biochem.* 13: 390-405 (1991)); polybutylcyanoacrylate (PBCA) (Chavany et al., *Pharm. Res.* 9: 441-449 (1992)); polybutylcyanoacrylate with the peptide-drug complex absorbed onto the surface and coated with polysorbate 80 (Kreuter, J., et al., *Brain Res,* 674:171-174 (1995), Kreuter, J., *Adv Drug Deliv Rev,* 47:65-81, (2001), Kreuter, J., *Curr Med Chem,* 2:241-249 (2002)); polyisohexylcyanoacrylate (PI-HCA) (Chavany et al., *Pharm. Res.* 11: 1370-1378 (1994)); polyhexylcyanoacrylate (PHCA) (Zobel et al., *Antisense Nucleic Acid Drug Dev.* 7:483-493 (1997)); and PEGylated polycyanoacrylate (Pilar, C., et al., *Pharm Res* 18(8): 1157-1166 (2001)).

Linker Moieties

Linker moieties may be used to attach the carrier moiety to the β-secretase inhibitors of the present invention (represented by the symbol $L^6$). For example, steric hinderance between the compound and the carrier can be prevented using polymer technology (e.g. PEGylation) in conjunction with the linker molecule to introduce a long spacer arm (Yoshikawa, T., et al., *J Pharmacol Exp Ther,* 263:897-903, 1992). Linker moieties may be cleavable or non-cleavable.

Cleavable linker molecules include a cleavable moiety. Any appropriate cleavable moiety is useful in the present invention, including for example, phosphoesters, esters, disulfides, and the like. Cleavable moieties also include those moieties capable of being cleaved by biological enzymes, such as peptidases, glycosidases, phosphatases, esterases, lipases, or other hydrolases. Cleavable linker molecules are especially useful where the carrier moiety interferes with the biological activity of the compound. Exemplary cleavable linker molecules include N-succinimidyl-3-2-pyridyldithiopropionate (SPDP), or N-hydrosuccinimide (NHS).

Non-cleavable linker molecules are those that involve the attachment of a carrier moiety to the compound through a linkage that is generally stable to biological conditions and enzymes. Non-cleavable linker molecules are typically used when the carrier moiety does not interfere with the biological activity of the compound. Exemplary non-cleavable linker molecules include thio-ether (e.g., m-maleimidobenzoyl N-hydroxysuccinimide ester (MBS)); amide (e.g., N-hydrosuccinimide (NHS-XX-); extended amide (e.g., N-hydrosuccinimide polyethylene glycol (NHS-PEG); and extended hydrazide linkages (e.g., hydrazide-PEG-biotin-); avidin-biotin; and PEG linkers (Ambikanandan et al., *J. Pharm Pharmaceut Sci* 6(2):252-273 (2003); Pardridge, *Adv Drug Deliv Rev,* 36:299-321 (1999); U.S. Pat. No. 6,287,792).

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

the protected isostere fragment 4s. Amide coupling of the 4s ester and 5s free amine yields the corresponding N-terminal extended isostere 6s. Acid deprotection of the 6s Boc amino group followed by amide coupling to the 7s ester yields the amino isostere 8s.

Beta-Secretase Inhibitor Activity

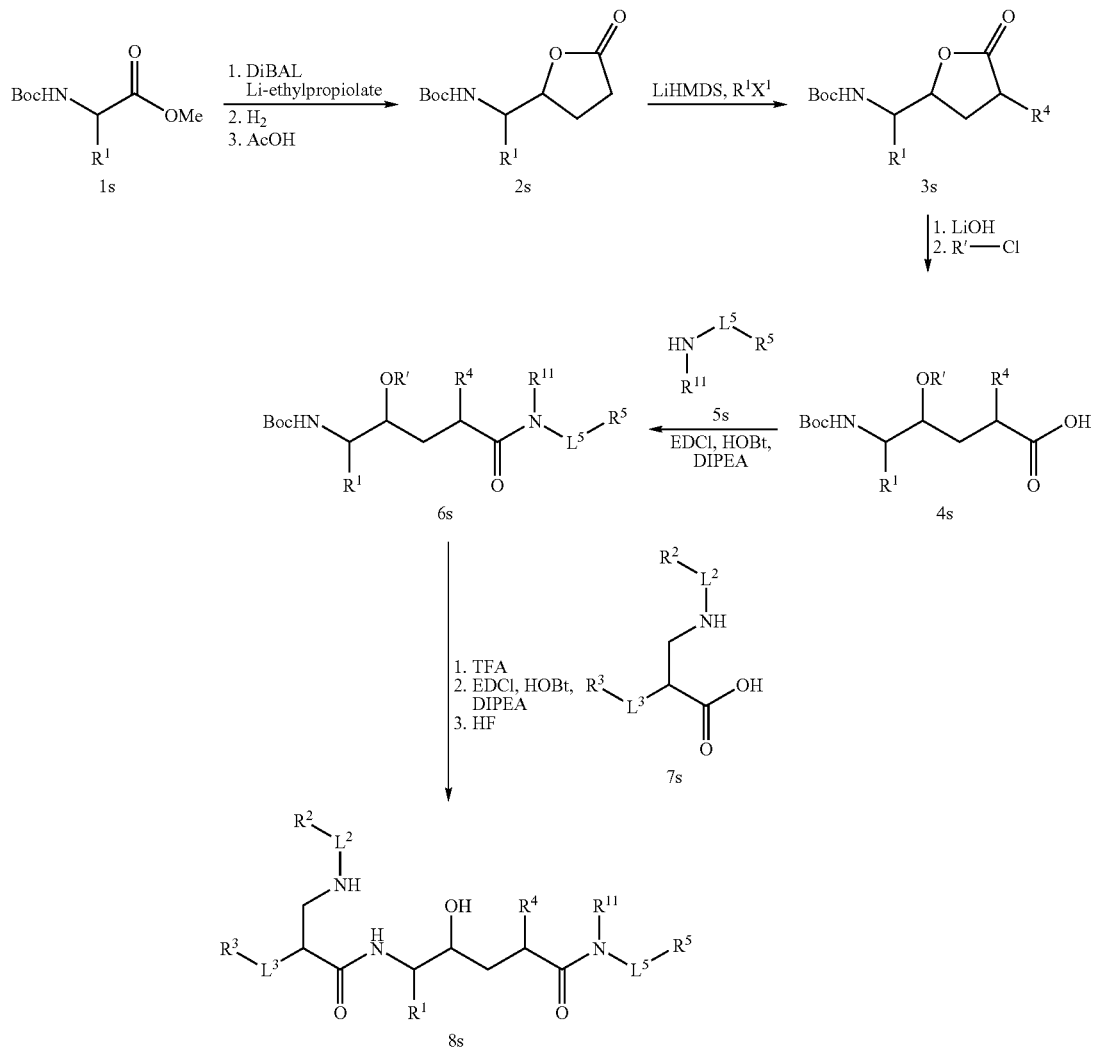

In Scheme 1, $R^1$, $R^2$, $R^3$, $R^4$, $R^5$, $R^{11}$, $L^2$, $L^3$, and $L^5$ are as defined above in the discussion of the inhibitors of the present invention. X' is a halogen (e.g. iodide, chloride or bromide) and R' is a hydroxyl protecting group (e.g. TBDMS, TBS). Those of skill in the art will understand how to protect a particular functional group, such as a hydroxyl or amine, from interfering with a chosen set of reaction conditions. For examples of useful protecting groups, See Greene et al., PROTECTIVE GROUPS IN ORGANIC SYNTHESIS, John Wiley & Sons, New York, 1991.

In the above scheme, the methyl ester 1s is cyclyzed to the corresponding lactone 2s followed by substitution with the halogenated $R^1$ group to yield the substituted lactone 3s. Ring opening and protection of the resulting hydroxyl group yields To develop useful β-secretase inhibitors, candidate inhibitors capable of selectively decreasing memapsin 2 activity may be identified in vitro and subsequently tested for their ability to reduce the production of Aβ. The activity of the inhibitor compounds can be assayed utilizing methods known in the art and/or those methods presented herein.

Compounds that decrease memapsin 2 activity may be identified and tested using biologically active memapsin 2, either recombinant or naturally occurring. Memapsin 2 can be found in native cells, isolated in vitro, or co-expressed or expressed in a cell. Measuring the reduction in the memapsin 2 activity in the presence of an inhibitor relative to the activity in the absence of the inhibitor may be performed using a variety of methods well-known in the art.

For example, the compounds may be tested for their ability to cause a detectable decrease in hydrolysis of a β-secretase site of a peptide in the presence of memapsin 2. These data can be expressed, for example, as $K_i$, $K_i$ apparent, Vi/Vo, or percentage inhibition. $K_i$ is the inhibition equilibrium constant which indicates the ability of compounds to inhibit a given enzyme (such as memapsin 2, memapsin 1, and/or cathepsin D). Numerically lower $K_i$ values indicate a higher affinity of the compounds of the invention for the enzyme. The $K_i$ value is independent of the substrate, and converted from $K_i$ apparent.

$K_i$ apparent is determined in the presence of substrate according to established techniques (see, for example, Bieth, J., *Bayer-Symposium V: Proteinase Inhibitors*, pp. 463-469, Springer-Verlag, Berlin (1994)). The standard error for the $K_i$ apparent is the error from the nonlinear regression of the Vi/Vo data measured at different concentrations of the compounds of the invention (e.g., between about 10 nM to about 1000 nM) employing well-known techniques (see, for example, Bieth, J., *Bayer-Symposium V: Proteinase Inhibitors*, pp. 463-469, Springer-Verlag, Berlin (1994), Ermolieff, J., et al., *Biochemistry* 39:12450-12456 (2000), the teachings of which are incorporated herein by reference in their entirety). Vi/Vo depicts the ratio of initial conversion velocites of an enzyme substrate (Ermolieff, et al., *Biochemistry* 40:12450-12456 (2000)) by an enzyme in the absence (Vo) or presence (Vi) of an inhibitor. A Vi/Vo value of 1.0 indicates that a compound does not inhibit the enzyme. A Vi/Vo value less than 1.0 indicates that a compound of the invention inhibits enzyme activity.

Once compounds are identified that are capable of reducing the hydrolysis of a β-secretase site of a peptide in the presence of memapsin 2, the compounds may be further tested for their ability to selectively inhibit memapsin 2 relative to other enzymes. Typically, the other enzyme is a peptide hydrolase, such as memapsin 1 or cathepsin D. Compounds that decrease cathepsin D activity or memapsin 1 activity are tested using biologically active enzyme, either recombinant or naturally occurring. Cathepsin D or memapsin 1 activity can be found in native cells, isolated in vitro, or co-expressed or expressed in a cell. Inhibition by a compound of the invention is measured using standard in vitro or in vivo assays such as those well known in the art or as otherwise described herein.

For example, selectivity may be measured by determining the extent to which memapsin 2 hydrolyzes a substrate peptide compared to the extent to which the same compound inhibits memapsin 1 and/or cathepsin D cleaving of a β-secretase site of a substrate peptide. Exemplary substrate peptides are useful in determining the activity of memapsin 2 includes APP and derivatives thereof, such as FS-2 (Bachem Americas, Torrance, Calif.). Exemplary substrate peptides are useful in determining the activity of memapsin 1 and cathepsin D include, for example, peptides with the sequence ELDLAVEFWHDR (SEQ ID NO.:1). These data can be expressed, for example, as $K_i$, $K_i$ apparent, Vi/Vo, or percentage inhibition and depict the inhibition of a compound for memapsin 2 activity relative to memapsin 1 or cathepsin D activity. For example, if the $K_i$ of a reaction between an inhibitor compound of the invention and memapsin 1 or cathepsin D is 1000 and the $K_i$ of a reaction between an inhibitor compound of the invention and memapsin 2 is 100, the inhibitor compound inhibits the β-secretase activity of memapsin 2 ten fold, relative to memapsin 1.

Compounds demonstrating the ability to cause a detectable decrease in hydrolysis of a β-secretase site of a peptide in the presence of memapsin 2 (or, in addition, selectivity of action toward memapsin 2), may be tested in cell models or animal models for their ability to cause a detectable decrease in the amount or production of β-amyloid protein (Aβ). For example, isosteric inhibitors of memapsin 2 have been tested for their ability to decrease Aβ production in cultured cells (copending U.S. Application No. 20040121947, and International Application No. PCT/US02/34324 (Publication No. WO 03/039454)). Briefly, inhibitors may be added to a culture of cells (e.g. human embryonic kidney (HEK293) cells, HeLa cells, Chinese hamster ovary cells, or neuroblastoma line M17 cells) stably transfected with a nucleic acid constructs that encode human APP Swedish mutant (or London mutation or double mutant) and, if needed, a nucleic acid construct encoding human memapsin 2. Immunoprecipitation of Aβ followed by SDS-gel electrophoresis allows detection and quantitation of the amount of Aβ produced in the presence and absence of inhibitor.

In addition to cell cultures, animal models may be used to test inhibitors of memapsin 2 for their ability to decrease Aβ production. For example, an animal (e.g. tg2576 mice) expressing the Swedish mutation of the human amyloid precursor protein (Hsiao, K., et al., *Science* 274, 99-102 (1996) may be injected intraperitoneally with an inhibitor. The plasma may then be collected and Aβ levels determined by capture ELISA (BioSource International, Camarillo, Calif.).

The presence of inhibitors in organs of animal models or within cellular compartments may be ascertained using a fluorescent tag conjugated to the inhibitor and visualization via confocal microscopy (copending U.S. Application No. 20040121947, and International Application No. PCT/US02/34324 (Publication No. WO 03/039454)).

The sample obtained from the mammal can be a fluid sample, such as a plasma or serum sample; or can be a tissue sample, such as a brain biopsy. The amount of β-amyloid protein or a decrease in the production of β-amyloid protein can be measured using standard techniques (e.g. western blotting and ELISA assays).

Further examples of assays for identifying memapsin 2-β-secretase inhibitors are set forth in the Examples section below. Other methods for assaying the activity of memapsin 2, memapsin 1, and cathepsin D and the activity of agents that decrease the activity of these enzymes are known in the art. The selection of appropriate assay methods is well within the capabilities of those of skill in the art.

Pharmaceutical Compositions

In another aspect, the present invention provides pharmaceutical compositions comprising a memapsin 2 β-secretase inhibitor compound of the invention or a memapsin 2 β-secretase inhibitor compound in combination with a pharmaceutically acceptable carrier. The pharmaceutical compositions include optical isomers, diastereomers, or pharmaceutically acceptable salts of the inhibitors disclosed herein. The memapsin 2 β-secretase inhibitor included in the pharmaceutical composition may be covalently attached to a carrier moiety, as described above. Alternatively, the memapsin 2 β-secretase inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

Formulations

The β-secretase inhibitors of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat Alzheimer's disease, such compositions will contain an amount of active ingredient effective to achieve the desires result (e.g. decreasing β-secretase activity or β-amyloid production). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, including a disease that results in increased activity of memapsin 2 or increased accumulation of β-amyloid protein, whether the mammal suffers from another disease, and its route of administration; size, age, sex, health, body weight, body mass index, and diet of the recipient; nature and extent of symptoms of the disease being treated (e.g., Alzheimer's disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of reducing the activity of memapsin 2 activity, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring memapsin 2 inhibition and adjusting the dosage upwards or downwards, as described above. Adjusting the dose to achieve maximal efficacy in humans based on the methods described above and other methods as are well-known in the art is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

Methods of Reducing the Activity of Memapsin 2 Beta-Secretase

In another aspect of the present invention, the β-secretase inhibitor compounds of the invention can be employed in methods to decrease memapsin 2 activity, decrease hydrolysis of a β-secretase site of a memapsin 2 substrate, and/or decrease the accumulation of β-amyloid protein relative to the amount of memapsin 2 activity, hydrolysis of a β-secretase site, and accumulation of β-amyloid protein, respectively, in the absence of the β-secretase inhibitor.

In an exemplary embodiment, a method of reducing memapsin 2 activity is provided. The method includes contacting a memapsin 2 with an effective amount (i.e. in an amount effective to achieve its intended purpose) of β-secretase inhibitor compound of the present invention. The memapsin 2 may be contacted in any appropriate environment. The memapsin 2 activity is decreased relative the amount of activity in the absence of β-secretase inhibitor.

In another exemplary embodiment, a method is provided of selectively reducing memapsin 2 activity using an effective amount of an inhibitor of the present invention. Selective reduction of the activity of memapsin 2 means that memapsin 2 is not only reduced relative to its activity in the absence of inhibitor, but is reduced to a greater extent as compared to the reduction in activity due to inhibitor action against another peptide hydrolase. For example, as described above, the reduction in activity of an enzyme may be expressed in terms of the inhibitory constant ($K_i$). Where an inhibitor selectively reduces the activity of memapsin 2, the $K_i$ of the reaction between an inhibitor compound of the invention and memapsin 2 is less than the $K_i$ of the reaction between an inhibitor compound of the invention and another peptide hydrolase.

In an exemplary embodiment, the $K_i$ of the reaction between an inhibitor compound of the invention and memapsin 2 is at least 2 times less than the $K_i$ of the reaction between an inhibitor compound of the invention and another peptide hydrolase. In another exemplary embodiment, the $K_i$ of the reaction between an inhibitor compound of the invention and memapsin 2 is at least 10 times less than the $K_i$ of the reaction between an inhibitor compound of the invention and another peptide hydrolase. In another exemplary embodiment, the $K_i$ of the reaction between an inhibitor compound of the invention and memapsin 2 is at least 100 times less than the $K_i$ of the reaction between an inhibitor compound of the invention and another peptide hydrolase. In another exemplary embodiment, the $K_i$ of the reaction between an inhibitor compound of the invention and memapsin 2 is at least 1000 times less than the $K_i$ of the reaction between an inhibitor compound of the invention and another peptide hydrolase. In another exemplary embodiment, the $K_i$ of the reaction between an inhibitor compound of the invention and memapsin 2 is at least 10000 times less than the $K_i$ of the reaction between an inhibitor compound of the invention and another peptide hydrolase.

In some related embodiments, the inhibitor selectively reduces the activity of memapsin 2 as compared to memapsin 1. In other related embodiments, the inhibitor selectively reduces the activity of memapsin 2 as compared to cathepsin D.

Thus, the present invention provides methods of selectively reducing the activity of memapsin 2. The method includes contacting a memapsin 2 with a β-secretase inhibitor compound of the present invention. In a related embodiment, the method includes contacting the memapsin 2 with a β-secretase inhibitor in the presence of memapsin 1. In an alternative related embodiment, the method includes contacting the memapsin 2 with a β-secretase inhibitor in the presence of cathepsin D. In yet another related embodiment, the method includes contacting the memapsin 2 with a β-secretase inhibitor in the presence of cathepsin D and memapsin 1.

In some embodiments, the activity of memapsin-2 β-secretase may be determined by measuring the hydrolysis of a β-secretase site of a β-secretase substrate. Thus, the present invention also relates to a method of decreasing the hydrolysis of a β-secretase site of a β-secretase substrate by contacting a memapsin 2 with a β-secretase inhibitor compound of the present invention. In some embodiments, the hydrolysis of a β-secretase site is decreased relative the amount of hydrolysis in the absence of the inhibitor. In other embodiments, the hydrolysis is selectively reduced as compared to hydrolysis by memapsin 1 and/or cathepsin D. Thus, a method of selectively decreasing hydrolysis of a β-secretase site of a β-amyloid precursor protein relative to memapsin 1 and/or cathepsin D in a sample is provided. The method includes contacting a memapsin 2 with a β-secretase inhibitor compound of the present invention.

In another embodiment, the present invention relates to a method of decreasing the amount of β-amyloid protein in a sample by contacting the memapsin 2 with an inhibitor compound of the present invention. The amount of β-amyloid protein in a sample is decreased relative the amount of β-amyloid protein in the sample in the absence of the inhibitor. Thus, the accumulation of β-amyloid protein is thereby decreased.

Memapsin 2 may be contacted in any suitable environment or any suitable sample. For example, memapsin 2 may be contacted in vitro, within a cell, or within a mammal. Typically, in vitro solutions are selected such that the components do not substantially interfere with the enzymatic activity of memapsin 2 (e.g. aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact the memapsin 2 with the inhibitor. The cell may contain endogenous memapsin 2 or recombinant memapsin 2 as previously described (copending U.S. Application No. 20040121947, and International Application No. PCT/US02/34324 (Publication No. WO 03/039454)). Exemplary cells include human embryonic kidney (HEK293) cells, HeLa cells, Chinese hamster ovary cells, or neuroblastoma line M17 cells Hela cells, 293 cells. In an exemplary embodiment, the compounds of the invention are administered to a mammal to inhibit the hydrolysis of a β-secretase site of a β-amyloid precursor protein (e.g. a mouse, rabbit or human).

Methods of Treating Alzheimer's Disease

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

Thus, in some embodiments, the invention provides a method of treating Alzheimer's disease in a mammal comprising the step of administering to the mammal an effective amount of the β-secretase inhibitors of the invention. The mammals treated with the inhibitors may be human primates, nonhuman primates and/or non-human mammals (e.g., rodents, canines). In one embodiment, the mammal is administered a compound of the invention that reduces β-secretase activity (inhibits memapsin 1 and memapsin 2 activity). In another embodiment, the mammal is administered a compound that selectively reduces memapsin 2 activity. In a related embodiment, the compound has minimal or no effect on reducing memapsin 1 activity. Therefore, the present invention also provides a method of treating Alzheimer's disease in a subject in need thereof, the method comprising administering to the subject a β-secretase inhibitor compound. In an exemplary embodiment, the β-secretase inhibitor compound is part of a pharmaceutical formulation, as described above.

The inhibitor compounds of the invention can be employed in the treatment of diseases or conditions associated with β-secretase activity, which can halt, reverse or diminish the progression of the disease or condition, in particular Alzheimer's disease. In addition to compounds that decrease memapsin 2 activity, compounds that selectively reduce memapsin 2 activity are useful to treat diseases or conditions or biological processes 30 association with memapsin 2 activity rather than diseases or conditions or biological processes associated with both memapsin 2 activity and another peptide hydrolase (such as cathepsin D or memapsin 1).

For example, both memapsin 1 and memapsin 2 cleave amyloid precursor protein (APP) at a β-secretase site to form β-amyloid protein (also referred to herein as Aβ or β-amyloid protein). Thus, both memapsin 1 and memapsin 2 have β-secretase activity (Hussain, I., et al., *J. Biol. Chem.* 276:

23322-23328 (2001)). However, the β-secretase activity of memapsin 1 is significantly less than the β-secretase activity of memapsin 2 (Hussain, I., et al., *J. Biol. Chem.* 276:23322-23328 (2001)). Memapsin 2 is localized in the brain, and pancreas, and other tissues (Lin, X., et al, *Proc. Natl. Acad. Sci. USA* 97:1456-1460 (2000)) and memapsin 1 is localized preferentially in placentae (Lin, X., et al., *Proc. Natl. Acad. Sci. USA* 97:1456-1460 (2000)). Alzheimer's disease is associated with the accumulation of Aβ in the brain as a result of cleaving of APP by β-secretase (also referred to herein as memapsin 2, ASP2 and BACE). Thus, methods employing the compounds which selectively inhibit memapsin 2 activity relative to memapsin 1 activity may be important in the treatment of memapsin 2-related diseases, such as Alzheimer's disease. Selective inhibition of memapsin 2 activity makes the compounds of the invention suitable drug candidates for use in the treatment of Alzheimer's disease.

Methods of Administering Beta-Secretase Inhibitors to the CNS

The inhibitor compounds of the present invention may be administered to the CNS through either invasive or non-invasive methods. Non-invasive methods of administration include those methods that do not require the use of a mechanical or physical means to breach the integrity of the blood-brain barrier. Typically, non-invasive methods include the use of immunoliposomes, blood-brain barrier disruption (BBBD), or the olfactory pathway.

Immunoliposomes are liposomes with antibodies or antibody fragments that bind to receptors or transporters expressed on brain capillary endothelial cells attached to the surface of the liposome. An exemplary immunoliposome combines polymer (e.g. PEGylation) technology with that of chimeric peptide technology. For example, the β-secretase inhibitor may be packaged into a unilamellar lipid vesicle containing a PEG$^{2000}$ derivative that contains a reactive groups at one end, for attachment to a complimentary reactive group of an antibody or fragment thereof. Complimentary reactive groups are well known in the art and, include, for example, amine and activated carboxylic acids, thiols and maleimides, and the like (Ambikanandan et al., *J. Pharm Pharmaceut Sci* 6(2):252-273 (2003); Huwyler et al., *Proc. Natl. Acad. Sci. USA,* 93:14164-14169 (1996); and Huwyler et al., *J Pharmcol Exp Ther.* 282:1541-1546 (1997); and U.S. Pat. No. 6,372,250).

Blood-brain barrier disruption is a temporal loss of the integrity of the tight junctions between endothelial cells that comprise the blood brain barrier. Typically, the compound is administered via systemic or intercarotid injection in conduction with transient blood-brain barrier disruption (BBBD). Exemplary agents useful for inducing BBBD include solvents such as dimethyl sulfoxide (DMSO); ethanol (EtOH); metals (e.g. aluminum); X-irradiation; induction of pathological conditions (e.g. hypertension, hypercapnia, hypoxia, or ischemia); anti-neoplastic agents (e.g. VP-16, cisplatin, hydroxyurea, fluorouracil and etoposide); or concurrent systemic administration of the convulsant drug metrazol and the anti-convulsant drug pentobarbital (Ambikanandan et al., *J. Pharm Pharmaceut Sci* 6(2):252-273 (2003)); vasoactive leukotrienes (Black et al., *J Neurosurg,* 81(5):745-751 (1994)); intracarotid infusion of bradykinin, histamine, or the synthetic bradykinin analog RMP-7 (Miller et al., *Science* 297: 1116-1118 (2002), Matsukado, et al., *Neurosurgery* 39:125-133 (1996), Abbott, et al., *Mol Med Today* 2:106-113 (1996), Emerich et al., *Clin Pharmacokinet* 40:105-123 (2001)); hyaluronidase (U.S. Pat App No. 20030215432, Kreil, et al. *Protein Sci.,* 4(9):1666-1669 (1995)); and intercarotid injection of inert hypertonic solutions such as mannitol, or arabinose (Neuwelt, E. A., et al., in Neuwelt E A (ed), *Implications of the Blood Brain Barrier and its Manipulation: Clinical Aspects.* Vol. 2, Plenum Press, New York, (1989), Neuwelt, et al., *J Nucl Med,* 35:1831-1841 (1994), Neuwelt et al., *Pediatr Neurosurg* 21:16-22 (1994), Kroll et al., *Neurosurg,* 42:1083-1099 (1998), Rapoport, *Cell Mol Neurobiol* 20:217-230 (2000), and Doran et al., *Neurosurg* 36:965-970, (1995)).

Olfactory pathway administration is the intranasal delivery of the compound to the olfactory nerves in the upper third of the nasal passages. After intranasal delivery, the compound is transported back along the sensory olfactory neurons to yield significant concentrations in the cerebral spinal fluid (CSF) and olfactory bulb (Thorne et al., *Brain Res,* 692(1-2):278-282 (1995); Thorne et al., *Clin Pharmacokinet* 40:907-946 (2001); Illum, *Drug Discov Today* 7:1184-1189 (2002); U.S. Pat. No. 6,180,603; U.S. Pat. No. 6,313,093; and U.S. Pat App No. 20030215398).

Invasive methods of administration are those methods that involve a physical breach of the blood-brain barrier typically through a mechanical or physical means to introduce the compound into the CSF, or directly into the parenchyma of the brain. Typically, invasive methods of administration may include injection or surgical implantation of the compound.

In injection methods, a needle is used to physically breach the BBB and deliver the compound directly into the CSF. Exemplary injection methods include intraventricular, intrathecal, or intralumbar routes of administration and may also involve infusion of the compound through a reservoir external to the body (Krewson et al., *Brain Res* 680:196-206 (1995); Harbaugh et al., *Neurosurg.* 23(6):693-698 (1988); Huang et al., *J Neurooncol* 45:9-17 (1999); Bobo et al., *Proc Natl Acad Sci USA* 91:2076-2082 (1994); Neuwalt et al., *Neurosurg.* 38(4):1129-1145 (1996)).

In surgical implantation methods, the compound is placed directly into the parenchyma of the brain. Exemplary surgical implantation methods may include incorporation of the compound into a polyanhydride wafer placed directly into the interstitium of the brain (Brem et al., *Sci Med* 3(4): 1-11 (1996); Brem et al., *J Control Release* 74:63-67 (2001)).

Crystallized Complexes

In another aspect, the present invention provides a crystallized complex containing a memapsin 2 protein and a β-secretase inhibitor of the present invention. Memapsin 2 proteins useful in forming co-crystals with isostere compounds (e.g. memapsin 2 protein fragments, transmembrane proteins, etc.) have been previously discussed in detail (copending U.S. Application No. 20040121947, and International Application No. PCT/US02/34324 (Publication No. WO 03/039454)). These memapsin 2 proteins are equally useful in forming crystallized complexes with β-secretase inhibitors of the present invention.

The crystallized complex may be formed employing techniques described in copending U.S. Application No. 20040121947, and International Application No. PCT/US02/34324 (Publication No. WO 03/039454). Briefly, a nucleic acid construct encoding the protein is generated, is expressed in a host cell, such as a mammalian host cell (e.g., Hela cell, 293 cell) or a bacterial host cell (e.g., *E. coli*), is purified and is crystallized with a compound or compounds of the invention. The diffraction resolution limit of the crystallized protein can be determined, for example, by x-ray diffraction or neutron diffraction techniques.

In an exemplary embodiment, the crystallized protein may have an x-ray diffraction resolution limit not greater than about 4.0 Å. The crystallized protein may also have an x-ray diffraction resolution limit not greater than about 4.0 Å, about 3.5 Å, about 3.0 Å, about 2.5 Å, about 2.0 Å, about 1.5 Å, about 1.0 Å, or about 0.5 Å. In some embodiments, the crystallized protein may also have an x-ray diffraction resolution limit not greater than about 2 Å. The diffraction resolution limit of the crystallized protein can be determined employing standard x-ray diffraction techniques.

In an other exemplary embodiment, the β-secretase inhibitor of the crystallized complex is in association with said protein at an $S_3'$ binding pocket, an $S_4'$ binding pocket and/or an $S_4$ binding pocket. $S_3'$, $S_4'$, and $S_4$ binding pockets are discussed in detail in copending U.S. Application No. 20040121947, and International Application No. PCT/US02/34324 (Publication No. WO 03/039454).

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the β-secretase inhibitors of the present invention are equally applicable to the methods of treating disease states and/or the pharmaceutical compositions described herein. All publications, patents, and patent applications cited herein are hereby incorporated by reference in their entirety for all purposes.

EXAMPLES

Example 1

Synthesis of Heterocycle Alcohols

Example 1.1

Methylthiazole Methanol

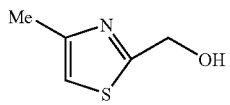

Methylthiazole (1.0 g, 10.1 mmol) in THF at −78° C. was treated with n-BuLi (1.6 M, 7.56 mL) for 30 min, DMF (1.4 mL, 18.2 mmol) was added dropwise. The resulting reaction mixture was warmed to r.t. After the starting material was disappeared (by TLC), the reaction mixture was recooled to 0° C. and LAH (0.69 g, 18.5 mmol) was added. The mixture was warmed to r.t. and stirred for 1 h, the reaction was quenched with aqeuous NH$_4$Cl, diluted with EtOAc. The organic solution was separated, extracted twice with EtOAc, dried with Na$_2$SO$_4$, and concentrated. The residue was purified with flash chromatography to give the corresponding alcohol as a light yellow oil. $^1$H-NMR: (300 MHz, CDCl$_3$), δ: 6.89 (s, 1H); 4.95 (s, 2H); 2.48 (s, 3H).

Example 1.2

Dimethylimidizolyl Methanol and Dimethylpyrazolyl Methanol

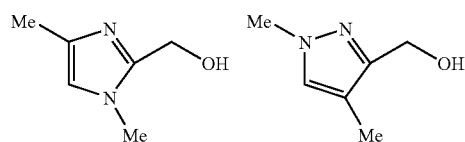

Methylimidizole (5 g, 60.89 mmol) was treated with trimethyl phosphate (3.41 g, 24.36 mmol) and diisopropyl ethylamine at 150° C. for 6 h. The resulting mixture was dissolved in benzene and the solution was stirred with 30% aqueous potassium hydroxide. Evaporation of the solvent from the organic layer and flash chromatography of the residue afforded dimethylimidazole as white solid. Following the same procedure the dimethylpyrazine was also made.

Using the procedure of preparation of methylthiazole methanol in Example 1.1, the alcohols were made from the corresponding dimethyl species. Dimethylimidizolyl methanol was a white solid. Dimethylpyrazolyl methanol was a light yellow oil. $^1$H-NMR: (300 MHz, CDCl$_3$), δ: 7.24 (s, 1H); 4.65 (s, 2H); 3.89 (s, 3H); 2.07 (s, 3H).

Example 1.3

Methylimidizolyl Methanol, Thiazole Methanol, Methyl Thiodiazolyl Methanol

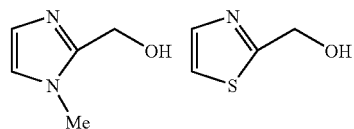

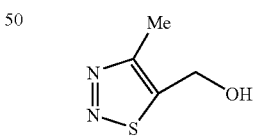

Aldehyde (100 mg, 0.91 mmol) in diethyl ether at 0° C. was added lithium aluminium hydride (51.7 mg, 1.36 mmol), then the resulting mixture was warmed to r.t. After 1 h, the reaction was quenched with Na$_2$SO$_4$.10H$_2$O and stirred for a couple of hours. The organic solution was filtrated. The residue was purified with flash chromatography to give the corresponding alcohol as a white solid. $^1$H-NMR: (300 MHz, CDCl$_3$), δ: 6.86 (m, 2H); 4.57 (s, 2H); 3.88 (br, 1H); 3.65 (s, 3H).

Same as the above procedure to prepare the thiazolyl methanol, a light yellow oil. $^1$H-NMR: (300 MHz, CDCl$_3$), δ: 6.86 (m, 2H); 4.57 (s, 2H); 3.88 (br, 1H); 3.65 (s, 3H).

Methyl thiodiazolyl methanol, a light yellow oil. $^1$H-NMR: (300 MHz, CDCl$_3$), δ: 5.05 (s, 2H); 2.68 (s, 3H).

Thiazolyl methanol, a light yellow oil. $^1$H-NMR: (300 MHz, CDCl$_3$), δ: 7.77 (d, 1H); 7.35 (d, 1H); 4.99 (s, 2H).

Example 1.4

Methyldiazolyl Methanol

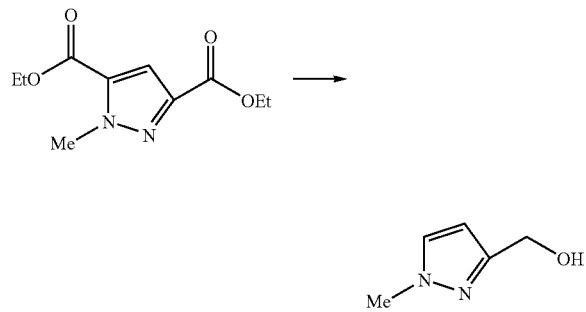

Diethyl pyrazoledicarboxylate (2.0 g, 9.42 mmol) in THF at 0° C. was added NaH (60% in mineral oil, 0.42 g, 10.37 mmol) portionwise. The resulting mixture was warmed to r.t. and stirred overnight. The reaction was quenched with saturated aqueous NH$_4$Cl carefully. The mixture was diluted with EtOAc, separated, and extracted with EtOAc twice. The combined organic layers was dried over Na$_2$SO$_4$, concentrated, and purified by flash chromatography to afford the product as a colorless oil.

The above diester (1.0 g, 4.42 mmol) was dissolved in MeOH, a solution of KOH in MeOH (0.28 g of KOH in 2.5 mL of MeOH) was added, and the mixture was stirred at r.t. for 24 h. After removal of solvent under reduced pressure at low temperature, the residue was dissolved in water and neutralized with aqueous HCl (1M solution). Extraction of the mixture with CHCl$_3$ three times afforded the crude product after concentration of the combined organic layers. Without further purification the crude above product was heated to 210° C. for 30 min. to provide a dark brown oil, which was purified by flash chromatography to give the ester.

The ester was reduced to corresponding alcohol by LAH. $^1$H-NMR: (300 MHz, CDCl$_3$), δ: 7.32 (s, 1 H); 6.25 (s, 1 H); 4.68 (s, 2H); 3.88 (s, 3 H); 2.74 (br, 1 H).

Example 1.5

Methyloxazolyl Methanol

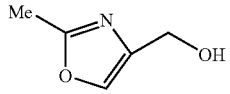

A suspension of ethyl acetamide hydrochloride (0.87 g, 7.1 mmol) in DCM at 0° C. was treated with serine ethyl ester hydrochloride (1 g, 5.9 mmol) and triethylamine (0.82 mL, 5.9 mmol) and the reaction mixture allowed to r.t. After 24 h, the reaction was quenched with water, and the layers were separated. The aqueous layer was extracted with DCM twice, the combined organic layers was concentrated to give a crude product. Without further purification the crude product was treated with DBU/CCl$_4$/Py (6.6 mL/15 mL/22.5 mL) in acetonitrile. After 3 h, the solvent was removed in vacuo, the residue was dissolved in EtOAc, washed with water for three times. The organic layer was dried over Na$_2$SO$_4$, concentrated and the residue was purified by flash chromatography to afford the pure ester, which was reduced by LAH to get the desired alcohol. $^1$H-NMR: (300 MHz, CDCl$_3$), δ: 7.51 (s, 1 H); 4.58 (s, 2 H); 2.48 (s, 3 H).

Example 1.6

Dimethyloxazolyl Methanol

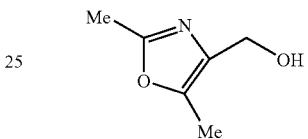

Sodium nitrite (12.2 g, 0.18 mol) in water was added dropwise to a solution of ethyl acetoacetate (19.5 mL, 0.15 mol) in glacial acetic acid at r.t. for 1 h. The resulting mixture was stirred for further 1 h at r.t, 80 mL of water added, and stirring continued for 2 h. The reaction mixture was extracted with ether for three times, washed with aqueous Na HCO$_3$, water and brine. The organic layer was dried, concentrated to afford the crude product. Without further purification, the crude product (6.5 g, 40.8 mmol) in a mixture of acetic anhydrous (19.3 mL, 0.21 mol), acetic acid (58 mL), and 210 mg of Pd/C (10% w/w) was hydrogenated at 50 Psi pressure for 1.5 h. The catalyst and solvent were removed and the residue was triturated with hexanes to give ethyl N-acetylacetoacetate as solid, m.p. 38-40° C.

The above solid product (3.3 g, 17.6 mmol) was treated with thionyl chloride (1.3 mL, 17.6 mmol) in dry benzene at r.t. The mixture was warmed to 30° C. for 1 h, and for 30 min under water-pump vacuum. The residue was diluted with EtOAc and washed with aqueous NaHCO$_3$, water, and brine. The organic layer was dried, concentrated to give the crude product as a brown oil, which was further reduced by LAH to provide the desired alcohol as a light yellow solid. $^1$H-NMR: (300 MHz, CDCl$_3$), δ: 4.51 (s, 2 H); 2.58 (s, 3 H); 2.43 (s, 3 H), 2.31 (s, 3 H).

A similar procedure was used to prepare the corresponding ethyl heterocycle:

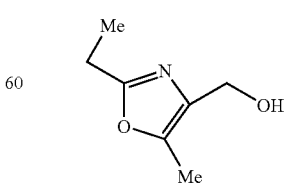

$^1$H-NMR: (300 MHz, CDCl$_3$), δ: 4.51 (s, 2 H); 2.75 (m, 2 H); 2.31 (s, 3 H); 1.33 (m, 3 H).

Example 1.7

Dimethylthiazolyl Methanol

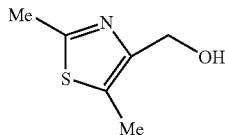

A mixture of ethyl N-acetylacetoacetate (3.6 g, 19.3 mmol) and phosphorus pentasulfide (4.3 g, 9.6 mmol) in toluene was heated to 75° C. for 2 h. The reaction mixture was diluted with EtOAc and quenched with water. The organic layer was separated. The aqueous layer was extracted with EtOAc. The combines organic layers was washed with brine, dried, and concentrated to give the crude ester, which was reduced with LAH without further purification to provide the desired alcohol. $^1$H-NMR: (300 MHz, CDCl$_3$), δ: 4.64 (s, 2 H); 3.75 (br, 3 H); 2.64 (s, 3 H), 2.42 (s, 3 H).

A similar procedure was used to prepare the corresponding ethyl heterocycle:

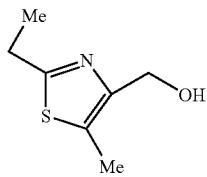

Same procedure as above was used to prepare the alcohol. $^1$H-NMR: (300 MHz, CDCl$_3$), δ: 4.65 (s, 2 H); 2.98 (m, 2 H); 2.43 (s, 3 H); 1.36 (m, 3 H).

Example 1.8

Methyloxazaimidizolyl Methanol

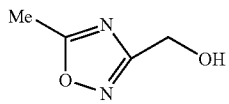

Ethyl chlorooximinoacetate (2g) in 80 mL of dry diethyl ether was treated with dry ammonia gas at 0° C. The precipitated ammonium chloride was filtered with suction and the filtrate was evaporated under reduced pressure to give the product, m.p. 96-97° C. This compound (1g) was treated with acetic anhydrous (1.1 mL) in pyridine at reflux condition for 1 h. The solvent was removed and the residue was dissolved in CHCl$_3$. The organic layer was washed with water, aqueous NaHCO$_3$, and brine, dried and concentrated to give the crude product, which was reduced to desired alcohol with NaBH$_4$ in methanol. $^1$H-NMR: (300 MHz, CDCl$_3$), δ: 4.78 (s, 2 H); 2.63 (s, 3 H).

The procedure below was used to produce the following methyloxazaimidizolyl methanol:

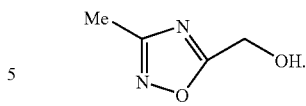

Acetamide oxime (0.95 g, 12.8 mmol) in THF was added NaH (60% in mineral oil, 0.62 g, 15.4 mmol) at r.t. The mixture was then heated up to 80° C. for 10 min and TEMOM protected ethyl glycolate was added. The resulting was heated at this temperature for 2 h. The solvent was removed and the residue was diluted CHCl$_3$ and washed with water and brine. The solvent was removed and the residue was purified with flash chromatography to give the product, which was deprotected with TFA to provide the desired alcohol as a white solid. $^1$H-NMR: (300 MHz, CDCl$_3$), δ: 4.90 (s, 2 H); 2.43 (s, 3 H).

Example 2

Preparation of Exemplary Beta-Secretase Inhibitor Compounds

Example 2.1

Synthesis of N-(tert-Butoxycarbonyl)-L-leucine-N'-methoxy-N'-methylamide

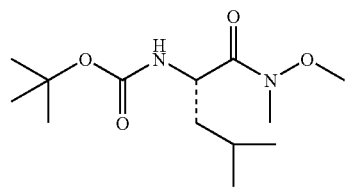

1c

To a stirred solution of N,O-dimethylhydroxyamine hydrochloride (5.52 g, 56.6 mmol) in dry dichloromethane (25 mL) under a N$_2$ atmosphere at 0° C., was added N-methylpiperidine (6.9 mL, 56.6 mmol) dropwise. The resulting mixture was stirred at 0° C. for 30 minutes. In a separate flask, commercially available N-(t-butyloxycarbonyl)-L-leucine (11.9 g, 51.4 mmol) was dissolved in a mixture of tetrahydrofuran (THF) (45 mL) and dichloromethane (180 mL) under a N$_2$ atmosphere. The resulting solution was cooled to −20° C. To this solution was added 1-methylpiperidine (6.9 mL, 56.6 mmol) followed by isobutyl chloroformate (7.3 mL, 56.6 mmol) dropwise. The resulting mixture was stirred for 5 minutes at −20° C. and the above solution of N,O-dimethylhydroxylamine was added dropwise. The reaction mixture was stirred at −20° C. for 30 minutes followed by warming to room temperature. The reaction was quenched with water and the layers were separated. The aqueous layer was extracted with CH$_2$Cl$_2$ (3 times). The combined organic layers were washed with 10% citric acid, saturated sodium bicarbonate, brine, dried over Na$_2$SO$_4$ and concentrated under reduced pressure. Flash column chromatography (25% ethyl acetate (EtOAc) in hexanes) yielded 1 (13.8 g, 97%). [α]$_D^{23}$ −23 (c 1.5, MeOH); $^1$H-NMR (400 MHZ, CDCl$_3$) δ 5.06 (d, 1 H, J=9.1 Hz), 4.70 (m, 1H), 3.82 (s, 3H), 3.13 (s, 3H), 1.70 (m, 1H), 1.46-1.36 (m, 2H) 1.41 (s, 9H), 0.93 (dd, 6H, J=6.5, 14.2 Hz); $^{13}$C-NMR (100 MHZ, CDCl$_3$) δ 173.9, 155.6, 79.4, 61.6, 48.9, 42.1, 32.1, 28.3, 24.7, 23.3, 21.5; IR (neat) 3326, 2959, 2937, 2871, 1710, 1666, 1502, 1366, 1251, 1046 cm$^{-1}$; HRMS m/z (M+H)$^+$ calc'd for $C_{13}H_{27}N_2O_4$ 275.1971, found 275.1964.

Example 2.2

Synthesis of N-(tert-Butoxycarbonyl)-L-Leucinal

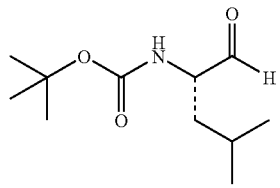

2e

To a stirred suspension of lithium aluminum hydride (LAH) (770 mg, 20.3 mmol) in diethyl ether (60 mL) at −40° C. under N$_2$ atmosphere, was added dropwise a solution of 1e (5.05 g, 18.4 mmol) in diethyl ether (20 mL). The resulting reaction mixture was stirred for 30 minutes followed by quenching with 10% aqueous NaHSO$_4$ (30 mL) and warming to room temperature for 30 minutes. This solution was filtered and the filter cake was washed with diethyl ether (two times). The combined organic layers were washed with saturated sodium bicarbonate, brine, dried over MgSO$_4$ and concentrated under reduced pressure to afford 2e (3.41 g) which was used immediately without further purification. Crude $^1$H-NMR (400 MHZ, CDCl$_3$) δ 9.5 (s, 1H), 4.9 (s, 1H), 4.2 (m, 1H), 1.8-1.6 (m, 2H), 1.44 (s, 9H), 1.49-1.39 (m, 1H), 0.96 (dd, 6H, J=2.7, 6.5 Hz).

Example 2.3

Synthesis of Ethyl (4S,5S)- and (4R,5S)-5-[(tert-Butoxycarbonyl)amino]-4-hydroxy-7-methyloct-2-ynoate

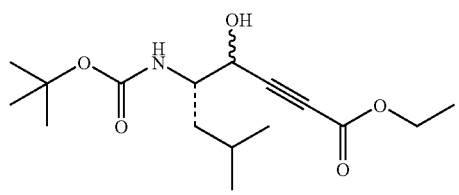

3e

To a stirred solution of ethyl propiolate (801 mL) in THF (2 mL) at −78° C. was added a 1.0 M solution of lithium hexamethyldisilazide (7.9 mL) dropwise over a 5 minutes period. The mixture was stirred for 30 min, after which N-(tert-butoxycarbonyl)-L-leucinal 2e (or N-Boc-L-leucinal) (1.55 g, 7.2 mmol) in 8 mL of dry THF was added. The resulting mixture was stirred at −78° C. for 30 minutes. The reaction was quenched with saturated aqueous NH$_4$Cl at −78° C. followed by warming to room temperature. Brine was added and the layers were separated. The organic layer was dried over Na$_2$SO$_4$ and concentrated under reduced pressure. Flash column chromatography (15% EtOAc in hexanes) yielded a mixture of acetylenic alcohols 3e (68%). $^1$H-NMR (300 MHZ, CDCl$_3$) δ 4.64 (d, 1H, J=9.0 Hz), 4.44 (br s, 1H), 4.18 (m, 2H), 3.76 (m, 1H), 1.63 (m, 1H), 1.43-1.31 (m, 2H), 1.39 (s, 9H), 1.29-1.18 (m, 3H), 0.89 (m, 6H); IR (neat) 3370, 2957, 2925, 2854, 1713, 1507, 1367, 1247, 1169, 1047 cm$^{-1}$.

Example 2.3A

Alternative synthesis of Ethyl (4S,5S)- and (4R,5S)-5-[(tert-Butoxycarbonyl)amino]-4-hydroxy-7-methyloct-2-ynoate

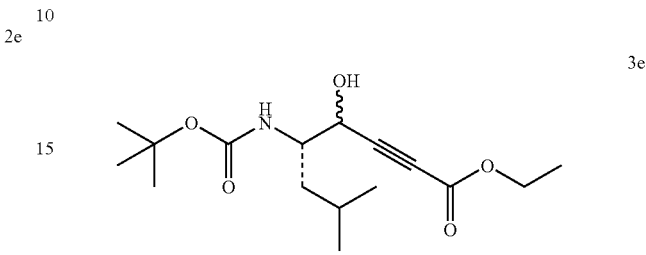

3e

To a stirred solution of DIBAL-H (1.5M in toluene, 28 mL, 42.0 mmol) at −78° C. under argon atmosphere was added of Boc-Valine methyl ester (5.0 g, 20.4 mmol) in toluene (25 mL) dropwise over 25 min (solution A). To a separate solution of LiHMDS (1.0M in tetrahydrofuran, 31 mL, 31.0 mmol) at −78° C. under argon atmosphere was added ethylpropiolate (3.1 mL, 30.6 mmol) dropwise over 5 min (solution B). After stirring at −78° C. for 80 min solution A was transferred quickly via cannulae to solution B. After stirring and additional 15 min at −78° C. the solution was allowed to warm to room temperature. After stirring an additional 3 h at room temperature, the reaction mixture was cooled to −10° C. and quenched with acetic acid (7.5 mL) and stirred for 20 min. The mixture was allowed to warm to room temperature and poured into a mixture of 50 mL ethyl acetate and 50 mL 10% citric acid and stirred for 1 h. The layers were separated and the organic layer washed with H$_2$O (2×), brine, dried with Na$_2$SO$_4$, and concentrated to yield a crude oil which was purified by flash column chromatography (20% ethyl acetate in hexanes) to provide 3e (2.0 g, 31%). $^1$H NMR identical to above procedure.

Example 2.4

(5S,1'S)-5-[1'-[(tert-Butoxycarbonyl)amino]-3'-methylbutyl]dihydrofuran-2(3H)-one (4)

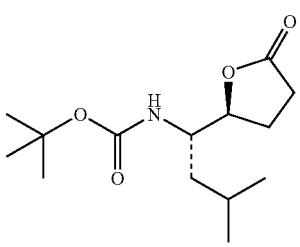

4e

To a stirred solution of 3e (1.73 g, 5.5 mmol) in methanol (MeOH) (20 mL) was added 10% Pd/C (1.0 g). The resulting mixture was placed under a hydrogen balloon and stirred for 1 hour. After this period, the reaction was filtered through a pad of Celite and the filtrate was concentrated under reduced pressure. The residue was dissolved in toluene (20 mL) and acetic acid (100 L). The resulting mixture was refluxed for 6 hours followed by cooling to room temperature and concentrating under reduced pressure. Flash column chromatography (40% diethyl ether in hexanes) yielded 4e (0.94 g, 62.8 mmol) and less than 5% of its diastereomer. Lactone 4: M.p. 74-75° C.; $[\alpha]_D^{23}$ −33.0 (c 1.0, MeOH); lit. (Fray, A. H., et al., J. Org. Chem. 51:4828-4833 (1986)) $[\alpha]_D^{23}$ −33.8 (c 1.0, MeOH); $^1$H-NMR (400 MHZ, CDCl$_3$) δ 4.50-4.44 (m, 2H), 3.84-3.82 (m, 1H), 2.50 (t, 2H, J=7.8 Hz), 2.22-2.10 (m, 2H), 1.64-1.31 (m, 3H), 1.41 (s, 9H), 0.91 (dd, 6H, J=2.2, 6.7 Hz); $^{13}$C-NMR (75 MHZ, CDCl$_3$) δ 177.2, 156.0, 82.5, 79.8, 51.0, 42.2, 28.6, 28.2, 24.7, 24.2, 23.0, 21.9; IR (neat) 2956, 2918, 2859, 1774, 1695, 1522, 1168 cm$^{-1}$; mass (EI) m/z 294 (M$^+$+Na); HRMS: m/z (M+Na)$^+$ calc'd for C$_{14}$H$_{25}$NO$_4$Na, 294.1681, found 294.1690.

Example 2.5

Synthesis of (3R,5S,1'S)-5-[1'-[(tert-Butoxycarbonyl)amino)]-3'-methylbutyl]-3-methyl-(3H)-dihydrofuran-2-one

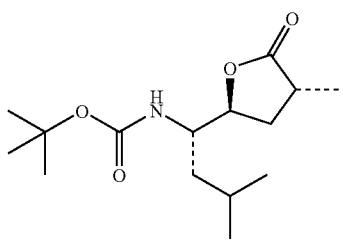

5e

To a stirred solution of lactone 4e (451.8 mg, 1.67 mmol) in THF (8 mL) at −78° C. under a N$_2$ atmosphere, was added dropwise lithium hexamethyldisilazide (3.67 mL, 1.0 M in THF, 3.67 mmol). The resulting mixture was stirred at −78° C. for 30 minutes. Methyl iodide (MeI) (228 mL) was added dropwise and the resulting mixture was stirred at −78° C. for 20 minutes. The reaction was quenched with saturated aqueous NH$_4$Cl and allowed to warm to room temperature. The reaction mixture was concentrated under reduced pressure and the residue was extracted with EtOAc (three times). The combined organic layers were washed with brine, dried over Na$_2$SO$_4$ and concentrated under reduced pressure. Flash column chromatography (15% EtOAc in hexanes) yielded 5e (0.36 g, 76%). The stereochemistry of C$_2$-methyl group was assigned based upon NOESY and COSY experiments. Irradiation of the C$_2$-methyl group exhibited 6% NOE with the C$_3$ α-proton and 5% NOE with the C$_4$-proton. The α- and β-protons of C$_3$ were assigned by 2 D-NMR. $[a]_D^{23}$ −19.3 (c 0.5, CHCl$_3$); $^1$H-NMR (300 MHZ, CDCl$_3$) δ 4.43 (t, 1H, J=6.3 Hz), 4.33 (d, 1H, J=9.6 Hz), 3.78 (m, 1H), 2.62 (m, 1H), 2.35 (m, 1H), 1.86 (m, 1H), 1.63-1.24 (m, 3H), 1.37 (s, 9H), 1.21 (d, 3H, J=7.5 Hz), 0.87 (dd, 6H, J=2.6, 6.7 Hz); $^{13}$C-NMR (75 MHZ, CDCl$_3$) δ 180.4, 156.0, 80.3, 79.8, 51.6, 41.9, 34.3, 32.5, 28.3, 24.7, 23.0, 21.8, 16.6; IR (neat) 2962, 2868, 1764, 1687, 1519, 1272, 1212, 1008 cm$^{-1}$; HRMS: m/z (M+Na)$^+$ calc'd for C$_{15}$H$_{27}$NO$_4$Na, 308.1838, found 308.1828.

Example 2.6

Synthesis of (2R,4S,5S)-5-[(tert-Butoxycarbonyl)amino]-4-[(tert-butyldimethylsilyl)-oxy]-2,7-methyloctanoic acid

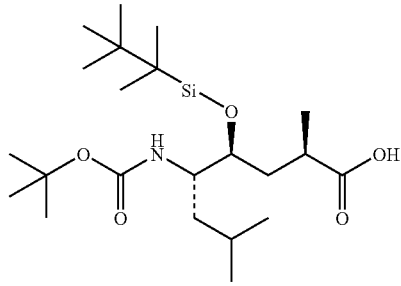

6e

To a stirred solution of lactone 5e (0.33 g, 1.17 mmol) in a mixture of THF and water (5:1; 6 mL) was added LiOH.H$_2$O (0.073 g, 1.8 equiv). The resulting mixture was stirred at room temperature for 1 hour. The volatiles were removed under reduced pressure and the remaining solution was cooled to 0° C. and acidified with 25% aqueous citric acid to pH 3. The resulting acidic solution was extracted with EtOAc three times. The combined organic layers were washed with brine, dried over Na$_2$SO$_4$ and concentrated under reduced pressure to yield the corresponding hydroxy acid (330 mg) as a white foam. This hydroxy acid was used directly for the next reaction without further purification. To the above hydroxy acid (330 mg, 1.1 mmol) in dimethylformamide (DMF) was added imidazole (1.59 g, 23.34 mmol) and tert-butyldimethylchlorosilane (1.76 g, 11.67 mmol). The resulting mixture was stirred at room temperature for 24 hours. MeOH (4 mL) was added and the mixture was stirred for an additional 1 hour. The mixture was acidified with 25% aqueous citric acid to pH 3 and was extracted with EtOAc three times. The combined extracts were washed with water, brine, dried over Na$_2$SO$_4$ and concentrated under reduced pressure. Flash column chromatography (35% EtOAc in hexanes) yielded 6e (0.44 g, 90%). M.p. 121-123° C.; $[\alpha]_D^{23}$ −40.0 (c 0.13, CHCl$_3$); $^1$H-NMR (400 MHZ, DMSO-d$^6$, 343 K) δ 6.20 (br s, 1H), 3.68 (m, 1H), 3.51 (br s, 1H), 2.49-2.42 (m, 1H), 1.83 (t, 1H, J=10.1 Hz), 1.56 (m, 1H), 1.37 (s, 9H), 1.28-1.12 (m, 3H), 1.08 (d, 3H, J=7.1 Hz), 0.87 (d, 3H, J=6.1 Hz) 0.86 (s, 9H), 0.82 (d, 3H, J=6.5 Hz), 0.084 (s, 3H), 0.052 (s, 3H); IR (neat) 3300-3000, 2955, 2932, 2859, 1711 cm$^{-1}$; HRMS: m/z (M+Na)$^+$ calc'd for C$_{21}$H$_{43}$NO$_5$NaSi, 440.2808, found 440.2830.

Example 2.7

Synthesis of Leucine-AlanineValine Inhibitor Precursor

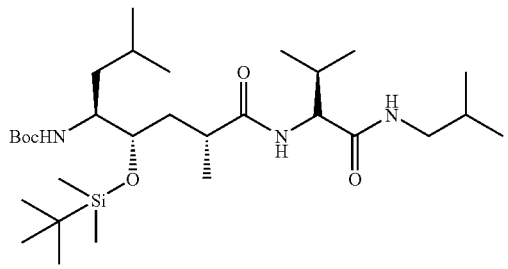

7e

The Leucine-Alanine-Valine Inhibitor Precursor 7e was produced by coupling 6e with Valine-N-iBu amide under standard EDCI/HOBt conditions as follows: to a stirred solution of Leucine-Alanine isostere 6e (0.55 g, 1.3 mmol) in dichloromethane (20 mL) was added HOBt (0.20 g, 1.6 mmol) and EDCI (0.28 g, 1.6 mmol). To this mixture was added a solution of N-Boc-Valine-N'-iBu (0.44 mL, 1.6 mmol) which was pretreated with TFA in DCM for 30 minutes and concentrated under reduced pressure, and DIPEA (1.2 mL, 6.7 mmol) in dichloromethane (10 mL). The resulting mixture was stirred at room temperature for 15 h under argon followed by quenching with NaHCO$_3$. The layers were separated and the aqueous layer was extracted with CHCl$_3$ (2×20 mL). The combined organic layer was dried with Na$_2$SO$_4$ and concentrated under reduced pressure. The resulting residue was purified by flash column chromatography (2% methanol in CHCl$_3$) to provide 7e (0.69 g, 75%). $^1$H NMR (300 MHz, CDCl$_3$+CD$_3$OD): δ 4.54 (d, 1H), 4.09 (t, 1H), 3.64-3.80 (m, 2H), 2.98-3.20 (m, 2H), 2.50-2.63 (m, 1H), 2.06-2.21 (m, 1H), 1.20-1.88 (m, 6H), 1.47 (s, 9H), 1.13 (d, 3H, J=6.3 Hz), 0.85-1.01 (m, 27H), 0.08-0.15 (m, 6H).

Example 2.8

Synthesis of Heterocycle Mixed Carbonate

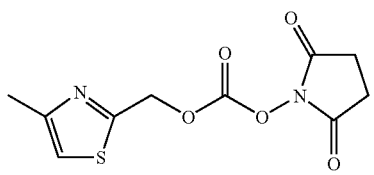

8e

To a stirred solution of 4-methyl thiazole methanol (0.47 g, 3.6 mmol) in CH$_3$CN (15 mL) was added triethylamine (1.5 mL, 11 mmol) and N,N'-disuccinnimidyl carbonate (1.12 g, 4.4 mmol). The resulting mixture was stirred at room temperature for 15 h and was concentrated under reduced pressure. The residue was dissolved in EtOAc and saturated NaHCO$_3$. The layers were separated and the aqueous layer was extracted with EtOAc (2×20 mL). The combined organic layer was washed with brine, dried with Na$_2$SO$_4$ and concentrated under reduced pressure to provide mixed carbonate 8e (955 mg, 97%) which was used for next step without further purification.

Example 2.9

Synthesis of Heterocycle Boc-Amine Ester

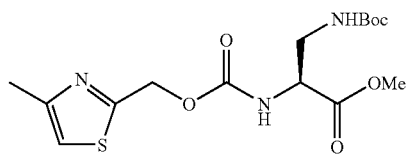

9e

To a stirred solution of H-Dap(Boc)-OMe.HCl (481 mg, 1.89 mmol) in CH$_2$Cl$_2$ (10 mL) was added triethylamine (1.1 mL, 7.6 mmol) and a solution of mixed carbonate 8e (0.51 g, 1.89 mmol) in CH$_2$Cl$_2$ (5 mL). The resulting mixture was stirred at room temperature for 15 h and was quenched with saturated NaHCO$_3$. The layers were separated and the aqueous layer was extracted with CH$_2$Cl$_2$ (2×20 mL). The combined organic layer was washed with brine, dried with Na$_2$SO$_4$ and concentrated under reduced pressure. The resulting oil was purified by column chromatography (40% EtOAc in hexanes) to provide 9e (518.1 mg, 67%) as a colorless oil.

Example 2.10

Synthesis of Heterocycle Boc-Amine Acid

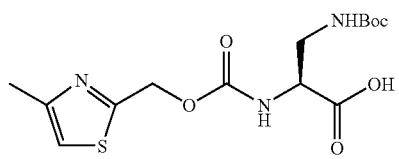

10e

The above ester 9e (25.9 mg, 0.07 mmol) was dissolved in THF (3 mL) and 1N LiOH (1 mL) was added. The resulting mixture was stirred for 30 min and was concentrated under reduced pressure. The solution was acidified carefully to pH 3 by 1N HCl and extracted with EtOAc (2×10 mL). The combined organic layer was washed with brine, dried with Na$_2$SO$_4$ and concentrated under reduced pressure to provide acid 10e as a yellow oil which was used for next step without further purification.

Example 2.11

Synthesis of Exemplary Isostere

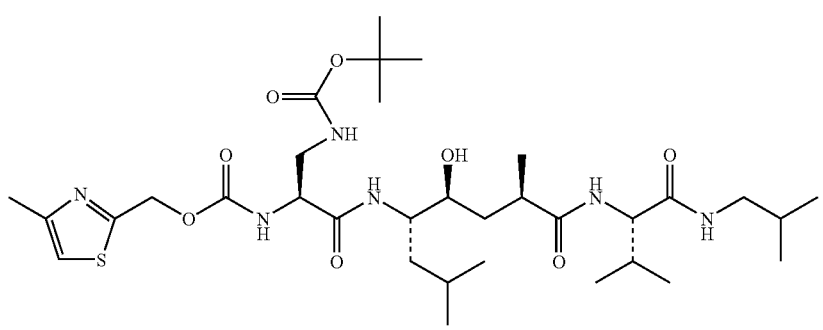

11e

To a stuffed solution of acid 10e (24 mg, 0.07 mmol) in CH₂Cl₂ (3 mL) was added HOBt (11.2 mg 0.08 mmol) and EDCI (15.8 mg, 0.08 mmol), and a solution of amine 7e (39 mg, 0.08 mmol) (pretreated with TFA in DCM and dried under reduced pressure, DIPEA (0.05 mL, 0.29 mmol), and dichloromethane (2 mL)) and N,N-diisopropylethylamine (61 μL, 0.35 mmol) in CH₂Cl₂ (2 mL). The resulting mixture was stirred at room temperature for 15 h and quenched with water. The layers were separated and the aqueous layer was extracted with CH₂Cl₂ (2×10 mL). The combined organic layer was washed with brine, dried with Na₂SO₄ and concentrated under reduced pressure. The resulting oil was dissolved in THF (3 mL) and aqueous HF (48%, 15 drops) was added. The mixture was stirred for 30 min and was quenched with saturated aqueous NaHCO₃. The layers were separated and the aqueous layer was extracted with EtOAc (2×10 mL). The combined organic layer was washed with brine, dried with Na₂SO₄ and concentrated under reduced pressure. The residue was purified by column chromatography (5% MeOH/CHCl₃) to provide the product (13.2 mg) as a solid. ¹H NMR (CDCl₃) δ 6.90 (s, 1H), 5.30 (s, 2H), 4.23-4.25 (m, 1H), 3.99-4.03 (m, 1H), 3.83 (m, 1H), 3.44-3.49 (m, 2H), 3.31-3.39 (m, 1H), 3.05-3.12 (m, 1H), 2.92-2.98 (m, 1H), 2.56-2.63 (m, 1H), 2.42 (s, 3H), 1.98-2.05 (m, 1H), 1.61-1.79 (m, 2H), 1.47-1.54 (m, 3H), 1.40 (s, 9H), 1.26-1.34 (m, 1H), 1.09 (d, 3H, J=6.9 Hz), 0.84-0.92 (m, 18H).

Example 3

Physical Properties of Exemplary Compounds

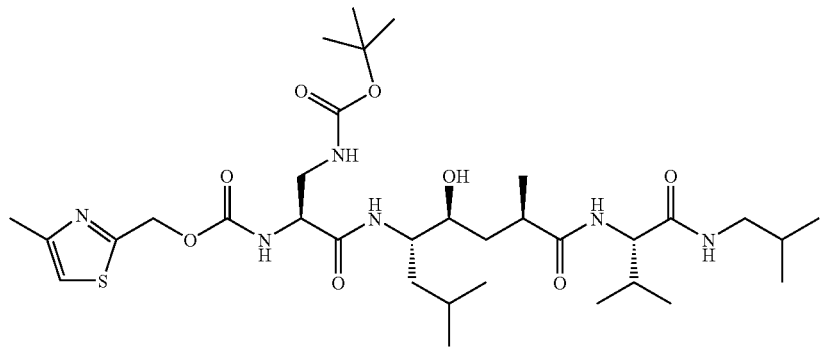

6.90 (s, 1H), 5.30 (s, 2H), 4.23-4.25 (m, 1H), 3.99-4.03 (m, 1H), 3.83 (m, 1H), 3.44-3.49 (m, 2H), 3.31-3.39 (m, 1H), 3.05-3.12 (m, 1H), 2.92-2.98 (m, 1H), 2.56-2.63 (m, 1H), 2.42 (s, 3H), 1.98-2.05 (m, 1H), 1.61-1.79 (m, 2H), 1.47-1.54 (m, 3H), 1.40 (s, 9H), 1.26-1.34 (m, 1H), 1.09 (d, 3H, J=6.9 Hz), 0.84-0.92 (m, 18H).

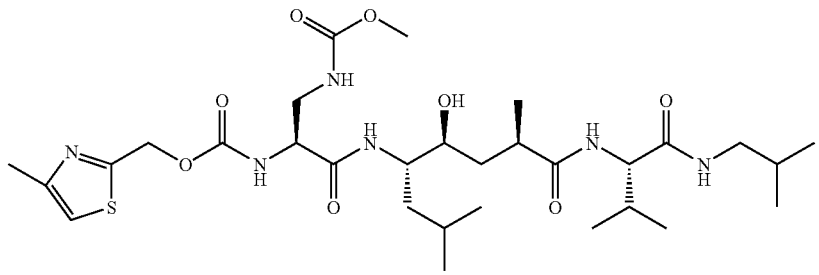

6.90 (s, 1H), 5.30 (s, 2H), 4.24-4.29 (m, 1H), 4.00 (m, 1H), 3.81-3.85 (m, 1H), 3.63 (s, 3H), 3.44-3.52 (m, 3H), 3.04-3.12 (m, 1H), 2.93-2.96 (m, 1H), 2.56-2.62 (m, 1H), 2.42 (s, 3H), 1.96-2.02 (m, 1H), 1.62-1.80 (m, 2H), 1.42-1.50 (m, 3H), 1.28-1.34 (m, 1H), 1.09 (d, 3H, J=6.9 Hz), 0.84-0.91 (m, 18H).
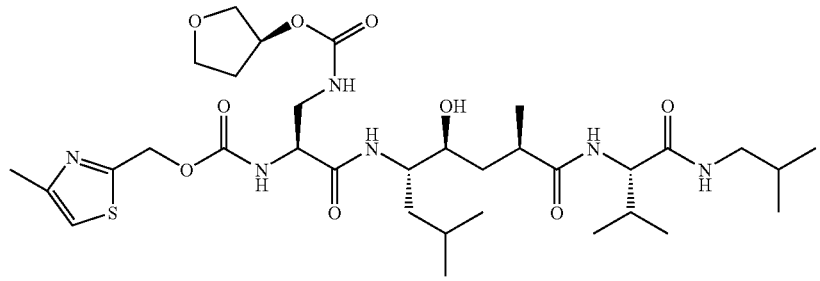
6.90 (s, 1H), 5.28 (s, 2H), 5.18-5.19 (m, 1H), 4.22-4.25 (m, 1H), 3.98-4.03 (m, 1H), 3.76-3.87 (m, 4H), 3.43-3.51 (m, 2H), 3.22-3.39 (m, 1H), 3.02-3.11 (m, 1H), 2.89-2.97 (m, 1H), 2.55-2.60 (m, 1H), 2.40 (s, 3H), 2.06-2.18 (m, 1H), 1.94-2.01 (m, 2H), 1.60-1.76 (m, 2H), 1.28-1.52 (m, 5H), 1.08 (d, 3H, J=6.9 Hz), 0.83-0.90 (m, 18H).
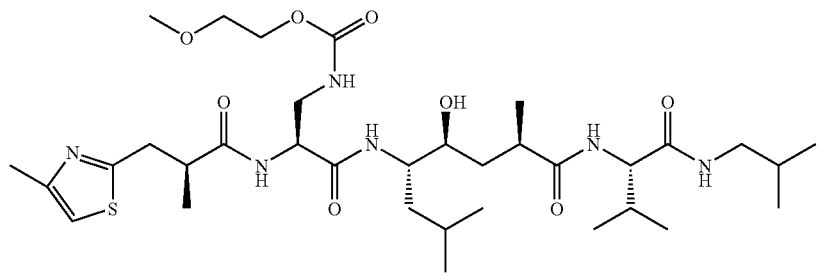
$^1$H NMR (300 MHz, CDCl$_3$+CD$_3$OD): δ 0.80-0.95 (18H, m), 1.12 (3H, d, J=6.9 Hz), 1.21 (3H, d, J=6.9 Hz), 1.14-1.35 (2H, m), 1.62-1.82 (3H, m), 1.94-2.10 (1H, m), 2.39 (3H, s), 2.57-2.70 (3H, m), 2.80-2.89 (1H, m), 2.92-3.04 (2H, m), 3.06-3.14 (1H, m), 3.24-3.33 (1H, m), 3.37 (3H, s), 3.41-3.51 (2H, m), 3.56 (2H, d, J=4.2 Hz), 3.74-3.83 (1H, m), 4.02 (1H, d, J=7.8 Hz), 4.12-4.22 (2H, m), 4.43 (1H, d, J=5.1 Hz), 6.73 (1H, d, s).
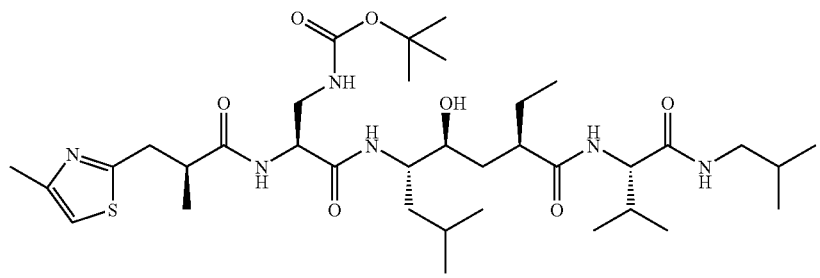

¹H NMR (300 MHz, CDCl₃+CD₃OD): δ 0.88 (21H, m), 1.22 (6H, m), 1.41 (9H, s), 1.58-1.81 (6H, m), 2.04 (1H, m), 2.43 (4H, s), 2.88-3.12 (9H, m), 3.29-3.43 (4H, m), 3.76 (1H, m), 4.03 (1H, d, J=8.1 Hz), 4.38 (1H, m), 6.82 (1H, s).
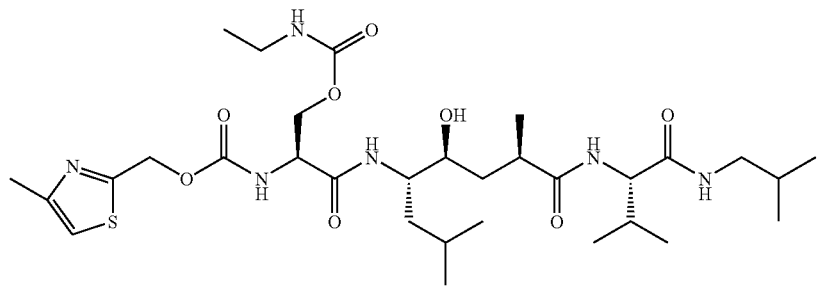
6.89 (s, 1H), 5.27 (s, 2H), 4.33-4.36 (m, 1H), 4.22-4.26 (m, 1H), 4.11-4.17 (m, 1H), 3.96-3.99 (m, 1H), 3.79-3.86 (m, 1H), 3.42-3.50 (m, 2H), 3.10-3.18 (m, 2H), 2.88-2.96 (m, 1H), 2.52-2.56 (m, 1H), 2.38 (s, 3H), 1.94-2.00 (m, 1H), 1.56-1.78 (m, 2H), 1.38-1.52 (m, 3H), 1.20-1.30 (m, 2H), 1.05-1.09 (m, 5H), 0.82-0.88 (m, 18H).
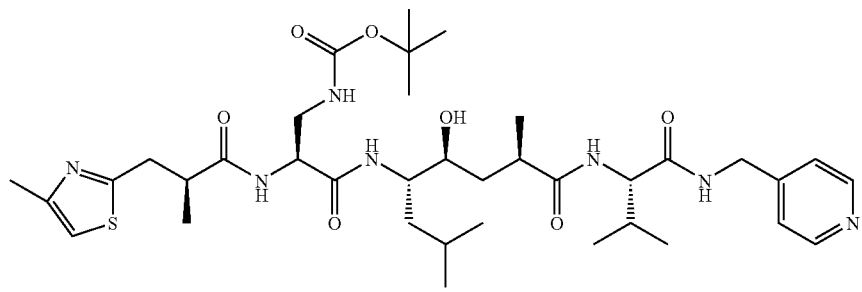
¹H NMR (300 MHz, CDCl₃+CD₃OD): δ 0.10-1.00 (12H, m), 1.10 (3H, d, J=6.4 Hz), 1.19 (3H, d, J=6.6 Hz), 1.40 (9H, s), 1.36-1.56 (2H, m), 1.60-1.74 (1H, m), 2.00-2.12 (1H, m), 2.38 (3H, s), 2.54-2.64 (1H, m), 2.78-2.90 (1H, m), 2.90-3.10 (3H, m), 3.22-3.34 (1H, m), 3.34-3.48 (3H, m), 3.72-3.86 (1H, m), 4.04-4.12 (1H, m), 4.30-4.38 (1H, m), 4.38-4.45 (2H, m), 6.73 (1H, d, J=0.9 Hz), 7.23 (2H, d, J=5.7 Hz), 8.46 (2H, d, J=4.8 Hz).
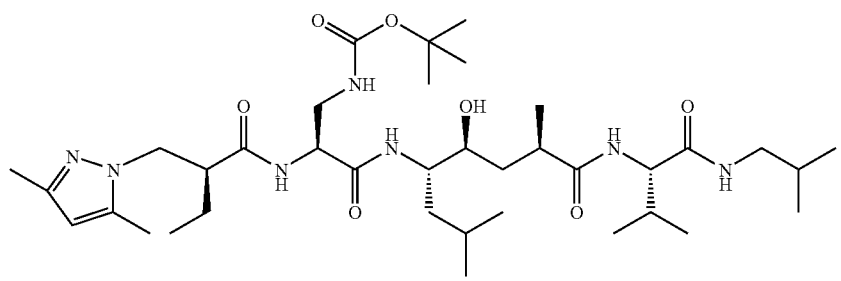

¹H NMR (300 MHz, CDCl₃+CD₃OD): δ 0.80-0.94 (21H, m), 1.08 (3H, d, J=6.6 Hz), 1.38 (9H, s), 1.18-1.80 (4H, m), 1.19-2.06 (1H, m), 2.15 (3H, s), 2.16 (3H, s), 2.50-2.64 (1H, m), 2.66-2.80 (1H, m), 2.86-2.96 (1H, m), 3.02-3.10 (1H, m), 3.20-3.42 (6H, m), 3.70-3.80 (1H, m), 3.80-3.90 (1H, m), 3.98 (1H, d, J=8.1 Hz), 4.05-4.13 (1H, m), 4.30-4.38 (2H, m), 5.70 (1H, s).
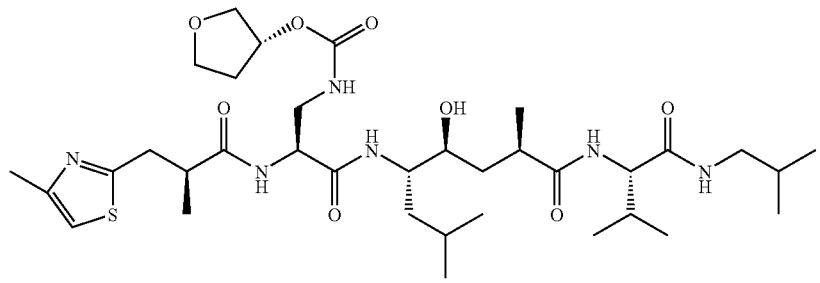
¹H NMR (300 MHz, CDCl₃+CD₃OD): δ 0.76-0.92 (18H, m), 1.05 (3H, d, J=6.9 Hz), 1.13 (3H, d, J=6.6 Hz), 1.18-1.76 (6H, m), 1.84-2.00 (2H, m), 2.00-2.14 (1H, m), 2.33 (3H, d, J=1.2 Hz), 2.48-2.62 (1H, m), 2.70-2.84 (1H, m), 2.84-3.20 (3H, m), 3.38-3.52 (5H, m), 3.60-3.80 (5H, m), 3.90-4.12 (1H, m), 4.62-4.90 (1H, m), 5.20-5.38 (1H, m), 6.70 (1H, d, J=0.9 Hz).
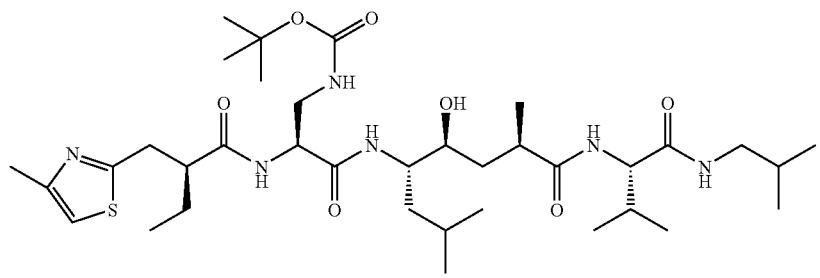
¹H NMR (300 MHz, CDCl₃+CD₃OD): δ 0.80-0.97 (21H, m), 1.11 (3H, d, J=7.2 Hz), 1.41 (9H, s), 1.20-1.80 (8H, m), 1.96-2.08 (1H, m), 2.39 (3H, d, J=1.2 Hz), 2.56-2.72 (2H, m), 2.90-3.18 (3H, m), 3.20-3.30 (1H, m), 3.32-3.48 (3H, m), 3.72-3.84 (1H, m), 3.96-4.06 (1H, m), 4.38-4.46 (1H, m), 6.73 (1H, d, J=0.9 Hz).
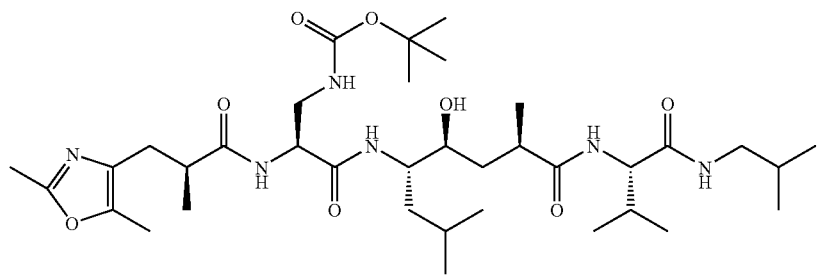

¹H NMR (300 MHz, CDCl₃+CD₃OD): δ 0.78-0.88 (18H, m), 1.04 (3H, d, J=6.9 Hz), 1.34 (9H, s), 1.14-1.46 (5H, m), 1.54-1.76 (2H, m), 1.84-2.02 (1H, m), 2.10 (3H, s), 2.29 (3H, s), 2.24-2.40 (2H, m), 2.40-2.60 (3H, m), 2.82-2.92 (1H, m), 2.98-3.06 (1H, m), 3.22-3.42 (4H, m), 3.60-3.80 (1H, m), 3.94 (1H, d, J=8.1 Hz), 4.26-4.34 (1H, m).

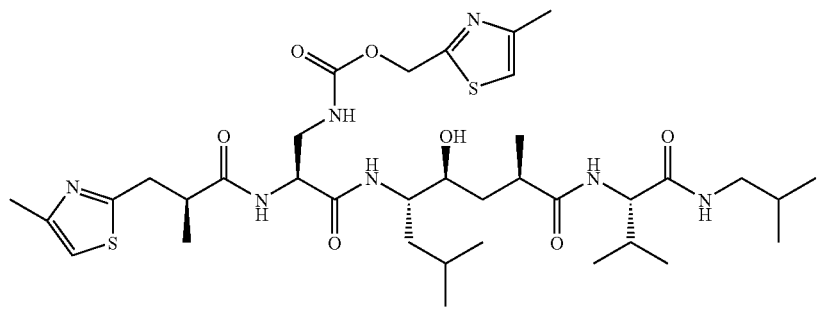

¹H NMR (300 MHz, CDCl₃+CD₃OD): δ 0.76-0.92 (18H, m), 1.03 (3H, d, J=6.9 Hz), 1.13 (3H, d, J=6.9 Hz), 1.00-1.80 (6H, m), 1.88-2.02 (1H, m), 2.34 (3H, s), 2.38 (1H, s), 2.40-2.62 (1H, m), 2.64-2.86 (2H, m), 2.85-3.10 (2H, m), 3.16-3.28 (1H, m), 3.36-3.50 (3H, m), 3.68-3.82 (1H, m), 3.80-4.02 (1H, m), 4.38-4.48 (1H, m), 5.24 (2H, s), 6.69 (1H, s), 6.85 (1H, s).

Example 4

Inhibition of Memapsin 2 Beta-Secretase Activity

Potency of compounds were determined by measurement of their inhibition of memapsin 2 activity toward a fluorescent substrate. Kinetic inhibition experiment were performed using the procedure as described in Ermolieff, et al. (*Biochemistry* 39:12450-12456 (2000), the teachings of which are incorporated hereby in their entirety). Briefly, assays were performed at pH 4, 37° C., by pre-incubation of memapsin 2 enzyme with compound for 20 minutes. Activity measure was initiated by addition of a fluorogenic substrate FS-2 (Bachem Americas, Torrance, Calif.). Fluorescent signal increase over time was measured as a rate of hydrolysis of the peptide substrate. Inhibition of hydrolytic rate was expressed relative to uninhibited controls and fit to a model for tight-binding inhibitors (J. Bieth, in "Proteinase Inhibitors", Bayer Symposium V, 463-469, 1974). The results are presented in Table 1 below.

TABLE 1

| STRUCTURE | M2 Ki | M1 Ki | Cath D Ki | IC50 microM |
|---|---|---|---|---|
| (4-methylthiazol-2-yl)methyl (5S,8S,9S,11R,14S)-9-hydroxy-8-isobutyl-14-isopropyl-11,18-dimethyl-2,6,12,15-tetraoxo-3,7,13,16-tetraazanonadecan-5-yicarbamate | ++ | + | + | − |
| tert-butyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate | + | + | + | |
| (2R,4S,5S)-4-hdroxy-N-((S)-1-(isobutylamino)-3-methyl-1-oxobutan-2-yl)-2,7-dimethyl-5-((S)-2-((S)-2-methyl-3-(4-methylthiazol-2-yl)propanamido)-3-(methylsulfonamido)propanamido)octanamide | ++ | + | ++ | ++ |
| (2R,4S,5S)-5-((S)-3-acetamido-2-((S)-2-methyl-3-(4-methylthiazol-2-yl)propanamido)propanamido)-4-hydroxy-N-((S)-1-(isobutylamino)-3-methyl-1-oxobutan-2-yl)-2,7-dimethyloctanamide | ++ | − | ++ | ++ |
| | ++ | − | + | + |

TABLE 1-continued

| STRUCTURE | M2 Ki | M1 Ki | Cath D Ki | IC50 microM |
|---|---|---|---|---|
| 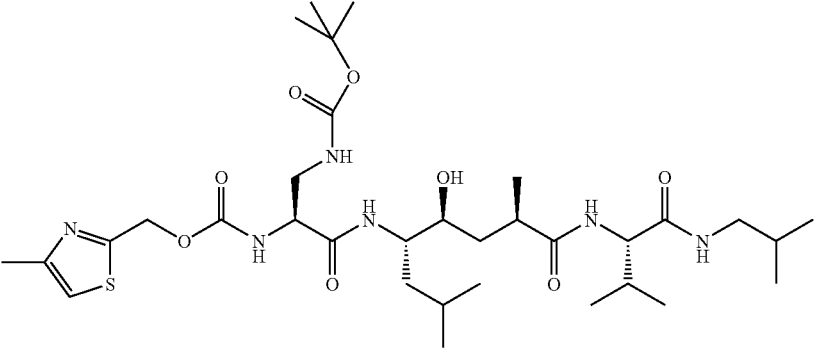 | + | + | + | − |
| (2R,4S,5S)-5-((S)-3-amino-2-((S)-2-methyl-3-(4-methylthiazol-2-yl)propanamido)propanamido)-4-hydroxy-N-((S)-1-(isobutylamino)-3-methyl-1-oxobutan-2-yl)-2,7-dimethyloctanamide | + | − | + | + |
| methyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate | ++ | ++ | ++ | ++ |
| (S)-tetrahydrofuran-3-yl(S)-3-((4S,5S,7R)-5-hydroxy-8-((S)-1-(isobutylamino)-3-methyl-1-oxobutan-2-ylamino)2,7-dimethyl-8-oxooctan-4-ylamino)-2-((S)-2-methyl-3-(4-methylthiazol-2-yl)propanamido)-3-oxopropylcarbamate | ++ | + | ++ | ++ |
| 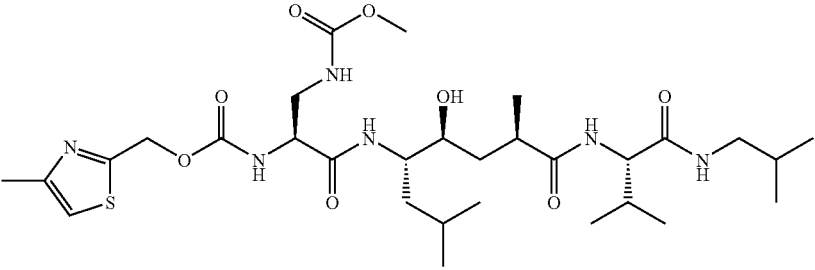 | ++ | ++ | ++ | ++ |
| 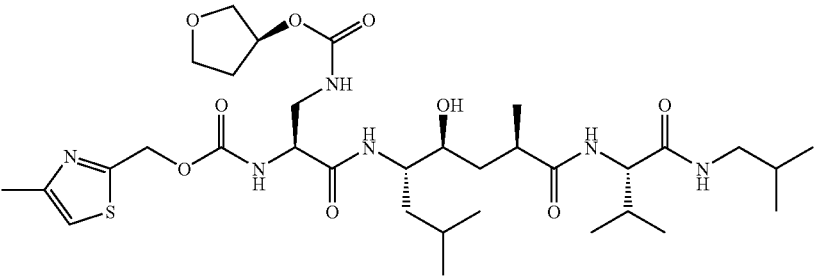 | + | + | + | + |
| 2-methoxyethyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate | ++ | + | ++ | ++ |
| tert-butyl (S)-3-((2S,3S,5 R)-3-hydroxy-6-((S)-1-(isobutylamino)-3-methyl-1-oxobutan-2-ylamino)-5-methyl-6-oxo-1-phenylhexan-2-ylamino)-2-((S)-methyl-3-(4-methylthiazol-2-yl)propanamido)-3-oxopropylcarbamate | ++ | ++ | ++ | + |
| tert-butyl (S)-3-((4S,5S,7R)-5-hydroxy-7-((S)-1-(isobutylamino)-3-methyl-1-oxobutan-2-ylcarbamoyl)-2-methylnonan-4-ylamino)-2-((S)-2-methyl-3-(4-methylthiazol-2-yl)propanamido)-3-oxopropylcarbamate | ++ | ++ | ++ | ++ |
| tert-butyl (S)-3-(4S,5S,7R)-hydromxy-2,7-dimethyl-8-((S)-3-methyl-1-oxo-1-(pyridin-4-ylmethylamino)butan-2-ylamino)-8-oxooctan-4-ylamino)-2-((S)-2-methyl-3-(4- | ++ | − | + | ++ |

TABLE 1-continued

| STRUCTURE | M2 Ki | M1 Ki | Cath D Ki | IC50 microM |
|---|---|---|---|---|
| methylthiazol-2-yl)propanamido)-3-oxopropylcarbamate | | | | |
| tert-butyl (S)-2-((S)-2-((3,5-dimethyl-1H-pyrazol-1-yl)methyl)butanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | ++ | ++ | ++ | ++ |
| (R)-tetrahydrofuran-3-yl (S)-3-((4S,5S,7R)-5-hydroxy-8-((S)-1-(isobutylamino)-3-methyl-1-oxobutan-2-ylamino) 2,7-dimethyl-8-oxooctan-4-ylamino)-2-((S)-2-methyl-3-(4-methylthiazol-2-yl)propanamido)-3-oxopropylcarbamate | ++ | + | ++ | ++ |
| tert-butyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-((4-methylthiazol-2-yl)methyl)butanamido)-3-oxopropylcarbamate | ++ | + | ++ | ++ |
| tert-butyl (S)-3-((2S,3S,5R)-3-hydroxy-6-((S)-1-(isobutylamino)-3-methyl-1-oxobutan-2-ylamino)-1-(4-methoxyphenyl)-5-methyl-6-oxohexan-2-ylamino)-2-((S)-2-methyl-3-(4-methylthiazol-2-yl)propanamido)-3-oxopropylcarbamate | − | − | ++ | |
| tert-butyl (S)-2-((S)-3-(2,5-dimethyloxazol-4-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | ++ | − | ++ | ++ |
| (4-methylthiazol-2-yl)methyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate | ++ | + | ++ | ++ |
| (S)-tetrahydrofuran-3-yl (S)-2-((S)-3-(3,5-dimethyl-1H-pyrazol-1-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | ++ | + | ++ | + |
| tert-butyl (S)-2-((S)-3-(3,5-dimethyl-1H-pyrazol-1-yl)-2-(methoxymethoxy)propanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | + | − | ++ | |
| tert-butyl (2S)-2-(3-(3,5-dimethyl-1H-pyrazol-1-yl)-2-methoxypropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | + | − | ++ | − |
| tert-butyl (S)-2-((S)-3-(3,5-dimethyl-1H-pyrazol-1-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | ++ | + | ++ | |
| tert-butyl (S)-3-((4S,5S,7R)-8-((S)-1-(2,2-dimethylhydrazinyl)-3-methyl-1-oxobutan-2-ylamino)-5-hydroxy-2,7-dimethyl-8-oxooctan-4-ylamino)-2-((S)-2-methyl-3-(4-methylthiazol-2-yl)propanamido)-3-oxopropylcarbamate | ++ | − | + | ++ |
| tert-butyl (S)-3-((2S,3S,5R)-1-(3,5-difluorophenyl)-3-hydroxy-6-((S)-1-(isobutylamino)-3-methyl-1-oxobutan-2-ylamino)-5-methyl-6-oxohexan-2-ylamino)-2-((S)-2-methyl-3-(4-methylthiazol-2-yl)propanamido)-3-oxopropylcarbamate | ++ | | | + |
| tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-2-ylmethylamino)butan-2-ylamino)-8-oxooctan-4-ylamino)-3-oxopropylcarbamate | ++ | | | + |
| tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-4-ylmethylamino)butan-2-ylamino)-8-oxooctan-4-ylamino)-3-oxopropylcarbamate | ++ | | | ++ |
| tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-4-ylmethylamino)butan-2-ylamino)-8-oxooctan-4-ylamino)-3-oxopropylcarbamate | ++ | | | ++ |
| 2-fluoroethyl (2S)-2-(2-((3,5-dimethyl-1H-pyrazol-1-yl)methyl)butanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | ++ | | ++ | + |
| tert-butyl (S)-2-((S)-2-((3,5-dimethyl-1H-pyrazol-1- | ++ | | ++ | + |

TABLE 1-continued

| STRUCTURE | M2 Ki | M1 Ki | Cath D Ki | IC50 microM |
|---|---|---|---|---|
| yl)methyl)butanamido)-3-((4S,5S,7R)-5-hydroxy-2,7-dimethyl-8-((S)-3-methyl-1-oxo-1-(2,2,2-trifluoroethylamino)butan-2-ylamino)-8-oxooctan-4-ylamino)-3-oxopropylcarbamate | | | | |
| tert-butyl (S)-2-((R)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(2,2,2-trifluoroethylamino)butan-2-ylamino)-8-oxooctan-4-ylamino)-3-oxopropylcarbamate | − | | + | |
| tert-butyl (S)-3-((4S,5S,7R)-5-hydroxy-8-((S)-1-(isobutylsulfonyl)-3-methylbutan-2-ylamino)-2,7-dimethyl-8-oxooctan-4-ylamino)-2-((S)-2-methyl-3-(4-methylthiazol-2-yl)propanamido)-3-oxopropylcarbamate | − | | − | |
| isoproyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-((4-methylthiazol-2-yl)methyl)butanamido)-3-oxopropylcarbamate | ++ | | ++ | ++ |
| tert-butyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((R)-2-((4-methylthiazol-2-yl)methyl)butanamido)-3-oxopropylcarbamate | − | | | |
| (2R,4S,5S)-4-hydroxy-N-((S)-1-(isobutylamino)-3-methyl-1-oxobutan-2-yl)-5-((S)-3-(methoxy(methyl)amino)-2-((S)-2-((4-methylthiazol-2-yl)methyl)butanamido)propanamido)-2,7-dimethyloctanamide | + | | − | |
| tert-butyl (2S)-2-(2-azido-3-(3,5-dimethyl-1H-pyrazol-1-yl)propanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | + | | ++ | + |
| tert-butyl (2S)-2-(2-amino-3-(3,5-dimethyl-1H-pyrazol-1-yl)propanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate | + | | + | − |
| (2R,4S,5S)-4-hydroxy-N-((S)-1-(isobutylamino)-3-methyl-1-oxobutan-2-yl)-2,7-dimethyl-5-((S)-2-((S)-2-methyl-3-(4-methylthiazol-2-yl)propanamido)-3-(N-methylmethylsulfonamido)propanamido)octanamide | + | | | + |
| (S)-3-(3-(3,5-dimethyl-1H-pyrazol-1-yl)propanamido)-4-((4S,5S,7R)-5-hydroxy-8-((S)-1-(isobutylamino)-3-methyl-1-oxobutan-2-ylamino)-2,7-dimethyl-8-oxooctan-4-ylamino)-4-oxobutanoic acid | + | ++ | | |
| (S)-2-(3-(3,5-dimethyl-1H-pyrazol-1-yl)propanamido)-N1-((4S,5S,7R)-5-hydroxy-8-((S)-1-(isobutylamino)-3-methyl-1-oxobutan-2-ylamino)-2,7-dimethyl-8-oxooctan-4-yl)succinamide | + | ++ | ++ | |
| (S)-2-(3-(3,5-dimethyl-1H-pyrazol-1-yl)propanamido)-N1-((4S,5S,7R)-5-hydroxy-8-(1-(isobutylcarbamoyl)cyclopentylamino)-2,7-dimethyl-8-oxooctan-4-yl)succinamide | − | ++ | | |
| (S)-2-((S)-2-((3,5-dimethyl-1H-pyrazol-1-yl)methyl)butanamido)-N1-((4S,5S,7R)-5-hydroxy-8-((S)-1-(isobutylamino)-3-methyl-1-oxobutan-2-ylamino)-2,7-dimethyl-8-oxooctan-4-yl)succinamide | + | ++ | ++ | |
| (S)-benzyl 3-(3-(3,5-dimethyl-1H-pyrazol-1-yl)propanamido)-4-((4S,5S,7R)-5-hydroxy-8-((S)-1-(isobutylamino)-3-methyl-1-oxobutan-2-ylamino)-2,7-dimethyl-8-oxooctan-4-ylamino)-4-oxobutanoate | ++ | + | | |
| (S)-2-(3-(3,5-dimethyl-1H-pyrazol-1-yl)propanamido)-N1-((4S,5S,7R)-5-hydroxy-8-(1-(isobutylamino)-2-methyl-1-oxopropan-2-ylamino)-2,7-dimethyl-8-oxooctan-4-yl)succinamide | − | + | | |
| (2S)-2-(3-(3,5-dimethyl-1H-pyrazol-1-yl)-2-methylpropanamido)-N1-((4S,5S,7R)-5-hydroxy-8-((S)-1-(isobutylamino)-3-methyl-1-oxobutan-2-ylamino)-2,7-dimethyl-8-oxooctan-4-yl)succinamide | + | + | | |
| (2S)-2-(3-(3,5-dimethyl-1H-pyrazol-1-yl)propanamido)-N1-((4S,5S,7R)-5-hydroxy-8-(3-hydroxy-1-(isobutylamino)-1-oxopropan-2-ylamino)-2,7-dimethyl-8-oxooctan-4-yl)succinamide | − | + | | |
| (S)-2-(3-(3,5-dimethyl-1H-pyrazol-1-yl)propanamido)-N1-((4S,5S,7R)-5-hydroxy-8-((S)-1-(isobutylamino)-4-methoxy-1-oxobutan-2-ylamino)-2,7-dimethyl-8-oxooctan-4-yl)succinamide | − | + | | |

TABLE 1-continued

| STRUCTURE | M2 Ki | M1 Ki | Cath D Ki | IC50 microM |
|---|---|---|---|---|
| (2,5-dimethyloxazol-4-yl)methyl (5S,8S,9S,11R,14S)-9-hydroxy-8-isobutyl-14-isopropyl-11,18-dimethyl-3,6,12,15-tetraoxo-1-(pyridin-4-yl)-2,7,13,16-tetraazanonadecan-5-ylcarbamate | + | + | ++ | |
| (2S)-2-(3-(3,5-dimethyl-1H-pyrazol-1-yl)-2-methylpropanamido)-N1-((4S,5S,7R)-5-hydroxy-8-((S)-1-(isobutylamino)-3-methyl-1-oxobutan-2-ylamino)-2,7-dimethyl-8-oxooctan-4-yl)succinamide | + | + | | |
| tert-butyl (5R,8S,9S,11 R,14S)-9-hydroxy-8-isobutyl-14-isopropyl-11,18-dimethyl-1-(4-methylthiazol-2-yl)-3,6,12,15-tetraoxo-2,7,13,16-tetraazanonadecan-5-ylcarbamate | ++ | + | | |
| (S)-2-(2-methoxyethoxy)ethyl 3-(((2,5-dimethyloxazol-4-yl)methoxy)carbonylamino)-4-((4S,5S,7R)-5-hydroxy-8-((S)-1-(isobutylamino)-3-methyl-1-oxobutan-2-ylamino) 2,7-dimethyl-8-oxooctan-4-ylamino)-4-oxobutanoate | ++ | − | ++ | |
| (4-methylthiazol-2-yl)methyl (S)-4-amino-1-((4S,5S,7R)-5-hydroxy-8-((S)-1-(isobutylamino)-3-methyl-1-oxobutan 2-ylamino)-2,7-dimethyl-8-oxooctan-4-ylamino)-1,4-dioxobutan-2-ylcarbamate | + | − | − | |
| (2,5-dimethyloxazol-4-yl)methyl (S)-4-amino-1-((4S,5S,7R)-5-hydroxy-8-((S)-1-(isobutylamino)-3-methyl-1-oxobutan-2-ylamino)-2,7-dimethyl-8-oxooctan-4-ylamino)-1,4-dioxobutan-2-ylcarbamate | + | − | ++ | |
| (S)-3-(((2,5-dimethyloxazol-4-yl)methoxy)carbonylamino)-4-((4S,5S,7R)-5-hydroxy-8-((S)-1-(isobutylamino)-3-methyl-1-oxobutan-2-ylamino) 2,7-dimethyl-8-oxooctan-4-ylamino)-4-oxobutanoic acid | + | − | ++ | |
| (S)-N1-((4S,5S,7R)-5-hydroxy-8-((S)-1-(isobutylamino)-3-methyl-1-oxobutan-2-ylamino)-2,7-dimethyl-8-oxooctan-4-yl)-2-((S)-2-methyl-3-(4-methylthiazol-2-yl)propanamido)succinamide | + | − | ++ | |
| (2,5-dimethyloxazol-4-yl)methyl (5S,8S,9S,11R,14S)-9-hydroxy-8-isobutyl-14-isopropyl-2,11,18-trimethyl-3,6,12,15-tetraoxo-2,7,13,16-tetraazanonadecan-5-ylcarbamate | + | − | | |
| (S)-4-((4S,5S,7R)-5-hydroxy-8-((S)-1-(isobutylamino)-3-methyl-1-oxobutan-2-ylamino)-2,7-dimethyl-8-oxooctan-4-ylamino)-3-((S)-2-methyl-3-(4-methylthiazol-2-yl)propanamido)-4-oxobutanoic acid | + | − | + | |
| (S)-benzyl 3-(((2,5-dimethyloxazol-4-yl)methoxy)carbonylamino)-4-((4S,5S,7R)-5-hydroxy-8-((S)-1-(isobutylamino)-3-methyl-1-oxobutan-2-ylamino) 2,7-dimethyl-8-oxooctan-4-ylamino)-4-oxobutanoate | ++ | − | ++ | |
| tert-butyl (5S,8S,9S,11R,14S)-9-hydroxy-8-isobutyl-14-isopropyl-11,18-dimethyl-1-(4-methylthiazol-2-yl)-3,6,12,15-tetraoxo-2,7,13,16-tetraazanonadecan-5-ylcarbamate | + | − | | |
| (S)-N4-ethyl-N1-((4S,5S,7R)-5-hydroxy-8-((S)-1-(isobutylamino)-3-methyl-1-oxobutan-2-ylamino)-2,7-dimethyl-8-oxooctan-4-yl)-2-((S)-2-methyl-3-(4-methylthiazol-2-yl)propanamido)succinamide | ++ | − | | |
| (S)-N1-((4S,5S,7R)-5-hydroxy-8-((S)-1-(isobutylamino)-3-methyl-1-oxobutan-2-ylamino)-2,7-dimethyl-8-oxooctan-4-yl)-N4,N4-dimethyl-2-((S)-2-methyl-3-(4-methylthiazol-2-yl)propanamido)succinamide | + | − | ++ | |

In Table 1, for Ki, the symbol "++" represents a Ki of less than 100 nM; the symbol "+" represents a Ki of 100 to 600 nM; and the symbol "−" represents a Ki of greater than 600 nM. For IC50, The symbol "++" indicates an IC50 of less than 6 µM; "+" indicates an IC50 from 6 to 100 µM; and "−" indicates an IC50 of greater than 100 µM.

Example 5

Inhibition of Memapsin 1 Beta-Secretase Activity and Cathensin D Activity

A substrate peptide $NH_3$-ELDLAVEFWHDR-$CO_2$ (SEQ ID NO.:1) was dissolved at 2 mg/ml in 10% glacial acetic acid and diluted into 0.009 M NaOH to obtain µM concentration at pH 4.1. After equilibration at 37 degrees C., the reactions were initiated by the addition of an aliquot of memapsin 2. Aliquots were removed at time intervals, and combined with an equal volume of MALDI-TOF matrix (α-hydroxycinnamic acid in acetone, 20 mg/ml) and immediately spotted in duplicate onto a stainless-steel MALDI sample plate. MALDI-TOF mass spectrometry was performed on a PE Biosystems Voyager DE instrument at the Molecular Biology Resource Center on campus. The instrument was operated at 25,000 accelerating volts in positive mode with a 150 ns delay. Ions with a mass-to-charge ratio (m/z) were detected in the range of 650-2000 atomic mass units. Data was analyzed by the Voyager Data Explorer module to obtain ion intensity data for mass species of substrates and corresponding products in a given mixture. Relative product formation was calculated as the ratio of signal intensity of the product to the sum of signal intensities of both product and the corresponding substrate. Relative product formed per unit time was obtained from non-linear regression analysis of the data representing the initial 15% formation of product using the model:

$$1 - e^{-kT},$$

where k is the relative hydrolytic rate constant and T is time in seconds. Initial rates were expressed relative to uninhibited controls and fit to a tight-binding model of competitive inhibition as above. Results are shown in Table 1 above.

Example 6

Cellular Aβ IC50 Determinations

The potency of compounds against memapsin 2 activity was determined in a cellular assay of Aβ production. Compounds that successfully penetrate the cell membrane demonstrate their ability to inhibit memapsin 2 activity in endosomal compartments, thus blocking the production of Aβ. Chinese hamster ovary cells that over-express human APP695 with the London and Swedish mutations were seeded in multi-well plates at 10% confluency. Compounds were dissolved in DMSO to concentrations near 1 mM, and diluted into culture media to a final concentration near 4 µM (final 0.4% DMSO). Compounds were diluted serially and applied to cells in multi-well plates 48 h after seeding. Incubation was continued in 5% $CO_2$ at 37 degrees C. for 24 h. Aliquots were removed and assayed for $A\beta_{40}$ content using a sandwich ELISA (BioSource International). Amount of $A\beta_{40}$ over the range of concentration of compounds, relative to control incubations, were fit to a 4-parameter $IC_{50}$ model. Results are shown in Table 1 above.

What is claimed is:

1. A compound of the formula:

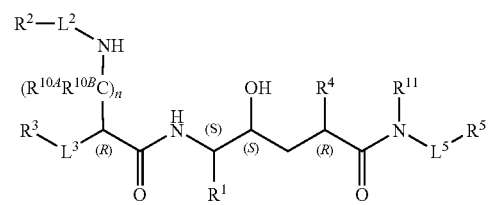

wherein n is 0 to 1;

$R^1$ and $R^4$ are independently —$OR^{31}$, —$C(O)R^{32}$, —$S(O)_rR^{32}$, —$N_3$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^{32}$ is —$N(R^{34})R^{35}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^{34}$ is independently —$N(R^{36})R^{37}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if $R^1$ or $R^4$ is $-S(O)_tR^{32}$, then $R^{34}$ is not $-N(R^{36})R^{37}$, $R^{31}$, $R^{33}$, $R^{35}$, $R^{36}$, and $R^{37}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, t is an integer from 0 to 2;

$R^2$ is an unsubstituted $C_1$-$C_4$ alkyl, unsubstituted furanyl, unsubstituted phenyl, unsubstituted pyridinyl, unsubstituted thiazolyl, furanyl substituted with an unsubstituted $C_1$-$C_4$ alkyl, phenyl substituted with an unsubstituted $C_1$-$C_4$ alkyl, pyridinyl substituted with an unsubstituted $C_1$-$C_4$ alkyl, or thiazolyl substituted with an unsubstituted $C_1$-$C_4$ alkyl;

$R^{11}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10A}$ and $R^{10B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein if n is 1, then $R^{10A}$ is optionally be joined with $R^2$ to form a substituted or unsubstituted heterocycloalkyl, or substituted or unsubstituted heteroaryl;

$L^2$ is $-C(O)-$, $-C(O)NR^6-$, $-C(O)O-$, or $-S(O)_2-$, wherein $R^6$ is hydrogen, or unsubstituted $C_1$-$C_{20}$ alkyl;

-$L^3$-$R^3$ has the formula -$L^{3A}$-C(O)-$L^{3B}$-$L^{3C}$-$R^3$, wherein $L^{3A}$ is $-N(R^{12})-$, wherein $R^{12}$ is hydrogen;

$L^{3B}$ is $-N(R^{18})-$, $-C(R^{19})(R^{20})-$, or $-O-$, wherein $R^{18}$ is hydrogen, or unsubstituted $C_1$-$C_{20}$ alkyl;

$R^{19}$ and $R^{20}$ are independently hydrogen, unsubstituted $C_1$-$C_{20}$ alkyl, $-OR^{21}$, $-N(R^{22})R^{23}$, $C_1$-$C_{20}$ alkyl substituted with $-OR^{21}$, or $N_3$, wherein $R^{21}$, $R^{22}$ and $R^{23}$ are independently hydrogen or unsubstituted $C_1$-$C_{20}$ alkyl; and $L^{3C}$ is methylene;

or -$L^3$-$R^3$ is:

—CH$_2$—C(O)—NH—CH$_2$—R$^3$;
—CH$_2$—C(O)—CHR$^{19}$—CH$_2$—R$^3$;
—CH$_2$—C(O)—O—CH$_2$—R$^3$; or
—O—C(O)—NH—CH$_2$—R$^3$;

$R^3$ is substituted or unsubstituted heteroaryl;

-$L^5$-$R^5$ has the formula

—(C(R$^{24}$)(R$^{25}$))$_q$—C(O)—NH—R$^5$, wherein q is an integer from 0 to 5; and $R^{24}$ and $R^{25}$ are independently hydrogen, substituted or unsubstituted $C_1$-$C_{10}$ alkyl, substituted or unsubstituted 2 to 10 membered heteroalkyl, substituted or unsubstituted $C_5$ to $C_7$ cycloalkyl, substituted or unsubstituted 5 to 7 membered heterocycloalkyl, or substituted or unsubstituted aryl, or substituted or unsubstituted heteroaryl; and $R^5$ is substituted or unsubstituted $C_1$-$C_{10}$ alkyl or $-NR^{29}R^{30}$, wherein $R^{29}$ and $R^{30}$ are independently selected from the group consisting of hydrogen and substituted or unsubstituted $C_1$-$C_{10}$ alkyl;

or any pharmaceutically acceptable salt, racemate, diastereomer, tautomer, or isotope thereof.

2. The compound of claim 1, wherein $R^1$ and $R^4$ are independently hydrogen, substituted or unsubstituted $C_1$-$C_{20}$ alkyl, substituted or unsubstituted 2 to 20 membered heteroalkyl, substituted or unsubstituted $C_5$-$C_7$ cycloalkyl, substituted or unsubstituted 5 to 7 membered heterocycloalkyl, substituted or unsubstituted aryl, or substituted or unsubstituted heteroaryl.

3. The compound of claim 1, wherein $R^1$ and $R^4$ are independently substituted or unsubstituted $C_1$-$C_{20}$ alkyl, substituted or unsubstituted 2 to 20 membered heterocycloalkyl, substituted or unsubstituted aryl, or substituted or unsubstituted heteroaryl.

4. The compound of claim 1, wherein $R^1$ and $R^4$ are independently substituted or unsubstituted $C_1$-$C_{20}$ alkyl, substituted or unsubstituted aryl, or substituted or unsubstituted heteroaryl.

5. The compound of claim 1, wherein $R^1$ is substituted or unsubstituted aryl, substituted or unsubstituted heteroaryl, or substituted or unsubstituted $C_1$-$C_8$ alkyl; and $R^4$ is substituted or unsubstituted aryl, substituted or unsubstituted heteroaryl, or substituted or unsubstituted $C_1$-$C_8$ alkyl.

6. The compound of claim 1, wherein $R^1$ is (a) unsubstituted aryl;

(b) unsubstituted heteroaryl;

(c) aryl substituted with a halogen;

(d) heteroaryl substituted with a halogen; or (e) $C_1$-$C_{20}$ alkyl substituted with a halogen, unsubstituted aryl, aryl substituted with a halogen, unsubstituted heteroaryl, or heteroaryl substituted with a halogen.

7. The compound of claim 1, wherein $R^4$ is (a) unsubstituted aryl;

(b) unsubstituted heteroaryl;

(c) aryl substituted with a halogen;

(d) heteroaryl substituted with a halogen; or (e) $C_1$-$C_{20}$ alkyl substituted with a halogen, unsubstituted aryl, aryl substituted with a halogen, unsubstituted heteroaryl, or heteroaryl substituted with a halogen.

8. The compound of claim 1, wherein $R^1$ is substituted or unsubstituted $C_1$-$C_{20}$ alkyl, substituted or unsubstituted aryl, or substituted or unsubstituted heteroaryl; and $R^4$ is substituted or unsubstituted $C_1$-$C_{20}$ alkyl.

9. The compound of claim 1, wherein $R^1$ is $C_1$-$C_5$ alkyl substituted with a substituted or unsubstituted phenyl, or substituted or unsubstituted pyridinyl; and $R^4$ is unsubstituted $C_1$-$C_8$ alkyl.

10. The compound of claim 9, wherein $R^1$ is $C_1$-$C_5$ alkyl substituted with:
unsubstituted phenyl; unsubstituted pyridinyl; or
phenyl substituted with a halogen, $OR^{14}$, or unsubstituted ($C_1$-$C_5$) alkyl, wherein
$R^{14}$ is hydrogen or unsubstituted ($C_1$-$C_5$) alkyl.

11. The compound of claim 9, wherein $R^1$ is methyl substituted with an unsubstituted phenyl, unsubstituted pyridinyl, 3,5-difluorophenyl, 4-hydroxyphenyl, 3-chloro-4-hydroxyphenyl, or 3-chloro-4-methoxyphenyl.

12. The compound of claim 1, wherein $R^1$ is —$CH_2$—CH($CH_3$)—$CH_3$.

13. The compound of claim 1, wherein $R^4$ is methyl or ethyl.

14. The compound of claim 1,
wherein $R^6$ is hydrogen or unsubstituted $C_1$-$C_4$ alkyl; and n is 1.

15. The compound of claim 14, wherein
$R^2$ is unsubstituted $C_1$-$C_4$ alkyl, unsubstituted furanyl, unsubstituted phenyl, unsubstituted pyridinyl, furanyl substituted with an unsubstituted $C_1$-$C_4$ alkyl, phenyl substituted with an unsubstituted $C_1$-$C_4$ alkyl, pyridinyl substituted with an unsubstituted $C_1$-$C_4$ alkyl, or thiazolyl substituted with an unsubstituted $C_1$-$C_4$ alkyl.

16. The compound of claim 1, wherein -$L^3$-$R^3$ has the formula:

-$L^{3A}$-C(O)-$L^{3B}$-$L^{3C}$-$R^3$.

17. The compound of claim 16, wherein
$R^3$ is a substituted heteroaryl, and
$L^{3B}$ is —C($R^{19}$)($R^{20}$).

18. The compound of claim 17, wherein
$R^{19}$ is hydrogen.

19. The compound of claim 1, wherein -$L^3$-$R^3$ is:
—NH—C(O)—$CHR^{19}$—$CH_2$—$R^3$;
—NH—C(O)—O—$CH_2$—$R^3$;
—NH—C(O)—NH—$CH_2$—$R^3$;
—$CH_2$—C(O)—NH—$CH_2$—$R^3$;
—$CH_2$—C(O)—$CHR^{19}$—$CH_2$—$R^3$;
—$CH_2$—C(O)—O—$CH_2$—$R^3$; or
—O—C(O)—NH—$CH_2$—$R^3$.

20. The compound of claim 1, wherein $R^3$ is substituted or unsubstituted heteroaryl.

21. The compound of claim 1, wherein $R^3$ is unsubstituted or heteroaryl.

22. The compound of claim 1, wherein $R^3$ is substituted or unsubstituted 5 membered heteroaryl.

23. The compound of claim 1, wherein $R^3$ is
unsubstituted heteroaryl; or
heteroaryl substituted with a halogen, —$CF_3$, —OH, —$NH_2$, —CN, unsubstituted $C_1$-$C_{20}$ alkyl, or unsubstituted 2 to 20 membered heteroalkyl.

24. The compound of claim 1, wherein
$R^3$ is substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisoxazolyl.

25. The compound of claim 1, wherein
$R^3$ is substituted or unsubstituted pyrazolyl, substituted or unsubstituted oxazolyl, substituted or unsubstituted thiazolyl, or substituted or unsubstituted furanyl.

26. The compound of claim 1, wherein
$R^3$ is substituted or unsubstituted 1-pyrazolyl, substituted or unsubstituted 4-oxazolyl substituted or unsubstituted 2-oxazolyl, substituted or unsubstituted 2-thiazolyl, or substituted or unsubstituted 2-furanyl.

27. The compound of claim 1, wherein $R^3$ is
1-pyrazolyl substituted with an unsubstituted $C_1$-$C_{20}$ alkyl, or unsubstituted 2 to 20 membered heteroalkyl;
4-oxazolyl substituted with an unsubstituted $C_1$-$C_{20}$ alkyl, or unsubstituted 2 to 20 membered heteroalkyl;
2-oxazolyl substituted with an unsubstituted $C_1$-$C_{20}$ alkyl, or unsubstituted 2 to 20 membered heteroalkyl;
2-thiazolyl substituted with an unsubstituted $C_1$-$C_{20}$ alkyl, or unsubstituted 2 to 20 membered heteroalkyl; or
2-furanyl substituted with an unsubstituted $C_1$-$C_{20}$ alkyl, or unsubstituted 2 to 20 membered heteroalkyl.

28. The compound of claim 1, wherein $R^3$ is
1-pyrazolyl substituted with an unsubstituted $C_1$-$C_5$ alkyl, or unsubstituted 2 to 6 membered heteroalkyl;
4-oxazolyl substituted with an unsubstituted $C_1$-$C_5$ alkyl, or unsubstituted 2 to 6 membered heteroalkyl;
2-oxazolyl substituted with an unsubstituted $C_1$-$C_5$ alkyl, or unsubstituted 2 to 6 membered heteroalkyl;
2-thiazolyl substituted with an unsubstituted $C_1$-$C_5$ alkyl, or unsubstituted 2 to 6 membered heteroalkyl; or
2-furanyl substituted with an unsubstituted $C_1$-$C_5$ alkyl, or unsubstituted 2 to 6 membered heteroalkyl.

29. The compound of claim 1, wherein $R^3$ is
1-pyrazolyl substituted with an unsubstituted $C_1$-$C_5$ alkyl;
4-oxazolyl substituted with an unsubstituted $C_1$-$C_5$ alkyl;
2-oxazolyl substituted with an unsubstituted $C_1$-$C_5$ alkyl;
2-thiazolyl substituted with an unsubstituted $C_1$-$C_5$ alkyl; or
2-furanyl substituted with an unsubstituted $C_1$-$C_5$ alkyl.

30. The compound of claim 1, wherein $R^3$ is:
1-pyrazolyl substituted with an unsubstituted $C_1$-$C_5$ alkyl at the 3 position, the 5 position, or the 3 and 5 position;
4-oxazolyl substituted with an unsubstituted $C_1$-$C_5$ alkyl at the 2 position, the 5-position, or the 2 and 5 position;
2-oxazolyl substituted with an unsubstituted $C_1$-$C_5$ alkyl at the 4 position;
2-thiazolyl substituted with an unsubstituted $C_1$-$C_5$ alkyl at the 4 position; or
2-furanyl substituted with an unsubstituted $C_1$-$C_5$ alkyl at the 5 position.

31. The compound of claim 1, wherein
$R^{24}$ and $R^{25}$ are independently selected from hydrogen and substituted or unsubstituted $C_1$-$C_{10}$ alkyl, and
q is 1 or 2.

32. The compound of claim 31, wherein $R^{25}$ is independently unsubstituted $C_1$-$C_5$ alkyl and $R^{24}$ is hydrogen.

33. The compound of claim 1, wherein $R^{24}$ and $R^{25}$ are independently hydrogen, substituted or unsubstituted $C_1$-$C_{10}$ alkyl, substituted or unsubstituted $C_5$ to $C_7$ cycloalkyl, or substituted or unsubstituted aryl.

34. The compound of claim 1, wherein
$R^{24}$ is hydrogen; and
$R^{25}$ is
(a) unsubstituted $C_1$-$C_{10}$ alkyl, or
(b) unsubstituted $C_5$ to $C_7$ cycloalkyl, unsubstituted aryl, $C_5$ to $C_7$ cycloalkyl substituted with a $C_1$-$C_5$ unsubstituted alkyl, or aryl substituted with a $C_1$-$C_5$ unsubstituted alkyl.

35. The compound of claim 1, wherein
$R^{24}$ is hydrogen; and
$R^{25}$ is unsubstituted $C_1$-$C_{10}$ alkyl.

36. The compound of claim 1, wherein $R^5$ is $C_1$-$C_{10}$ alkyl substituted with a halogen, unsubstituted aryl, aryl substituted with a halogen, unsubstituted heteroaryl, or heteroaryl substituted with a halogen.

37. The compound of claim 1, wherein $R^5$ is
unsubstituted $C_1$-$C_{10}$ alkyl; or
$C_1$-$C_{10}$ alkyl substituted with an —OH, —COOH, halogen, unsubstituted $C_1$-$C_5$ alkyl, or unsubstituted 2 to 5 membered heteroalkyl.

38. The compound of claim 1, wherein $R^5$ is unsubstituted $C_1$-$C_{10}$ alkyl.

39. The compound of claim 1, wherein $R^5$ is unsubstituted $C_1$-$C_5$ alkyl.

40. The compound of claim 1, wherein $R^{11}$ is hydrogen, substituted or unsubstituted alkyl, or substituted or unsubstituted heteroalkyl.

41. The compound of claim 1, wherein $R^{11}$ is hydrogen, unsubstituted $C_1$-$C_{20}$ alkyl, unsubstituted 2 to 20 membered heteroalkyl, $C_1$-$C_{20}$ alkyl substituted with a halogen, or 2 to 20 membered heteroalkyl substituted with a halogen.

42. The compound of claim 1, wherein $R^{11}$ is hydrogen, unsubstituted $C_1$-$C_{20}$ alkyl, unsubstituted 2 to 20 membered heteroalkyl, $C_1$-$C_{20}$ alkyl substituted with a fluorine or chlorine, or 2 to 20 membered heteroalkyl substituted with a fluorine or chlorine.

43. The compound of claim 1, wherein $R^{36}$ and $R^{37}$ are hydrogen or substituted or unsubstituted $C_1$-$C_{10}$ alkyl.

44. The compound of claim 1, wherein $R^{36}$ and $R^{37}$ are hydrogen or unsubstituted $C_1$-$C_5$ alkyl.

45. A method of reducing memapsin 2 beta-secretase activity, the method comprising contacting a memapsin 2 beta-secretase with an effective amount of the compound of claim 1.

46. The method of claim 45, wherein said memapsin 2 beta-secretase is contacted in a cell.

47. A method of selectively reducing memapsin 2 beta-secretase activity relative to memapsin 1 beta-secretase activity, the method comprising contacting a memapsin 2 beta-secretase with an effective amount of the compound of claim 1 in the presence of memapsin 1 beta-secretase.

48. A method of selectively reducing memapsin 2 beta-secretase activity relative to cathepsin D activity, the method comprising contacting a memapsin 2 beta-secretase with an effective amount of the compound of claim 1 in the presence of cathepsin D.

49. A method of selectively reducing memapsin 2 beta-secretase activity relative to memapsin 1 beta-secretase activity and cathepsin D activity, the method comprising contacting a memapsin 2 beta-secretase with an effective amount of the compound of claim 1 in the presence of memapsin 1 beta-secretase and cathepsin D.

50. A compound of claim 1 which is:

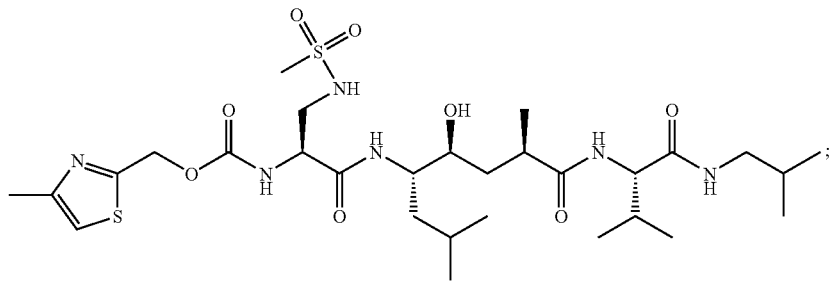

(4-methylthiazol-2-yl)methyl(5S,8S,9S,11R,14S)-9-hydroxy-8-isobutyl-14-isopropyl-11,18-dimethyl-2,6,12,15-tetraoxo-3,7,13,16-tetraazanonadecan-5-ylcarbamate;

tert-butyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate;

(2R,4S,5S)-4-hydroxy-N-((S)-1-(isobutylamino)-3-methyl-1-oxobutan-2-yl)-2,7-dimethyl-5-((S)-2-((S)-2-methyl-3-(4-methylthiazol-2-yl)propanamido)-3-(methylsulfonamido)propanamido)octanamide;

(2R,4S,5S)-5-((S)-3-acetamido-2-((S)-2-methyl-3-(4-methylthiazol-2-yl)propanamido)propanamido)-4-hydroxy-N-((S)-1-(isobutylamino)-3-methyl-1-oxobutan-2-yl)-2,7-dimethyloctanamide;

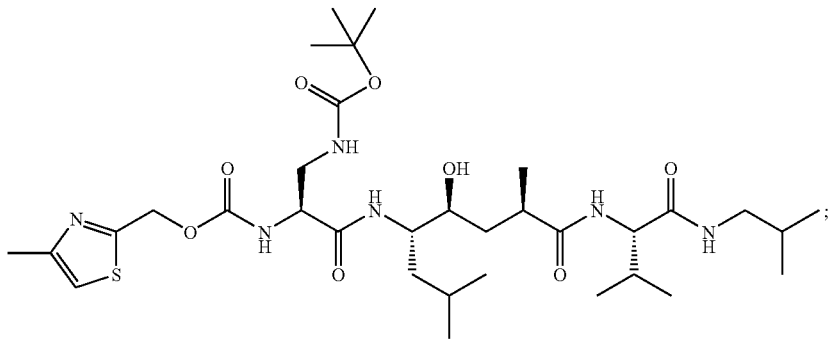

methyl (S)-3-((4S,5S,7R)-5-hydroxy-8-((S)1-(isobuty-lamino)-3-methyl-1-oxobutan-2-ylamino)-2,7-dim-ethyl-8-oxooctan-4-ylamino)-2-((S)-2-methyl-3-(4-methylthiazol-2-yl)propanamido)-3-oxopropylcarbamate;

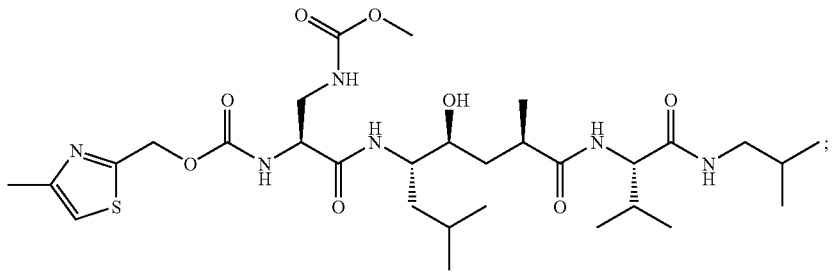

tert-butyl (S)-3-((2S,3S,5R)3-hydroxy-6-((S)-1-(isobuty-lamino)-3-methyl-1-oxobutan-2-ylamino)-5-methyl-6-oxo-1-phenylhexan-2-ylamino)-2-((S)-2-methyl-3-(4-methylthiazol-2-yl)propanamido)-3-oxopropylcarbamate;

tert-butyl (S)-3-((4S,5S,7R)-5-hydroxy-7-((S)-1-(isobuty-lamino)-3-methyl-1-oxobutan-2-ylcarbamoyl)-2-meth-ylnonan-4-ylamino)-2-((S)-2-methyl-3-(4-methylthi-azol-2-yl)propanamido)-3-oxopropylcarbamate;

tert-butyl (S)-3-((4S,5S,7R)-5-hydroxy-2,7-dimethyl-8-((S)-3-methyl-1-oxo-1-(pyridin-4-ylmethylamino)bu-tan-2-ylamino)-8-oxooctan-4-ylamino)-2-((S)-2-me-thyl-3-(4-methylthiazol-2-yl)propanamido)-3-oxopropylcarbamate;

tert-butyl (S)-2-((S)-2-(((3,5-dimethyl-1H-pyrazol-1-yl)methyl)butanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)-3-((4S,5S,7R)-5-hydroxy-8-((S)-1-(isobuty-lamino)-3-methyl-1-oxobutan-2-ylamino)-2,7-dim-ethyl-8-oxooctan-4-ylamino)-2-((S)-2-((4-methylthi-azol-2-yl)methyl)butanamido)-3-oxopropylcarbamate;

tert-butyl (S)-3-((2S,3S,5R)-3-hydroxy-6-((S)-1-(isobuty-lamino)-3-methyl-1-oxobutan-2-ylamino)-1-(4-meth-oxyphenyl)-5-methyl-6-oxohexan-2-ylamino)-2-((S)-2-methyl-3-(4-methylthiazol-2-yl)propanamido)-3-oxopropylcarbamate;

tert-butyl (S)-2-((S)-3-(2,5-dimethyloxazol-4-yl)-2-meth-ylpropanamido)-3-((4S,5S,7R)5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (2S)-2-(3-(3,5-dimethyl-1H-pyrazol-1-yl)-2-(methoxypropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)-2-((S)-3-(3,5-dimethyl-1H-pyrazol-1-yl)-2-methoxypropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)-3-((4S,5S,7R)-8-((S)-1-(2,2-dimethylhy-drazinyl)-3-methyl-1-oxobutan-2-ylamino)-5-hydroxy-2,7-dimethyl-8-oxooctan-4-ylamino)-2-((S)-2-methyl-3-(4-methylthiazol-2-yl)propanamido)-3-oxopropylcarbamate;

tert-butyl (S)-3-((2S,3S,5R)-1-(3,5-difluorophenyl)-3-hy-droxy-6-((S)-1-(isobutylamino)-3-methyl-1-oxobutan-2-ylamino)-5-methyl-6-oxohexan-2-ylamino)-2-((S)-2-methyl-3-(4-methylthiazol-2-yl)propanamido)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-2-ylm-ethylamino)butan-2-ylamino)-8-oxooctan-4-ylamino)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-4-ylm-ethylamino)butan-2-ylamino)-8-oxooctan-4-ylamino)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7- dimethyl-8-((S)-3-methyl-1-oxo-1-(pyridin-4-ylmethylamino)-butan-2-ylamino)-8-oxooctan-4-ylamino)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(2,2,2-trifluoroethylamino)butan-2-ylamino)-8-oxooctan-4-ylamino)-3-oxopropylcarbamate;

isopropyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-((4-methylthiazol-2-yl)methyl)butanamido)-3-oxopropylcarbamate;

tert-butyl (2S)-2-(2-azido-3-(3,5-dimethyl-1H-pyrazol-1-yl)propanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (2S)-2-(2-amino-3-(3,5-dimethyl-1H-pyrazol-1-yl)propanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (5R,8S,9S,11R,14S)-9-hydroxy-8-isobutyl-14-isopropyl-11,18-dimethyl-1-(4-methylthiazol-2-yl)-3,6,12,15-tetraoxo-2,7,13,16-tetraazanonadecan-5-ylcarbamate;

or any pharmaceutically acceptable salt, racemate, diastereomer, tautomer, or isotope thereof.

51. A compound of claim 1 which is:

(2R,4S,5S)-4-hydroxy-N-((S)-1-(isobutylamino)-3-methyl-1-oxobutan-2-yl)-2,7-dimethyl-5-((S)-2-((S)-2-methyl-3-(4-methylthiazol-2-yl)propanamido)-3-(methylsulfonamido)propanamido)octanamide;

(2R,4S,5S)-5-((S)-3-acetamido-2-((S)-2-methyl-3-(4-methylthiazol-2-yl)propanamido)propanamido)-4-hydroxy-N-((S)-1-(isobutylamino)-3-methyl-1-oxobutan-2-yl)-2,7-dimethyloctanamide;

methyl 3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate;

tert-butyl (S)3-((2S,3S,5R)-3-hydroxy-6-((S)-1-(isobutylamino)-3-methyl-1-oxobutan-2-ylamino)-5-methyl-6-oxo-1-phenylhexan-2-ylamino)-2-((S)-2-methyl-3-(4-methylthiazol-2-yl)propanamido)-3-oxopropylcarbamate;

tert-butyl (S)3-((4S,5S,7R)-5-hydroxy-7-((S)-1-(isobutylamino)-3-methyl-1-oxobutan-2-ylcarbamoyl)-2-methylnonan-4-ylamino)-2-((S)-2-methyl-3-(4-methylthiazol-2-yl)propanamido)-3-oxopropylcarbamate;

tert-butyl (S)3-((4S,5S,7R)-5-hydroxy-2,7-dimethyl-8-((S)-3-methyl-1-oxo-1-(pyridin-4-ylmethylamino)butan-2-ylamino)-8-oxooctan-4-ylamino)-2-((S)-2-methyl-3-(4-methylthiazol-2-yl)propanamido)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-((4-methylthiazol-2-yl)methyl)butanamido)-3-oxopropylcarbamate;

tert-butyl (S)-2-((S)-3-(2,5-dimethyloxazol-4-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)-2-((S)-3-(3,5-dimethyl-1H-pyrazol-1-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)3-((4S,5S,7R)-8-((S)-1-(2,2-dimethylhydrazinyl)-3-methyl-1-oxobutan-2-ylamino)-5-hydroxy-2,7-dimethyl-8-oxooctan-4-ylamino)-2-((S)-2-methyl-3-(4-methylthiazol-2-yl)propanamido)-3-oxopropylcarbamate;

tert-butyl (S)3-((2S,3S,5R)-1-(3,5-difluorophenyl)-3-hydroxy-6-((S)-1-(isobutylamino)-3-methyl-1-oxobutan-2-ylamino)-5-methyl-6-oxohexan-2-ylamino)-2-((S)-2-methyl-3-(4-methylthiazol-2-yl)propanamido)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-2-ylmethylamino)butan-2-ylamino)-8-oxooctan-4-ylamino)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-4-ylmethylamino)butan-2-ylamino)-8-oxooctan-4-ylamino)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(pyridin-4-ylmethylamino)butan-2-ylamino)-8-oxooctan-4-ylamino)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-2,7-dimethyl-8-((S)-3-methyl-1-oxo-1-(2,2,2-trifluoroethylamino)butan-2-ylamino)-8-oxooctan-4-ylamino)-3-oxopropylcarbamate;

isopropyl (S)-3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-((4-methylthiazol-2-yl)methyl)butanamido)-3-oxopropylcarbamate;

or any pharmaceutically acceptable salt, racemate, diastereomer, tautomer, or isotope thereof.

52. A compound of claim 1 which is:

tert-butyl (S)3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate;

methyl (S)3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-methyl-3-(4-methylthiazol-2-yl)propanamido)-3-oxopropylcarbamate;

tert-butyl (S)3-((4S,5S,7R)-5-hydroxy-7-((S)-1-(isobutylamino)-3-methyl-1-oxobutan-2-ylcarbamoyl)-2-methylnonan-4-ylamino)-2-((S)-2-methyl-3-(4-methylthiazol-2-yl)propanamido)-3-oxopropylcarbamate;

tert-butyl (S)3-((4S,5S,7R)-5-hydroxy-2,7-dimethyl-8-((S)-3-methyl-1-oxo-1-(pyridin-4-ylmethylamino)butan-2-ylamino)-8-oxooctan-4-ylamino)-2-((S)-2-methyl-3-(4-methylthiazol-2-yl)propanamido)-3-oxopropylcarbamate;

tert-butyl (S)-2-((S)-2-((3,5-dimethyl-1H-pyrazol-1-yl)methyl)butanamido)-3-((4S,5S,7R)-5-hydroxy-8-((S)-

1-(isobutylamino)-3-methyl-1-oxobutan-2-ylamino)-2,
7-dimethyl-8-oxooctan-4-ylamino)-3-
oxopropylcarbamate;

tert-butyl (S)3-((4S,5S,7R)-5-hydroxy-8-((S)-1-(isobutylamino)-3-methyl-1-oxobutan-2-ylamino)-2,7-dimethyl-8-oxooctan-4-ylamino)-2-((S)-2-((4-methylthiazol-2-yl)methyl)butanamido)-3-oxopropylcarbamate;

tert-butyl (S)-2-((S)-3-(2,5-dimethyloxazol-4-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

tert-butyl (S)-2-((S)-3-(3,5-dimethyl-1H-pyrazol-1-yl)-2-methylpropanamido)-3-((4S,5S,7R)-5-hydroxy-8-((S)-1-(isobutylamino)-3-methyl-1-oxobutan-2-ylamino)-2,7-dimethyl-8-oxooctan-4-ylamino)-3-oxopropylcarbamate;

or any pharmaceutically acceptable salt, racemate, diastereomer, tautomer, or isotope thereof.

53. A composition comprising a compound of claim 1 and a pharmaceutically acceptable carrier.

54. A compound according to claim 1, wherein -$L^3$-$R^3$ is —NH—C(O)—CHR$^{19}$—CH$_2$—R$^3$.

55. A compound according to claim 1, wherein -$L^3$-$R^3$ is —NH—C(O)—O—CH$_2$—R$^3$.

56. A compound according to claim 1, wherein -$L^3$-$R^3$ is —NH—C(O)—NH—CH$_2$—R$^3$.

* * * * *